US012767721B2

(12) United States Patent
Yamniuk et al.

(10) Patent No.: US 12,767,721 B2
(45) Date of Patent: Oct. 20, 2026

(54) CD40 ANTAGONIST ANTIBODY VARIANTS WITH IMPROVED PHARMACOKINETIC PROPERTIES

(71) Applicant: BRISTOL-MYERS SQUIBB COMPANY, Princeton, NJ (US)

(72) Inventors: Aaron Yamniuk, Vancouver (CA); Mary Struthers, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 828 days.

(21) Appl. No.: 17/999,271

(22) PCT Filed: May 17, 2021

(86) PCT No.: PCT/US2021/032815
§ 371 (c)(1),
(2) Date: Nov. 18, 2022

(87) PCT Pub. No.: WO2021/236546
PCT Pub. Date: Nov. 25, 2021

(65) Prior Publication Data
US 2023/0203177 A1 Jun. 29, 2023

Related U.S. Application Data

(60) Provisional application No. 63/026,499, filed on May 18, 2020.

(51) Int. Cl.
*C07K 16/28* (2006.01)
*A61K 39/395* (2006.01)
(Continued)

(52) U.S. Cl.
CPC ...... *C07K 16/2878* (2013.01); *A61K 39/3955* (2013.01); *A61K 45/06* (2013.01);
(Continued)

(58) Field of Classification Search
None
See application file for complete search history.

(56) References Cited

U.S. PATENT DOCUMENTS 9,475,879 B2 10/2016 Suri et al.
11,220,550 B2 1/2022 Yamniuk et al.
(Continued)

FOREIGN PATENT DOCUMENTS

CN 103635488 A 3/2014
CN 104918957 A 9/2015
(Continued)

OTHER PUBLICATIONS

Warnders et al. (2018) "Influence of protein properties and protein modification on biodistribution and tumor uptake of anticancer antibodies, antibody derivatives, and non-lg scaffolds," *Med. Res. Rev.* 38: 1837-1873.
(Continued)

*Primary Examiner* — Claire Kaufman
(74) *Attorney, Agent, or Firm* — Banner & Witcoff, Ltd.

(57) ABSTRACT

The disclosure provides variants of an antibody wherein the variant antibodies have modified net charge properties relative to the corresponding unmodified antibody. Certain variants have improved pharmacokinetic properties relative to the corresponding unmodified antibody. Certain antibody variants bind CD40. Compositions and methods of use of the same are also provided.

13 Claims, 8 Drawing Sheets

Specification includes a Sequence Listing.

(51) Int. Cl.
*A61K 45/06* (2006.01)
*A61P 37/06* (2006.01)
*A61K 39/00* (2006.01)

(52) U.S. Cl.
CPC ........ *A61P 37/06* (2018.01); *A61K 2039/505* (2013.01); *C07K 2317/567* (2013.01); *C07K 2317/622* (2013.01); *C07K 2317/73* (2013.01); *C07K 2317/92* (2013.01); *C07K 2317/94* (2013.01)

(56) References Cited

U.S. PATENT DOCUMENTS

| | | | |
|---|---|---|---|
| 11,254,750 | B2 | 2/2022 | Yamniuk et al. |
| 11,261,258 | B2 | 3/2022 | Yamniuk et al. |
| 2011/0243932 | A1 | 10/2011 | Barrett et al. |

FOREIGN PATENT DOCUMENTS

| | | | |
|---|---|---|---|
| CN | 110621697 | A | 12/2019 |
| EP | 2196541 | A1 | 6/2010 |
| WO | WO-2012/149356 | A2 | 11/2012 |
| WO | WO-2014/070934 | A1 | 5/2014 |
| WO | 2016028810 | A1 | 2/2016 |
| WO | 2017040932 | A1 | 3/2017 |
| WO | 2018217976 | A1 | 11/2018 |
| WO | WO-2018/217988 | A1 | 11/2018 |
| WO | WO-2018/237022 | A1 | 12/2018 |
| WO | WO-2020/106620 | A1 | 5/2020 |
| WO | WO-2021/236546 | A1 | 11/2021 |

OTHER PUBLICATIONS

Leipold and Prabhu (2019) "Pharmacokinetic and Pharmacodynamic Considerations in the Design of Therapeutic Antibodies," *Clin. Transl. Sci.* 12: 130-139.

Davies et al. (2005) "TRAF6 is Required for TRAF2-Dependent CD40 Signal Transduction in Nonhemopoietic Cells," *Mol. Cell Biol.* 25(22): 9806-9819.

Cai et al. (2011) "C-terminal lysine processing of human immunoglobulin G2 heavy chain in vivo," *Biotechnol Bioeng.* 108(2): 404-412 (Abstract).

Hoogenboom et al. (1991) "Multi-subunit proteins on the surface of filamentous phage: methodologies for displaying antibody (Fab) heavy and light chains," *Nucleic Acids Res.* 1991, 19(15): 4133-4137.

Boswell et al. (2010) "Effects of charge on antibody tissue distribution and pharmacokinetics," *Bioconjug Chem.* 21(12):2153-63. Epub Nov. 5, 2010. PMID: 21053952.

Bumbaca Yadav et al. (2015) "Evaluating the Use of Antibody Variable Region (Fv) Charge as a Risk Assessment Tool for Predicting Typical Cynomolgus Monkey Pharmacokinetics," *J Biol Chem.* 290(50):29732-41.

Hong et al., (1999), "Pharmacokinetics and organ distribution of cationized colchicine-specific IgG and Fab fragments in rat," *J Pharm Sci.* 88(1):147-153.

Kelly et al. (2015) "High throughput cross-interaction measures for human IgG1 antibodies correlate with clearance rates in mice," *Mabs*, 7(4):770-777.

Lee and Pardridge (2003) "Bioconjugate Chem. Lee HJ, Pardridge WM. Monoclonal antibody radiopharmaceuticals: cationization, pegylation, radiometal chelation, pharmacokinetics, and tumor imaging," *Bioconjug Chem.* 14(3):546-553.

Pardridge et al. (1994) "Cationization of a monoclonal antibody to the human immunodeficiency virus REV protein enhances cellular uptake but does not impair antigen binding of the antibody," *Immunol Lett.* 42(3):191-195.

Pardridge et al. (1998) "Enhanced endocytosis in cultured human breast carcinoma cells and in vivo biodistribution in rats of a humanized monoclonal antibody after cationization of the protein," *J Pharmacol Exp Ther.* 286(1):548-554.

Pardridge et al. (1995) "Enhanced cellular uptake and in vivo biodistribution of a monoclonal antibody following cationization," *J Pharm Sci.* 84(8):943-948.

Putman et al. (2010) "Pharmacokinetic, pharmacodynamic and immunogenicity comparability assessment strategies for monoclonal antibodies," *Trends Biotechnol.*28(10):509-516. Epub Aug. 4, 2010. PMID: 20691488.

Shi (2014) "Biologics: an update and challenge of their pharmacokinetics," *Curr Drug Metab.* 15(3):271-290.

Vugmeyster et al. (2012) "Pharmacokinetics and toxicology of therapeutic proteins: Advances and challenges," World J Biol Chem. 26;3(4):73-92.

Aug. 11, 2021—(WO) International Search Report and Written Opinion—App PCT/US2021/032815.

Feb. 1, 2019—Haraya Kenta et al, "Improvement of pharmacokinetic properties of therapeutic antibodies by antibody engineering", Drug Metabolism and Pharmacokinetics, vol. 34, No. 1, Feb. 1, 2019 (Feb. 1, 2019), p. 25-41, XP055813448 DOI: 10.1016/j.dmpk.2018.10.003 ISSN:1347-4367, the whole document, in particular, p. 27.

May 1, 2010—T. Igawa et al, "Reduced elimination of IgG antibodies by engineering the variable region", Protein Engineering Design and Selection, vol. 23, No. 5, May 1, 2010 (May 1, 2010), p. 385-392, XP055003115 DOI: 10.1093/protein/gzq009, the whole document, in particular, pp. 388-390 and figure 5.

Aug. 6, 2019—Anonymous, "A Study to Evaluate the Safety and Efficacy of Dual Costimulation Blockade With VIB4920 and Belatacept for Prophylaxis of Allograft Rejection in Adults Receiving a Kidney Transplant", Aug. 6, 2019 (Aug. 6, 2019), Retrieved from the Internet: URL:https://clinicaltrials.gov/ct2/show/NCT04046549, XP055828781 [retrieved on Jul. 29, 2021], the whole document.

SEQUENCE LISTING

<160> NUMBER OF SEQ ID NOS: 148

<210> SEQ ID NO 1
<211> LENGTH: 447
<212> TYPE: PRT
<213> ORGANISM: Artificial Sequence
<220> FEATURE:
<223> OTHER INFORMATION: "Description of Artificial Sequence: Synthetic
polypeptide"

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 2
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 2

Gln Val Gln Leu Val Gln Ser Gly Ala Glu Val Gln Gln Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 3
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 3

Gln Val Gln Leu Val Gln Ser Gly Ala Glu Val Gln Gln Pro Gly Ser
1 5 10 15

Ser Val Lys Val Ser Cys Gln Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

```
Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 4
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 4

Gln Val Gln Leu Val Gln Ser Gly Ala Glu Val Glu Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110
```

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 5
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 5

Gln Val Gln Leu Val Gln Ser Gly Ala Glu Val Glu Gln Pro Gly Ser
1               5                   10                  15
```

-continued

```
Ser Val Lys Val Ser Cys Glu Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

```
His Asn His Tyr Thr Gln Lys Ser Leu Ser Leu Ser Pro Gly Lys
        435                 440                 445


<210> SEQ ID NO 6
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 6

Gln Val Gln Leu Val Gln Ser Gly Ala Glu Val Val Lys Pro Gly Ser
1               5                   10                  15

Ser Val Ser Val Ser Cys Ala Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 7
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 7

Gln Val Gln Leu Val Gln Ser Gly Ala Glu Val Lys Lys Pro Gly Ser
1               5                   10                  15

Ser Val Lys Val Ser Cys Glu Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 8
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 8

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Gln Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

Lys Thr Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 9
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 9

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

```
Lys Thr Glu Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 10
<211> LENGTH: 447
<212> TYPE: PRT
<213> ORGANISM: Artificial Sequence
<220> FEATURE:

<223> OTHER INFORMATION: "Description of Artificial Sequence: Synthetic polypeptide"

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Glu Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 11
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Glu Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 12
<211> LENGTH: 447
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Glu Ser Gln Tyr Asn Glu Lys Phe
    50                  55                  60

Lys Thr Arg Val Thr Ile Thr Ala Asp Gln Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 13
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 13

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Lys Trp Met
35 40 45

Gly Gln Ile Asn Pro Thr Thr Gly Arg Ser Gln Tyr Asn Lys Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 14
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 14

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
435 440 445

<210> SEQ ID NO 15
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 15

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 16
<211> LENGTH: 447
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 16

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 17
<211> LENGTH: 214
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 17

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 18
<211> LENGTH: 214
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 18

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Gln Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 214
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 19

Asp Ile Gln Met Thr Gln Ser Pro Ser Phe Leu Ser Ala Ser Val Gly
1               5                   10                  15
```

```
Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Glu Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 20
<211> LENGTH: 214
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 20

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Gln Leu Leu Ile
        35                  40                  45

Tyr Ser Ala Ser Tyr Gln Tyr Thr Gly Val Pro Ser Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 21
<211> LENGTH: 214
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 21

Asp Ile Gln Met Thr Gln Ser Pro Ser Phe Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Gln Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Ser Thr Pro Trp
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 22
<211> LENGTH: 231
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 22

```
Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 23
<211> LENGTH: 232
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 23

```
Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 24
<211> LENGTH: 329
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 25
<211> LENGTH: 330
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 25

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Lys Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 26
<211> LENGTH: 231
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 26

Glu Pro Lys Ser Cys Asp Lys Thr His Thr Cys Pro Pro Cys Pro Ala
1 5 10 15

Pro Glu Leu Leu Gly Gly Lys Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 27
<211> LENGTH: 232
<212> TYPE: PRT

<213> ORGANISM: Artificial Sequence
<220> FEATURE:
<223> OTHER INFORMATION: "Description of Artificial Sequence: Synthetic polypeptide"

<400> SEQUENCE: 27

```
Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 28
<211> LENGTH: 329
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 29
<211> LENGTH: 330
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 30
<211> LENGTH: 214
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 30

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Gln Gln Thr Val Ala Ala
            100                 105                 110
```

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 11
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 31

Lys Ala Ser Gln Asp Val Ser Thr Ala Val Ala
1               5                   10

<210> SEQ ID NO 32
<211> LENGTH: 51
<212> TYPE: DNA
<213> ORGANISM: Artificial Sequence
<220> FEATURE:
<223> OTHER INFORMATION: "Description of Artificial Sequence: Synthetic oligonucleotide"

<400> SEQUENCE: 32
atgagggctt ggatcttctt tctgctctgc ctggccggga gagcgctcgc a 51

<210> SEQ ID NO 33
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 33

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Ser Ala Tyr Asn Gln Lys Phe
    50                  55                  60

Lys Asp Lys Ala Thr Leu Thr Ala Asp Lys Ser Ser Ser Thr Ala Tyr
65                  70                  75                  80

Leu Gln Leu Thr Ser Leu Thr Ser Glu Asp Ser Ala Val Tyr Phe Cys
                85                  90                  95

Ser Arg Trp Gly Leu Pro Pro Phe Ala Tyr Trp Gly Gln Gly Thr Leu
100 105 110

Val Thr Val Ser Ala
115

<210> SEQ ID NO 34
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 34

Gln Val Gln Leu Gln Gln Ser Gly Ala Glu Leu Ala Lys Pro Gly Ser
1 5 10 15

Ser Val Lys Met Ser Cys Lys Ala Ser Gly Tyr Ala Phe Thr Ser Tyr
20 25 30

Trp Met His Trp Val Lys Gln Arg Pro Gly Gln Gly Leu Glu Trp Ile
35 40 45

Gly Tyr Ile Asn Pro Thr Thr Gly Tyr Ser Ala Tyr Asn Gln Lys Phe
50 55 60

Lys Ala Lys Thr Thr Leu Thr Ala Asp Lys Ser Ser Ser Thr Ala Tyr
65 70 75 80

Met Gln Leu Thr Ser Leu Thr Phe Glu Asp Ser Ala Val Tyr Phe Cys
85 90 95

Ser Arg Trp Gly Leu Pro Pro Phe Ala Tyr Trp Gly Gln Gly Thr Leu
100 105 110

Val Thr Val Ser Ala
115

<210> SEQ ID NO 35
<211> LENGTH: 446
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 35

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 36
<211> LENGTH: 446
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 36

Gln Val Gln Leu Val Gln Ser Gly Ala Glu Val Glu Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

```
Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 37
<211> LENGTH: 446

<212> TYPE: PRT
<213> ORGANISM: Artificial Sequence
<220> FEATURE:
<223> OTHER INFORMATION: "Description of Artificial Sequence: Synthetic
polypeptide"

<400> SEQUENCE: 37

Gln Val Gln Leu Val Gln Ser Gly Ala Glu Val Glu Gln Pro Gly Ser
1 5 10 15

Ser Val Lys Val Ser Cys Glu Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 38
<211> LENGTH: 446
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 38

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 39
<211> LENGTH: 446
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 39

Gln Val Gln Leu Val Gln Ser Gly Ala Glu Val Glu Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 40
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 40

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 41
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 41

Asp Ile Gln Met Thr Gln Ser Pro Ser Phe Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Gln Leu Leu Ile
35 40 45

Tyr Ser Ala Ser Tyr Gln Tyr Thr Gly Val Pro Ser Gln Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Ser Thr Pro Trp
85 90 95

Thr Phe Gly Gly Gly Thr Lys Val Glu Ile Lys
100 105

<210> SEQ ID NO 42
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 42

Asp Ile Gln Met Thr Gln Ser Pro Ser Phe Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Glu Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Ser Thr Pro Trp
85 90 95

Thr Phe Gly Gly Gly Thr Lys Val Glu Ile Lys
100 105

<210> SEQ ID NO 43
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 43

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 44
<211> LENGTH: 117
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 44

Gln Val Gln Leu Val Gln Ser Gly Ala Glu Val Glu Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 45
<211> LENGTH: 107
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 45

Asp Ile Gln Met Thr Gln Ser Pro Ser Phe Leu Ser Ala Ser Val Gly
1 5 10 15

Asp Arg Val Thr Ile Thr Cys Lys Ala Ser Gln Asp Val Ser Thr Ala
20 25 30

```
Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105


<210> SEQ ID NO 46
<211> LENGTH: 117
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 46

Gln Val Gln Leu Val Gln Ser Gly Ala Glu Val Glu Gln Pro Gly Ser
1               5                   10                  15

Ser Val Lys Val Ser Cys Glu Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115


<210> SEQ ID NO 47
<211> LENGTH: 215
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val
    210                 215


<210> SEQ ID NO 48
<211> LENGTH: 216
<212> TYPE: PRT
<213> ORGANISM: Artificial Sequence
<220> FEATURE:
<223> OTHER INFORMATION: “Description of Artificial Sequence: Synthetic
      polypeptide”

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Gln Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Thr
    210                 215


<210> SEQ ID NO 49
```

<211> LENGTH: 215
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 49

Gln Val Gln Leu Val Gln Ser Gly Ala Glu Val Glu Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val
210 215

<210> SEQ ID NO 50
<211> LENGTH: 215
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 50

Gln Val Gln Leu Val Gln Ser Gly Ala Glu Val Glu Gln Pro Gly Ser
1 5 10 15

Ser Val Lys Val Ser Cys Glu Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val
210 215

<210> SEQ ID NO 51
<211> LENGTH: 17
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 51

Met Arg Ala Trp Ile Phe Phe Leu Leu Cys Leu Ala Gly Arg Ala Leu
1 5 10 15

Ala

<210> SEQ ID NO 52
<211> LENGTH: 277
<212> TYPE: PRT
<213> ORGANISM: Homo sapiens

<400> SEQUENCE: 52

Met Val Arg Leu Pro Leu Gln Cys Val Leu Trp Gly Cys Leu Leu Thr
1 5 10 15

Ala Val His Pro Glu Pro Pro Thr Ala Cys Arg Glu Lys Gln Tyr Leu
20 25 30

Ile Asn Ser Gln Cys Cys Ser Leu Cys Gln Pro Gly Gln Lys Leu Val
35 40 45

Ser Asp Cys Thr Glu Phe Thr Glu Thr Glu Cys Leu Pro Cys Gly Glu
50 55 60

Ser Glu Phe Leu Asp Thr Trp Asn Arg Glu Thr His Cys His Gln His
65 70 75 80

Lys Tyr Cys Asp Pro Asn Leu Gly Leu Arg Val Gln Gln Lys Gly Thr
85 90 95

Ser Glu Thr Asp Thr Ile Cys Thr Cys Glu Glu Gly Trp His Cys Thr
100 105 110

Ser Glu Ala Cys Glu Ser Cys Val Leu His Arg Ser Cys Ser Pro Gly
115 120 125

Phe Gly Val Lys Gln Ile Ala Thr Gly Val Ser Asp Thr Ile Cys Glu
130 135 140

Pro Cys Pro Val Gly Phe Phe Ser Asn Val Ser Ser Ala Phe Glu Lys
145 150 155 160

Cys His Pro Trp Thr Ser Cys Glu Thr Lys Asp Leu Val Val Gln Gln
165 170 175

Ala Gly Thr Asn Lys Thr Asp Val Val Cys Gly Pro Gln Asp Arg Leu
180 185 190

Arg Ala Leu Val Val Ile Pro Ile Ile Phe Gly Ile Leu Phe Ala Ile
195 200 205

Leu Leu Val Leu Val Phe Ile Lys Lys Val Ala Lys Lys Pro Thr Asn
210 215 220

Lys Ala Pro His Pro Lys Gln Glu Pro Gln Glu Ile Asn Phe Pro Asp
225 230 235 240

Asp Leu Pro Gly Ser Asn Thr Ala Ala Pro Val Gln Glu Thr Leu His
245 250 255

Gly Cys Gln Pro Val Thr Gln Glu Asp Gly Lys Glu Ser Arg Ile Ser
260 265 270

Val Gln Glu Arg Gln
275

<210> SEQ ID NO 53
<211> LENGTH: 5
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 53

Ser Tyr Trp Met His
1 5

<210> SEQ ID NO 54
<211> LENGTH: 17
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 54

Gln Ile Asn Pro Thr Thr Gly Arg Ser Gln Tyr Asn Glu Lys Phe Lys
1 5 10 15

Thr

<210> SEQ ID NO 55
<211> LENGTH: 8
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 55

Trp Gly Leu Gln Pro Phe Ala Tyr
1 5

<210> SEQ ID NO 56
<211> LENGTH: 446
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 56

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 57
<211> LENGTH: 7
<212> TYPE: PRT
<213> ORGANISM: Artificial Sequence
<220> FEATURE:
<223> OTHER INFORMATION: "Description of Artificial Sequence: Synthetic
      peptide"

<400> SEQUENCE: 57

Ser Ala Ser Tyr Arg Tyr Thr
1               5


<210> SEQ ID NO 58
<211> LENGTH: 9
<212> TYPE: PRT
<213> ORGANISM: Artificial Sequence
<220> FEATURE:
<223> OTHER INFORMATION: "Description of Artificial Sequence: Synthetic
      peptide"

<400> SEQUENCE: 58

Gln Gln His Tyr Ser Thr Pro Trp Thr
1               5


<210> SEQ ID NO 59
<211> LENGTH: 117
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 59

Gln Val Gln Leu Val Gln Ser Gly Ala Glu Val Gln Gln Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115


<210> SEQ ID NO 60
<211> LENGTH: 117
<212> TYPE: PRT
<213> ORGANISM: Artificial Sequence
<220> FEATURE:
```

<223> OTHER INFORMATION: "Description of Artificial Sequence: Synthetic polypeptide"

<400> SEQUENCE: 60

Gln Val Gln Leu Val Gln Ser Gly Ala Glu Val Gln Gln Pro Gly Ser
1 5 10 15

Ser Val Lys Val Ser Cys Gln Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 61
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 61

Gln Val Gln Leu Val Gln Ser Gly Ala Glu Val Val Lys Pro Gly Ser
1 5 10 15

Ser Val Ser Val Ser Cys Ala Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 62
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 62

Gln Val Gln Leu Val Gln Ser Gly Ala Glu Val Lys Lys Pro Gly Ser
1 5 10 15

Ser Val Lys Val Ser Cys Glu Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 63
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 63

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Gln Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

Lys Thr Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 64
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 64

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

Lys Thr Glu Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 65
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 65

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Gln Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 66
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 66

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Glu Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 67
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 67

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Glu Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 68
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 68

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Glu Ser Gln Tyr Asn Glu Lys Phe
50 55 60

Lys Thr Arg Val Thr Ile Thr Ala Asp Gln Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 69
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115
```

<210> SEQ ID NO 70
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 70

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Gln Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105
```

<210> SEQ ID NO 71
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 71

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30
```

```
Trp Met His Trp Val Arg Gln Ala Pro Gly Gln Gly Leu Lys Trp Met
        35                  40                  45

Gly Gln Ile Asn Pro Thr Thr Gly Arg Ser Gln Tyr Asn Lys Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115


<210> SEQ ID NO 72
<211> LENGTH: 108
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 72

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Gln Gln
            100                 105


<210> SEQ ID NO 73
<211> LENGTH: 117
<212> TYPE: PRT
<213> ORGANISM: Artificial Sequence
<220> FEATURE:
<223> OTHER INFORMATION: "Description of Artificial Sequence: Synthetic
      polypeptide"
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (50)..(66)
<223> OTHER INFORMATION: Any amino acid
<220> FEATURE:
<221> NAME/KEY: MOD_RES
<222> LOCATION: (99)..(106)
<223> OTHER INFORMATION: Any amino acid

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Xaa Xaa
            20                  25                  30
```

```
Xaa Xaa Xaa Trp Val Arg Gln Ala Pro Gly Gln Gly Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Trp Gly Gln Gly Thr Leu
            100                 105                 110

Val Thr Val Ser Ser
        115


<210> SEQ ID NO 74
<211> LENGTH: 107
<212> TYPE: PRT
<213> ORGANISM: Artificial Sequence
<220> FEATURE:
<223> OTHER INFORMATION: "Description of Artificial Sequence: Synthetic
      polypeptide"
<220> FEATURE:
<221> NAME/KEY: MOD_RES
<222> LOCATION: (24)..(34)
<223> OTHER INFORMATION: Any amino acid
<220> FEATURE:
<221> NAME/KEY: MOD_RES
<222> LOCATION: (50)..(56)
<223> OTHER INFORMATION: Any amino acid
<220> FEATURE:
<221> NAME/KEY: MOD_RES
<222> LOCATION: (89)..(97)
<223> OTHER INFORMATION: Any amino acid

<400> SEQUENCE: 74

Asp Ile Gln Met Thr Gln Ser Pro Ser Phe Leu Ser Ala Ser Val Gly
1               5                   10                  15

Asp Arg Val Thr Ile Thr Cys Xaa Xaa Xaa Xaa Xaa Xaa Xaa Xaa Xaa
            20                  25                  30

Xaa Xaa Trp Tyr Gln Gln Lys Pro Gly Lys Ala Pro Lys Leu Leu Ile
        35                  40                  45

Tyr Xaa Xaa Xaa Xaa Xaa Xaa Xaa Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa Xaa
                85                  90                  95

Xaa Phe Gly Gly Gly Thr Lys Val Glu Ile Lys
            100                 105


<210> SEQ ID NO 75
<211> LENGTH: 108
<212> TYPE: PRT
<213> ORGANISM: Artificial Sequence
<220> FEATURE:
<223> OTHER INFORMATION: "Description of Artificial Sequence: Synthetic
      polypeptide"
<220> FEATURE:
<221> NAME/KEY: MOD_RES
<222> LOCATION: (24)..(34)
<223> OTHER INFORMATION: Any amino acid
<220> FEATURE:
<221> NAME/KEY: MOD_RES
<222> LOCATION: (50)..(56)
<223> OTHER INFORMATION: Any amino acid
<220> FEATURE:
```

<221> NAME/KEY: MOD_RES
<222> LOCATION: (89)..(97)
<223> OTHER INFORMATION: Any amino acid

<400> SEQUENCE: 75

Asp Ile Gln Met Thr Gln Ser Pro Ser Phe Leu Ser Ala Ser Val Gly
1 5 10 15

Asp Arg Val Thr Ile Thr Cys Xaa Xaa Xaa Xaa Xaa Xaa Xaa Xaa Xaa
20 25 30

Xaa Xaa Trp Tyr Gln Gln Lys Pro Gly Lys Ala Pro Lys Leu Leu Ile
35 40 45

Tyr Xaa Xaa Xaa Xaa Xaa Xaa Xaa Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Xaa Xaa Xaa Xaa Xaa Xaa Xaa Xaa
85 90 95

Xaa Phe Gly Gly Gly Thr Lys Val Glu Ile Lys Arg
100 105

<210> SEQ ID NO 76
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (50)..(66)
<223> OTHER INFORMATION: Any amino acid
<220> FEATURE:
<221> NAME/KEY: MOD_RES
<222> LOCATION: (99)..(106)
<223> OTHER INFORMATION: Any amino acid

<400> SEQUENCE: 76

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Xaa Xaa
20 25 30

Xaa Xaa Xaa Trp Val Arg Gln Ala Pro Gly Gln Gly Leu Glu Trp Met
35 40 45

Gly Xaa Xaa Xaa Xaa Xaa Xaa Xaa Xaa Xaa Xaa Xaa Xaa Xaa Xaa Xaa
50 55 60

Xaa Xaa Gln Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Xaa Xaa Xaa Xaa Xaa Xaa Xaa Xaa Trp Gly Gln Gly Thr Leu
100 105 110

Val Thr Val Ser Ser
115

<210> SEQ ID NO 77
<211> LENGTH: 119
<212> TYPE: PRT
<213> ORGANISM: Artificial Sequence
<220> FEATURE:
<223> OTHER INFORMATION: "Description of Artificial Sequence: Synthetic
polypeptide"
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (51)..(67)
<223> OTHER INFORMATION: Any amino acid
<220> FEATURE:
<221> NAME/KEY: MOD_RES
<222> LOCATION: (100)..(107)
<223> OTHER INFORMATION: Any amino acid

<400> SEQUENCE: 77

```
Gln Val Gln Leu Val Gln Ser Gly Ala Glu Val Glu Lys Pro Gly Ser
1               5                   10                  15

Ser Val Lys Val Ser Cys Lys Ala Ser Gly Tyr Ala Phe Thr Xaa Xaa
            20                  25                  30

Xaa Xaa Xaa Trp Val Arg Gln Ala Pro Gly Gln Gly Leu Glu Trp Met
        35                  40                  45

Gly Gln Xaa Xaa Xaa Xaa Xaa Xaa Xaa Xaa Xaa Xaa Xaa Xaa Xaa Xaa
    50                  55                  60

Xaa Xaa Xaa Arg Val Thr Ile Thr Ala Asp Lys Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Xaa Xaa Xaa Xaa Xaa Xaa Xaa Xaa Tyr Trp Gly Gln Gly
            100                 105                 110

Thr Leu Val Thr Val Ser Ser
        115
```

<210> SEQ ID NO 78
<211> LENGTH: 117
<212> TYPE: PRT
<213> ORGANISM: Artificial Sequence
<220> FEATURE:
<223> OTHER INFORMATION: "Description of Artificial Sequence: Synthetic
polypeptide"
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (50)..(66)
<223> OTHER INFORMATION: Any amino acid
<220> FEATURE:
<221> NAME/KEY: MOD_RES
<222> LOCATION: (99)..(106)
<223> OTHER INFORMATION: Any amino acid

<400> SEQUENCE: 78

```
Gln Val Gln Leu Val Gln Ser Gly Ala Glu Val Glu Lys Pro Gly Ser
1               5                   10                  15

Ser Val Lys Val Ser Cys Lys Ala Ser Gly Tyr Ala Phe Thr Xaa Xaa
            20                  25                  30

Xaa Xaa Xaa Trp Val Arg Gln Ala Pro Gly Gln Gly Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
85 90 95

Ala Arg Xaa Xaa Xaa Xaa Xaa Xaa Xaa Xaa Trp Gly Gln Gly Thr Leu
100 105 110

Val Thr Val Ser Ser
115

<210> SEQ ID NO 79
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (50)..(66)
<223> OTHER INFORMATION: Any amino acid
<220> FEATURE:
<221> NAME/KEY: MOD_RES
<222> LOCATION: (99)..(106)
<223> OTHER INFORMATION: Any amino acid

<400> SEQUENCE: 79

Gln Val Gln Leu Val Gln Ser Gly Ala Glu Val Glu Gln Pro Gly Ser
1 5 10 15

Ser Val Lys Val Ser Cys Glu Ala Ser Gly Tyr Ala Phe Thr Xaa Xaa
20 25 30

Xaa Xaa Xaa Trp Val Arg Gln Ala Pro Gly Gln Gly Leu Glu Trp Met
35 40 45

Gly Xaa Xaa Xaa Xaa Xaa Xaa Xaa Xaa Xaa Xaa Xaa Xaa Xaa Xaa Xaa
50 55 60

Xaa Xaa Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Xaa Xaa Xaa Xaa Xaa Xaa Xaa Xaa Trp Gly Gln Gly Thr Leu
100 105 110

Val Thr Val Ser Ser
115

<210> SEQ ID NO 80
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"
<220> FEATURE:
<221> NAME/KEY: MOD_RES
<222> LOCATION: (24)..(34)
<223> OTHER INFORMATION: Any amino acid
<220> FEATURE:
<221> NAME/KEY: MOD_RES
<222> LOCATION: (50)..(53)
<223> OTHER INFORMATION: Any amino acid
<220> FEATURE:
<221> NAME/KEY: MOD_RES
<222> LOCATION: (55)..(56)
<223> OTHER INFORMATION: Any amino acid
<220> FEATURE:
<221> NAME/KEY: MOD_RES
<222> LOCATION: (89)..(97)
<223> OTHER INFORMATION: Any amino acid

<400> SEQUENCE: 80

```
Asp Ile Gln Met Thr Gln Ser Pro Ser Phe Leu Ser Ala Ser Val Gly
1               5                   10                  15

Asp Arg Val Thr Ile Thr Cys Xaa Xaa Xaa Xaa Xaa Xaa Xaa Xaa Xaa
            20                  25                  30

Xaa Xaa Trp Tyr Gln Gln Lys Pro Gly Lys Ala Pro Gln Leu Leu Ile
        35                  40                  45

Tyr Xaa Xaa Xaa Xaa Gln Xaa Xaa Gly Val Pro Ser Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa Xaa
                85                  90                  95

Xaa Phe Gly Gly Gly Thr Lys Val Glu Ile Lys
            100                 105
```

<210> SEQ ID NO 81
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"
<220> FEATURE:
<221> NAME/KEY: MOD_RES
<222> LOCATION: (24)..(34)
<223> OTHER INFORMATION: Any amino acid
<220> FEATURE:
<221> NAME/KEY: MOD_RES
<222> LOCATION: (50)..(56)
<223> OTHER INFORMATION: Any amino acid
<220> FEATURE:
<221> NAME/KEY: MOD_RES
<222> LOCATION: (89)..(97)
<223> OTHER INFORMATION: Any amino acid

<400> SEQUENCE: 81

```
Asp Ile Gln Met Thr Gln Ser Pro Ser Phe Leu Ser Ala Ser Val Gly
1               5                   10                  15

Asp Arg Val Thr Ile Thr Cys Xaa Xaa Xaa Xaa Xaa Xaa Xaa Xaa Xaa
            20                  25                  30

Xaa Xaa Trp Tyr Gln Gln Lys Pro Gly Lys Ala Pro Glu Leu Leu Ile
        35                  40                  45

Tyr Xaa Xaa Xaa Xaa Xaa Xaa Xaa Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa Xaa
                85                  90                  95

Xaa Phe Gly Gly Gly Thr Lys Val Glu Ile Lys
            100                 105
```

<210> SEQ ID NO 82
<211> LENGTH: 98
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 82

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val

<210> SEQ ID NO 83
<211> LENGTH: 107
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 83

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 84
<211> LENGTH: 446
<212> TYPE: PRT
<213> ORGANISM: Artificial Sequence
<220> FEATURE:
<223> OTHER INFORMATION: “Description of Artificial Sequence: Synthetic polypeptide”

<400> SEQUENCE: 84

Gln Val Gln Leu Val Gln Ser Gly Ala Glu Val Glu Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 85
<211> LENGTH: 446
<212> TYPE: PRT
<213> ORGANISM: Artificial Sequence
<220> FEATURE:
<223> OTHER INFORMATION: “Description of Artificial Sequence: Synthetic
      polypeptide”

<400> SEQUENCE: 85

Gln Val Gln Leu Val Gln Ser Gly Ala Glu Val Glu Gln Pro Gly Ser
1 5 10 15

Ser Val Lys Val Ser Cys Glu Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 86
<211> LENGTH: 215
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Gln Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val
    210                 215


<210> SEQ ID NO 87
<211> LENGTH: 232
<212> TYPE: PRT
<213> ORGANISM: Artificial Sequence
<220> FEATURE:
<223> OTHER INFORMATION: "Description of Artificial Sequence: Synthetic
      polypeptide"
<220> FEATURE:
<221> NAME/KEY: SITE
<222> LOCATION: (1)..(232)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (23)..(23)
<223> OTHER INFORMATION: /replace="K"
<220> FEATURE:
```

<221> NAME/KEY: VARIANT
<222> LOCATION: (82)..(82)
<223> OTHER INFORMATION: /replace="A"
<220> FEATURE:
<221> NAME/KEY: VARIANT
<222> LOCATION: (141)..(141)
<223> OTHER INFORMATION: /replace="E"
<220> FEATURE:
<221> NAME/KEY: VARIANT
<222> LOCATION: (143)..(143)
<223> OTHER INFORMATION: /replace="M"
<220> FEATURE:
<221> NAME/KEY: VARIANT
<222> LOCATION: (232)..(232)
<223> OTHER INFORMATION: /replace=" "

<400> SEQUENCE: 87

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 88
<211> LENGTH: 446
<212> TYPE: PRT
<213> ORGANISM: Artificial Sequence
<220> FEATURE:
<223> OTHER INFORMATION: "Description of Artificial Sequence: Synthetic
polypeptide"

<400> SEQUENCE: 88

```
Gln Val Gln Leu Val Gln Ser Gly Ala Glu Val Glu Lys Pro Gly Ser
1               5                   10                  15

Ser Val Lys Val Ser Cys Lys Ala Ser Gly Tyr Ala Phe Thr Ser Tyr
            20                  25                  30
```

```
Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 89
<211> LENGTH: 446
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 89

```
Gln Val Gln Leu Val Gln Ser Gly Ala Glu Val Glu Gln Pro Gly Ser
1               5                   10                  15

Ser Val Lys Val Ser Cys Glu Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 90
<211> LENGTH: 107
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 90

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105


<210> SEQ ID NO 91
<211> LENGTH: 446
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Gln Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110
```

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 92
<211> LENGTH: 5
<212> TYPE: PRT
<213> ORGANISM: Artificial Sequence
<220> FEATURE:
<223> OTHER INFORMATION: "Description of Artificial Sequence: Synthetic
      peptide"

<400> SEQUENCE: 92

Gly Gly Gly Gly Ser
1               5
```

<210> SEQ ID NO 93
<211> LENGTH: 10
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 93

Gly Gly Gly Gly Ser Gly Gly Gly Gly Ser
1 5 10

<210> SEQ ID NO 94
<211> LENGTH: 15
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 94

Gly Gly Gly Gly Ser Gly Gly Gly Gly Ser Gly Gly Gly Gly Ser
1 5 10 15

<210> SEQ ID NO 95
<211> LENGTH: 20
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 95

Gly Gly Gly Gly Ser Gly Gly Gly Gly Ser Gly Gly Gly Gly Ser Gly
1 5 10 15

Gly Gly Gly Ser
20

<210> SEQ ID NO 96
<211> LENGTH: 25
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 96

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 97
<211> LENGTH: 3
<212> TYPE: PRT
<213> ORGANISM: Artificial Sequence
<220> FEATURE:
<223> OTHER INFORMATION: "Description of Artificial Sequence: Synthetic peptide"

<400> SEQUENCE: 97

Ala Ser Thr
1

<210> SEQ ID NO 98
<211> LENGTH: 6
<212> TYPE: PRT

<213> ORGANISM: Artificial Sequence
<220> FEATURE:
<223> OTHER INFORMATION: "Description of Artificial Sequence: Synthetic
      peptide"

<400> SEQUENCE: 98

Thr Val Ala Ala Pro Ser
1               5

<210> SEQ ID NO 99
<211> LENGTH: 3
<212> TYPE: PRT
<213> ORGANISM: Artificial Sequence
<220> FEATURE:
<223> OTHER INFORMATION: "Description of Artificial Sequence: Synthetic
      peptide"

<400> SEQUENCE: 99

Thr Val Ala
1

<210> SEQ ID NO 100
<211> LENGTH: 7
<212> TYPE: PRT
<213> ORGANISM: Artificial Sequence
<220> FEATURE:
<223> OTHER INFORMATION: "Description of Artificial Sequence: Synthetic
      peptide"

<400> SEQUENCE: 100

Ala Ser Thr Ser Gly Pro Ser
1               5

<210> SEQ ID NO 101
<211> LENGTH: 1344
<212> TYPE: DNA
<213> ORGANISM: Artificial Sequence
<220> FEATURE:
<223> OTHER INFORMATION: "Description of Artificial Sequence: Synthetic
      polynucleotide"

<400> SEQUENCE: 101
caggtgcagc tggtgcagtc tggtgccgag gtcaaaaagc caggctccag cgtgaaggtg     60
agctgcaagg cctctggcta cgctttcacc tcttattgga tgcactgggt gagacaggct    120
cctggacagg gcctggagtg gatgggccag atcaacccaa ccaccggcag aagccagtac    180
aatgagaagt ttaagacccg cgtgaccatc acagccgaca agtccaccag cacagcttat    240
atggagctgt cttccctgag gtccgaggat acagccgtgt actattgcgc tcggtggggc    300
ctgcagcctt tcgcttactg gggccagggc accctggtga cagtgagctc tgcgtcgacc    360
aagggcccat ccgtgtttcc actggctccc tccagcaagt ctacctccgg aggaacagcc    420
gctctgggat gtctggtgaa ggactacttc ccagagcccg tgacagtgtc ctggaacagc    480
ggcgccctga cctccggcgt gcatacattt ccagctgtgc tgcagtcttc cggcctgtac    540
agcctgagct ctgtggtgac cgtgccctcc agctctctgg gcacccagac atatatctgc    600
aacgtgaatc acaagccatc caatacaaag gtggacaaga gggtggagcc caagagctgt    660
gataagaccc atacatgccc accttgtcct gctccagagc tgctgggagg caagagcgtg    720
ttcctgtttc cacccaagcc caaggacacc ctgatgatct ctcggacccc tgaggtgaca    780
tgcgtggtgg tggacgtgtc ccacgaggac cccgaggtga agttcaactg gtacgtggat    840
ggcgtggagg tgcataatgc taagaccaag cctagggagg agcagtacaa cagcacctat    900
cgggtggtgt ctgtgctgac agtgctgcac caggactggc tgaacggcaa ggagtataag 960
tgcaaggtga gcaataaggc cctgcccgct cctatcgaga agaccatctc taaggccaag 1020
ggccagccta gagagccaca ggtgtacaca ctgcctccaa gccgcgacga gctgaccaag 1080
aaccaggtgt ctctgacatg tctggtgaag ggcttctatc cctctgatat cgctgtggag 1140
tgggagtcca atggccagcc tgagaacaat tacaagacca cacccccctgt gctggactct 1200 gatggctcct tctttctgta ttccaagctg accgtggata agagccgctg gcagcagggc 1260
aacgtgttct cctgttctgt gatgcacgaa gcactgcaca accattacac ccagaaaagc 1320
ctgtcactgt cacccggaaa atga 1344

<210> SEQ ID NO 102
<211> LENGTH: 1344
<212> TYPE: DNA
<213> ORGANISM: Artificial Sequence
<220> FEATURE:
<223> OTHER INFORMATION: “Description of Artificial Sequence: Synthetic polynucleotide”

<400> SEQUENCE: 102
caggtgcagc tggtgcagtc tggggctgaa gtcaagaagc caggctccag cgtgaaggtg 60
agctgcaagg cctctggcta cgctttcacc tcctattgga tgcactgggt gagacaggct 120
cctggacagg gcctggagtg gatgggccag atcaacccaa ccacaggccg cagccagtac 180
aatgagaagt ttaagaccca ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gggagccaca ggtgtacaca ctgcctccat ctcgggacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 103
<211> LENGTH: 1344
<212> TYPE: DNA
<213> ORGANISM: Artificial Sequence
<220> FEATURE:

<223> OTHER INFORMATION: "Description of Artificial Sequence: Synthetic polynucleotide"

<400> SEQUENCE: 103

```
caggtgcagc tggtgcagtc cggtgccgag gtcgagaagc caggctccag cgtgaaggtg     60
agctgcaagg cctctggcta cgctttcacc tcctattgga tgcactgggt gagacaggct    120
cctggacagg gcctggagtg gatgggccag atcaacccaa ccacaggcag aagccagtac    180
aatgagaagt ttaagacccg cgtgaccatc acagccgaca agtccaccag cacagcttat    240
atggagctgt cttccctgag gtctgaggat acagccgtgt actattgcgc tcggtggggc    300
ctgcagcctt tcgcttactg gggccagggc accctggtga cagtgagctc tgcgtcgacc    360
aagggcccaa gcgtgtttcc actggctccc tccagcaagt ctacctccgg aggcacagcc    420
gctctgggat gtctggtgaa ggactacttc ccagagcccg tgacagtgtc ctggaacagc    480
ggcgccctga ccagcggagt gcatacattt ccagctgtgc tgcagtcttc cggcctgtac    540
tctctgagct ctgtggtgac cgtgccctcc agctctctgg gcacccagac atatatctgc    600
aacgtgaatc acaagccaag caatacaaag gtggacaaga gggtggagcc caagtcttgt    660
gataagaccc atacatgccc accttgtcct gctccagagc tgctgggcgg caagtccgtg    720
ttcctgtttc cacccaagcc caaggacacc ctgatgatct cccggacccc tgaggtgaca    780
tgcgtggtgg tggacgtgag ccacgaggac cccgaggtga agttcaactg gtacgtggat    840
ggcgtggagg tgcataatgc taagaccaag cctagggagg agcagtacaa ctctacctat    900
cgggtggtgt ccgtgctgac agtgctgcac caggactggc tgaacggcaa ggagtataag    960
tgcaaggtgt ctaataaggc cctgcccgct cctatcgaga agaccatctc caaggccaag   1020
ggccagccta gagagccaca ggtgtacaca ctgcctccat ctcgcgacga gctgaccaag   1080
aaccaggtgt ccctgacatg tctggtgaag ggcttctatc cctccgatat cgctgtggag   1140
tgggagagca atggccagcc tgagaacaat tacaagacca cacccccctgt gctggactct   1200
gatggctcct tctttctgta tagcaagctg accgtggata agtctcgctg gcagcagggc   1260
aacgtgttct cctgttctgt gatgcacgaa gcactgcaca accattacac tcagaagtca   1320
ctgtcactgt ctcctgggaa atga                                          1344
```

<210> SEQ ID NO 104
<211> LENGTH: 1344
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 104

```
caggtgcagc tggtgcagtc cggtgccgag gtcgagcagc caggctccag cgtgaaggtg     60
agctgcgagg cctctggcta cgctttcacc tcctattgga tgcactgggt gagacaggct    120
cctggacagg gcctggagtg gatgggccag atcaacccaa ccacaggcag aagccagtac    180
aatgagaagt ttaagacccg cgtgaccatc acagccgaca agtccaccag cacagcttat    240
atggagctgt cttccctgag gtctgaggat acagccgtgt actattgcgc tcggtggggc    300
ctgcagcctt tcgcttactg gggccagggc accctggtga cagtgagctc tgcgtcgacc    360
aagggcccaa gcgtgtttcc actggctccc tccagcaagt ctacctccgg aggcacagcc    420
gctctgggat gtctggtgaa ggactacttc ccagagcccg tgacagtgtc ctggaacagc    480
ggcgccctga ccagcggagt gcatacattt ccagctgtgc tgcagtcttc cggcctgtac    540
```

tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct cccggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gagagccaca ggtgtacaca ctgcctccat ctcgcgacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcgctg gcagcagggc 1260
aacgtgttct cctgttctgt gatgcacgaa gcactgcaca accattacac tcagaagtca 1320
ctgtcactgt ctcctgggaa atga 1344

<210> SEQ ID NO 105
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 105
gacattcaga tgactcagtc tccctccttc ctgtcagcct ctgtgggcga cagggtgacc 60
atcacatgca aggcttccca ggatgtgagc accgccgtgg cttggtacca gcagaagcca 120
ggcaaggccc cccagctgct gatctattcc gcctcttacc agtataccgg agtgccatcc 180
cagttctccg gcagcggctc tggaacagac tttaccctga caatctccag cctgcagcct 240
gaggatttcg ccacctacta ttgccagcag cactacagca ccccatggac atttggcggc 300
ggcaccaagg tggagatcaa gagaacagtg gccgctccca gcgtgttcat ctttcccccct 360 tctgacgagc agctgaagtc tggcacagct tccgtggtgt gcctgctgaa caatttctac 420
cctcgcgagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgactacga gaagcataag gtgtatgctt gtgaagtcac ccaccagggg 600
ctgagttcac cagtcacaaa atctttcaat agaggggaat gttga 645

<210> SEQ ID NO 106
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 106
gacattcaga tgactcagtc tccctccttc ctgtcagcct ctgtgggcga cagggtgacc 60
atcacatgca aggcttccca ggatgtgagc accgccgtgg cttggtacca gcagaagcca 120
ggcaaggccc ccgagctgct gatctattcc gcctcttaca ggtataccgg agtgccatcc 180
cggttctccg gcagcggctc tggaacagac tttaccctga caatctccag cctgcagcct 240
gaggatttcg ccacctacta ttgccagcag cactacagca ccccatggac atttggcggc 300
ggcaccaagg tggagatcaa gagaacagtg gccgctccca gcgtgttcat ctttccccct 360
tctgacgagc agctgaagtc tggcacagct tccgtggtgt gcctgctgaa caatttctac 420
cctcgcgagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgactacga gaagcataag gtgtatgctt gtgaagtcac ccaccagggg 600
ctgagttcac cagtcacaaa atctttcaat agaggggaat gttga 645

<210> SEQ ID NO 107
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 107
gacatccaga tgacccagtc cccctccttc ctgtctgcct ccgtgggcga cagagtgacc 60
atcacctgta aggcttccca ggatgtgagc acagccgtgg cttggtacca gcagaagcca 120
ggcaaggccc ccaagctgct gatctattcc gcctcttaca ggtataccgg cgtgccctct 180
cggttctccg gcagcggctc tggcacagac tttaccctga caatctccag cctgcagcct 240
gaggatttcg ccacctacta ttgccagcag cactactcca ccccatggac atttggcggc 300
ggcaccaagg tggagatcaa gaggacagtg gccgctccca gcgtgttcat ctttccccct 360
tctgacgagc agctgaagtc tggcaccgct tccgtggtgt gcctgctgaa caatttctac 420
cctcgggagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgattacga gaagcacaag gtgtatgctt gcgaggtgac ccatcagggc 600
ctgagctctc ccgtgacaaa gagctttaac cgcggcgagt gttga 645

<210> SEQ ID NO 108
<211> LENGTH: 1344
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 108
caggtgcagc tggtgcagtc cggtgccgag gtccagcagc caggctccag cgtgaaggtg 60
agctgcaagg cctctggcta cgctttcacc tcctattgga tgcactgggt gagacaggct 120
cctggacagg gcctggagtg gatgggccag atcaacccaa ccacaggcag aagccagtac 180
aatgagaagt ttaagacccg cgtgaccatc acagccgaca agtccaccag cacagcttat 240
atggagctgt cttccctgag gtctgaggat acagccgtgt actattgcgc tcggtggggc 300
ctgcagcctt tcgcttactg gggccagggc accctggtga cagtgagctc tgcgtcgacc 360
aagggcccaa gcgtgtttcc actggctccc tccagcaagt ctacctccgg aggcacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600

```
aacgtgaatc acaagccaag caatacaaag gtggacaaga gggtggagcc caagtcttgt    660

gataagaccc atacatgccc accttgtcct gctccagagc tgctgggcgg caagtccgtg    720

ttcctgtttc cacccaagcc caaggacacc ctgatgatct cccggacccc tgaggtgaca    780

tgcgtggtgg tggacgtgag ccacgaggac cccgaggtga agttcaactg gtacgtggat    840

ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gagagccaca ggtgtacaca ctgcctccat ctcgcgacga gctgaccaag   1080

aaccaggtgt ccctgacatg tctggtgaag ggcttctatc cctccgatat cgctgtggag   1140

tgggagagca atggccagcc tgagaacaat tacaagacca cacccccctgt gctggactct   1200

gatggctcct tctttctgta tagcaagctg accgtggata agtctcgctg gcagcagggc   1260

aacgtgttct cctgttctgt gatgcacgaa gcactgcaca accattacac tcagaagtca   1320

ctgtcactgt ctcctgggaa atga                                          1344
```

<210> SEQ ID NO 109
<211> LENGTH: 1344
<212> TYPE: DNA
<213> ORGANISM: Artificial Sequence
<220> FEATURE:
<223> OTHER INFORMATION: “Description of Artificial Sequence: Synthetic polynucleotide”

<400> SEQUENCE: 109

```
caggtgcagc tggtgcagtc cggtgccgag gtccagcagc caggctccag cgtgaaggtg     60

agctgccagg cctctggcta cgctttcacc tcctattgga tgcactgggt gagacaggct    120

cctggacagg gcctggagtg gatgggccag atcaacccaa ccacaggcag aagccagtac    180

aatgagaagt ttaagacccg cgtgaccatc acagccgaca agtccaccag cacagcttat    240

atggagctgt cttccctgag gtctgaggat acagccgtgt actattgcgc tcggtggggc    300

ctgcagcctt tcgcttactg gggccagggc accctggtga cagtgagctc tgcgtcgacc    360

aagggcccaa gcgtgtttcc actggctccc tccagcaagt ctacctccgg aggcacagcc    420

gctctgggat gtctggtgaa ggactacttc ccagagcccg tgacagtgtc ctggaacagc    480

ggcgccctga ccagcggagt gcatacattt ccagctgtgc tgcagtcttc cggcctgtac    540

tctctgagct ctgtggtgac cgtgccctcc agctctctgg gcacccagac atatatctgc    600

aacgtgaatc acaagccaag caatacaaag gtggacaaga gggtggagcc caagtcttgt    660

gataagaccc atacatgccc accttgtcct gctccagagc tgctgggcgg caagtccgtg    720

ttcctgtttc cacccaagcc caaggacacc ctgatgatct cccggacccc tgaggtgaca    780

tgcgtggtgg tggacgtgag ccacgaggac cccgaggtga agttcaactg gtacgtggat    840

ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gagagccaca ggtgtacaca ctgcctccat ctcgcgacga gctgaccaag   1080

aaccaggtgt ccctgacatg tctggtgaag ggcttctatc cctccgatat cgctgtggag   1140

tgggagagca atggccagcc tgagaacaat tacaagacca cacccccctgt gctggactct   1200

gatggctcct tctttctgta tagcaagctg accgtggata agtctcgctg gcagcagggc   1260
```

aacgtgttct cctgttctgt gatgcacgaa gcactgcaca accattacac tcagaagtca 1320
ctgtcactgt ctcctgggaa atga 1344

<210> SEQ ID NO 110
<211> LENGTH: 1344
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 110
caggtgcagc tggtgcagtc cggtgccgag gtcgtgaagc caggctccag cgtgtccgtg 60
agctgcgccg cctctggcta cgctttcacc tcctattgga tgcactgggt gagacaggct 120
cctggacagg gcctggagtg gatgggccag atcaacccaa ccacaggcag aagccagtac 180
aatgagaagt ttaagacccg cgtgaccatc acagccgaca agtccaccag cacagcttat 240
atggagctgt cttccctgag gtctgaggat acagccgtgt actattgcgc tcggtggggc 300
ctgcagcctt tcgcttactg gggccagggc accctggtga cagtgagctc tgcgtcgacc 360
aagggcccaa gcgtgtttcc actggctccc tccagcaagt ctacctccgg aggcacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct cccggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gagagccaca ggtgtacaca ctgcctccat ctcgcgacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcgctg gcagcagggc 1260
aacgtgttct cctgttctgt gatgcacgaa gcactgcaca accattacac tcagaagtca 1320
ctgtcactgt ctcctgggaa atga 1344

<210> SEQ ID NO 111
<211> LENGTH: 1344
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 111
caggtgcagc tggtgcagtc cggtgccgag gtcaagaagc caggctccag cgtgaaggtg 60
agctgcgagg cctctggcta cgctttcacc tcctattgga tgcactgggt gagacaggct 120
cctggacagg gcctggagtg gatgggccag atcaacccaa ccacaggcag aagccagtac 180
aatgagaagt ttaagacccg cgtgaccatc acagccgaca agtccaccag cacagcttat 240
atggagctgt cttccctgag gtctgaggat acagccgtgt actattgcgc tcggtggggc 300
ctgcagcctt tcgcttactg gggccagggc accctggtga cagtgagctc tgcgtcgacc 360
aagggcccaa gcgtgtttcc actggctccc tccagcaagt ctacctccgg aggcacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct cccggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gagagccaca ggtgtacaca ctgcctccat ctcgcgacga gctgaccaag 1080
aaccaggtgt ccctgacatg tctggtgaag ggcttctatc cctccgatat cgctgtggag 1140
tgggagagca atggccagcc tgagaacaat tacaagacca cacccccgtgt gctggactct 1200 gatggctcct tctttctgta tagcaagctg accgtggata agtctcgctg gcagcagggc 1260
aacgtgttct cctgttctgt gatgcacgaa gcactgcaca accattacac tcagaagtca 1320
ctgtcactgt ctcctgggaa atga 1344

<210> SEQ ID NO 112
<211> LENGTH: 1344
<212> TYPE: DNA
<213> ORGANISM: Artificial Sequence
<220> FEATURE:
<223> OTHER INFORMATION: "Description of Artificial Sequence: Synthetic
polynucleotide"

<400> SEQUENCE: 112
caggtgcagc tggtgcagtc tggggctgaa gtcaagaagc caggctccag cgtgaaggtg 60
agctgcaagg cctctggcta cgctttcacc tcctattgga tgcactgggt gcagcaggct 120
cctggacagg gcctggagtg gatgggccag atcaacccaa ccacaggccg cagccagtac 180
aatgagcagt ttaagaccca ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840

```
ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gggagccaca ggtgtacaca ctgcctccat ctcgggacga gctgaccaag   1080

aaccaggtgt ccctgacatg tctggtgaag ggcttctatc cctccgatat cgctgtggag   1140

tgggagagca atggccagcc tgagaacaat tacaagacca cacccccctgt gctggactct   1200

gatggctcct tctttctgta tagcaagctg accgtggata agtctcggtg gcagcagggc   1260

aacgtgttct cctgttctgt gatgcacgaa gcactgcaca accactacac tcagaagtca   1320

ctgtcactgt ctcctggcaa atga                                          1344
```

<210> SEQ ID NO 113
<211> LENGTH: 1344
<212> TYPE: DNA
<213> ORGANISM: Artificial Sequence
<220> FEATURE:
<223> OTHER INFORMATION: “Description of Artificial Sequence: Synthetic polynucleotide”

<400> SEQUENCE: 113

```
caggtgcagc tggtgcagtc tggggctgaa gtcaagaagc caggctccag cgtgaaggtg     60

agctgcaagg cctctggcta cgctttcacc tcctattgga tgcactgggt gagacaggct    120

cctggacagg gcctggagtg gatgggccag atcaacccaa ccacaggccg cagccagtac    180

aatgagcagt ttaagaccga ggtgaccatc acagccgaca agtccaccag cacagcttat    240

atggagctgt cttccctgag atctgaggat acagccgtgt actattgcgc tcgctggggc    300

ctgcagcctt tcgcttactg gggccagggc accctggtga cagtgagctc tgcgtcgacc    360

aagggcccaa gcgtgtttcc actggctccc tccagcaagt ctacctccgg aggaacagcc    420

gctctgggat gtctggtgaa ggactacttc ccagagcccg tgacagtgtc ctggaacagc    480

ggcgccctga ccagcggagt gcatacattt ccagctgtgc tgcagtcttc cggcctgtac    540

tctctgagct ctgtggtgac cgtgccctcc agctctctgg gcacccagac atatatctgc    600

aacgtgaatc acaagccaag caatacaaag gtggacaaga gggtggagcc caagtcttgt    660

gataagaccc atacatgccc accttgtcct gctccagagc tgctgggcgg caagtccgtg    720

ttcctgtttc cacccaagcc caaggacacc ctgatgatct ccaggacccc tgaggtgaca    780

tgcgtggtgg tggacgtgag ccacgaggac cccgaggtga agttcaactg gtacgtggat    840

ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gggagccaca ggtgtacaca ctgcctccat ctcgggacga gctgaccaag   1080

aaccaggtgt ccctgacatg tctggtgaag ggcttctatc cctccgatat cgctgtggag   1140

tgggagagca atggccagcc tgagaacaat tacaagacca cacccccctgt gctggactct   1200

gatggctcct tctttctgta tagcaagctg accgtggata agtctcggtg gcagcagggc   1260

aacgtgttct cctgttctgt gatgcacgaa gcactgcaca accactacac tcagaagtca   1320

ctgtcactgt ctcctggcaa atga                                          1344
```

<210> SEQ ID NO 114
<211> LENGTH: 1344
<212> TYPE: DNA

<213> ORGANISM: Artificial Sequence
<220> FEATURE:
<223> OTHER INFORMATION: “Description of Artificial Sequence: Synthetic
polynucleotide”

<400> SEQUENCE: 114
caggtgcagc tggtgcagtc tggggctgaa gtcaagaagc caggctccag cgtgaaggtg 60
agctgcaagg cctctggcta cgctttcacc tcctattgga tgcactgggt gagacaggct 120
cctggacagg gcctggagtg gatgggccag atcaacccaa ccacaggccg cagccagtac 180
aatgagaagt ttaagaccga ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gggagccaca ggtgtacaca ctgcctccat ctcgggacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 115
<211> LENGTH: 1344
<212> TYPE: DNA
<213> ORGANISM: Artificial Sequence
<220> FEATURE:
<223> OTHER INFORMATION: “Description of Artificial Sequence: Synthetic
polynucleotide”

<400> SEQUENCE: 115
caggtgcagc tggtgcagtc tggggctgaa gtcaagaagc caggctccag cgtgaaggtg 60
agctgcaagg cctctggcta cgctttcacc tcctattgga tgcactgggt gagacaggct 120
cctggacagg gcctggagtg gatgggccag atcaacccaa ccacaggcga gagccagtac 180
aatgagaagt ttaagaccag ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480

```
ggcgccctga ccagcggagt gcatacattt ccagctgtgc tgcagtcttc cggcctgtac    540

tctctgagct ctgtggtgac cgtgccctcc agctctctgg gcacccagac atatatctgc    600

aacgtgaatc acaagccaag caatacaaag gtggacaaga gggtggagcc caagtcttgt    660

gataagaccc atacatgccc accttgtcct gctccagagc tgctgggcgg caagtccgtg    720

ttcctgtttc cacccaagcc caaggacacc ctgatgatct ccaggacccc tgaggtgaca    780

tgcgtggtgg tggacgtgag ccacgaggac cccgaggtga agttcaactg gtacgtggat    840

ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gggagccaca ggtgtacaca ctgcctccat ctcgggacga gctgaccaag   1080

aaccaggtgt ccctgacatg tctggtgaag ggcttctatc cctccgatat cgctgtggag   1140

tgggagagca atggccagcc tgagaacaat tacaagacca cacccccctgt gctggactct   1200

gatggctcct tctttctgta tagcaagctg accgtggata agtctcggtg gcagcagggc   1260

aacgtgttct cctgttctgt gatgcacgaa gcactgcaca accactacac tcagaagtca   1320

ctgtcactgt ctcctggcaa atga                                          1344
```

<210> SEQ ID NO 116
<211> LENGTH: 1344
<212> TYPE: DNA
<213> ORGANISM: Artificial Sequence
<220> FEATURE:
<223> OTHER INFORMATION: “Description of Artificial Sequence: Synthetic
      polynucleotide”

<400> SEQUENCE: 116

```
caggtgcagc tggtgcagtc tggggctgaa gtcaagaagc caggctccag cgtgaaggtg     60

agctgcaagg cctctggcta cgctttcacc tcctattgga tgcactgggt gagacaggct    120

cctggacagg gcctggagtg gatgggccag atcaacccaa ccacaggcga gagccagtac    180

aatgagaagt ttaagaccag ggtgaccatc acagccgacc agtccaccag cacagcttat    240

atggagctgt cttccctgag atctgaggat acagccgtgt actattgcgc tcgctggggc    300

ctgcagcctt tcgcttactg gggccagggc accctggtga cagtgagctc tgcgtcgacc    360

aagggcccaa gcgtgtttcc actggctccc tccagcaagt ctacctccgg aggaacagcc    420

gctctgggat gtctggtgaa ggactacttc ccagagcccg tgacagtgtc ctggaacagc    480

ggcgccctga ccagcggagt gcatacattt ccagctgtgc tgcagtcttc cggcctgtac    540

tctctgagct ctgtggtgac cgtgccctcc agctctctgg gcacccagac atatatctgc    600

aacgtgaatc acaagccaag caatacaaag gtggacaaga gggtggagcc caagtcttgt    660

gataagaccc atacatgccc accttgtcct gctccagagc tgctgggcgg caagtccgtg    720

ttcctgtttc cacccaagcc caaggacacc ctgatgatct ccaggacccc tgaggtgaca    780

tgcgtggtgg tggacgtgag ccacgaggac cccgaggtga agttcaactg gtacgtggat    840

ggcgtggagg tgcataatgc taagaccaag cctagggagg agcagtacaa ctctacctat    900

cgggtggtgt ccgtgctgac agtgctgcac caggactggc tgaacggcaa ggagtataag    960

tgcaaggtgt ctaataaggc cctgcccgct cctatcgaga agaccatctc caaggccaag   1020

ggccagccta gggagccaca ggtgtacaca ctgcctccat ctcgggacga gctgaccaag   1080

aaccaggtgt ccctgacatg tctggtgaag ggcttctatc cctccgatat cgctgtggag   1140
```

tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 117
<211> LENGTH: 1344
<212> TYPE: DNA
<213> ORGANISM: Artificial Sequence
<220> FEATURE:
<223> OTHER INFORMATION: “Description of Artificial Sequence: Synthetic polynucleotide”

<400> SEQUENCE: 117
caggtgcagc tggtgcagtc tggggctgaa gtcaagaagc caggctccag cgtgaaggtg 60
agctgcaagg cctctggcta cgctttcacc tcctattgga tgcactgggt gagacaggct 120
cctggacagg gcctgaagtg gatgggccag atcaacccaa ccacaggccg cagccagtac 180
aataagaagt ttaagaccag ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gggagccaca ggtgtacaca ctgcctccat ctcgggacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 118
<211> LENGTH: 232
<212> TYPE: PRT
<213> ORGANISM: Artificial Sequence
<220> FEATURE:
<223> OTHER INFORMATION: “Description of Artificial Sequence: Synthetic polypeptide”
<220> FEATURE:
<221> NAME/KEY: MOD_RES
<222> LOCATION: (23)..(23)
<223> OTHER INFORMATION: Any amino acid
<220> FEATURE:

<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (143)..(143)
<223> OTHER INFORMATION: Any amino acid
<220> FEATURE:
<221> NAME/KEY: MOD_RES
<222> LOCATION: (232)..(232)
<223> OTHER INFORMATION: Any amino acid

<400> SEQUENCE: 118

Glu Pro Lys Ser Cys Asp Lys Thr His Thr Cys Pro Pro Cys Pro Ala
1 5 10 15

Pro Glu Leu Leu Gly Gly Xaa Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Xaa Glu Xaa Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Xaa
225 230

<210> SEQ ID NO 119
<211> LENGTH: 232
<212> TYPE: PRT
<213> ORGANISM: Artificial Sequence
<220> FEATURE:
<223> OTHER INFORMATION: "Description of Artificial Sequence: Synthetic
polypeptide"
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (143)..(143)
<223> OTHER INFORMATION: Any amino acid
<220> FEATURE:
<221> NAME/KEY: MOD_RES
<222> LOCATION: (232)..(232)
<223> OTHER INFORMATION: Any amino acid

<400> SEQUENCE: 119

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Xaa Glu Xaa Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230
```

<210> SEQ ID NO 120
<211> LENGTH: 232
<212> TYPE: PRT
<213> ORGANISM: Artificial Sequence
<220> FEATURE:
<223> OTHER INFORMATION: "Description of Artificial Sequence: Synthetic polypeptide"
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (82)..(82)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (143)..(143)
<223> OTHER INFORMATION: Any amino acid
<220> FEATURE:
<221> NAME/KEY: MOD_RES
<222> LOCATION: (232)..(232)
<223> OTHER INFORMATION: Any amino acid

<400> SEQUENCE: 120

```
Glu Pro Lys Ser Cys Asp Lys Thr His Thr Cys Pro Pro Cys Pro Ala
1               5                   10                  15

Pro Glu Leu Leu Gly Gly Xaa Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Xaa Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Xaa Glu Xaa Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230
```

<210> SEQ ID NO 121
<211> LENGTH: 1344
<212> TYPE: DNA
<213> ORGANISM: Artificial Sequence
<220> FEATURE:
<223> OTHER INFORMATION: “Description of Artificial Sequence: Synthetic polynucleotide”

<400> SEQUENCE: 121

```
caggtgcagc tggtgcagtc tggggctgaa gtcaagaagc caggctccag cgtgaaggtg     60

agctgcaagg cctctggcta cgctttcacc tcctattgga tgcactgggt gagacaggct    120

cctggacagg gcctggagtg gatgggccag atcaacccaa ccacaggccg cagccagtac    180

aatgagaagt ttaagaccag ggtgaccatc acagccgaca cctccaccag cacagcttat    240

atggagctgt cttccctgag atctgaggat acagccgtgt actattgcgc tcgctggggc    300

ctgcagcctt tcgcttactg gggccagggc accctggtga cagtgagctc tgcgtcgacc    360

aagggcccaa gcgtgtttcc actggctccc tccagcaagt ctacctccgg aggaacagcc    420

gctctgggat gtctggtgaa ggactacttc ccagagcccg tgacagtgtc ctggaacagc    480

ggcgccctga ccagcggagt gcatacattt ccagctgtgc tgcagtcttc cggcctgtac    540

tctctgagct ctgtggtgac cgtgccctcc agctctctgg gcacccagac atatatctgc    600
```

aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gggagccaca ggtgtacaca ctgcctccat ctcgggacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 122
<211> LENGTH: 1344
<212> TYPE: DNA
<213> ORGANISM: Artificial Sequence
<220> FEATURE:
<223> OTHER INFORMATION: "Description of Artificial Sequence: Synthetic
      polynucleotide"

<400> SEQUENCE: 122
caggtgcagc tggtgcagtc tggggctgaa gtcaagaagc caggctccag cgtgaaggtg 60
agctgcaagg cctctggcta cgctttcacc tcctattgga tgcactgggt gagacaggct 120
cctggacagg gcctggagtg gatgggccag atcaacccaa ccacaggccg cagccagtac 180
aatgagcagt ttaagaccag ggtgaccatc acagccgaca agtccaccag cacagcttat 240
atggagctgt cttccctgag atctgaggat acagccgtgt actattgcgc tcgctggggc 300
ctgcagcctt tcgcttactg gggccagggc accctggtga cagtgagctc tgcgtcgacc 360
aagggcccaa gcgtgtttcc actggctccc tccagcaagt ctacctccgg aggaacagcc 420
gctctgggat gtctggtgaa ggactacttc ccagagcccg tgacagtgtc ctggaacagc 480
ggcgccctga ccagcggagt gcatacattt ccagctgtgc tgcagtcttc cggcctgtac 540
tctctgagct ctgtggtgac cgtgccctcc agctctctgg gcacccagac atatatctgc 600
aacgtgaatc acaagccaag caatacaaag gtggacaaga gggtggagcc caagtcttgt 660
gataagaccc atacatgccc accttgtcct gctccagagc tgctgggcgg caagtccgtg 720
ttcctgtttc cacccaagcc caaggacacc ctgatgatct ccaggacccc tgaggtgaca 780
tgcgtggtgg tggacgtgag ccacgaggac cccgaggtga agttcaactg gtacgtggat 840
ggcgtggagg tgcataatgc taagaccaag cctagggagg agcagtacaa ctctacctat 900
cgggtggtgt ccgtgctgac agtgctgcac caggactggc tgaacggcaa ggagtataag 960
tgcaaggtgt ctaataaggc cctgcccgct cctatcgaga agaccatctc caaggccaag 1020
ggccagccta gggagccaca ggtgtacaca ctgcctccat ctcgggacga gctgaccaag 1080
aaccaggtgt ccctgacatg tctggtgaag ggcttctatc cctccgatat cgctgtggag 1140
tgggagagca atggccagcc tgagaacaat tacaagacca cacccccctgt gctggactct 1200 gatggctcct tctttctgta tagcaagctg accgtggata agtctcggtg gcagcagggc 1260
aacgtgttct cctgttctgt gatgcacgaa gcactgcaca accactacac tcagaagtca 1320
ctgtcactgt ctcctggcaa atga 1344

<210> SEQ ID NO 123
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 123
gacattcaga tgactcagtc tccctccttc ctgtcagcct ctgtgggcga cagggtgacc 60
atcacatgca aggcttccca ggatgtgagc accgccgtgg cttggtacca gcagaagcca 120
ggcaaggccc cccagctgct gatctattcc gcctcttaca ggtataccgg agtgccatcc 180
cggttctccg gcagcggctc tggaacagac tttaccctga caatctccag cctgcagcct 240
gaggatttcg ccacctacta ttgccagcag cactacagca ccccatggac atttggcggc 300
ggcaccaagg tggagatcaa gagaacagtg gccgctccca gcgtgttcat ctttccccct 360
tctgacgagc agctgaagtc tggcacagct tccgtggtgt gcctgctgaa caatttctac 420
cctcgcgagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgactacga gaagcataag gtgtatgctt gtgaagtcac ccaccagggg 600
ctgagttcac cagtcacaaa atctttcaat agaggggaat gttga 645

<210> SEQ ID NO 124
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 124
gacattcaga tgactcagtc tccctccttc ctgtcagcct ctgtgggcga cagggtgacc 60
atcacatgca aggcttccca ggatgtgagc accgccgtgg cttggtacca gcagaagcca 120
ggcaaggccc ccaagctgct gatctattcc gcctcttaca ggtataccgg agtgccatcc 180
cagttctccg gcagcggctc tggaacagac tttaccctga caatctccag cctgcagcct 240
gaggatttcg ccacctacta ttgccagcag cactacagca ccccatggac atttggcggc 300
ggcaccaagg tggagatcaa gagaacagtg gccgctccca gcgtgttcat ctttccccct 360
tctgacgagc agctgaagtc tggcacagct tccgtggtgt gcctgctgaa caatttctac 420
cctcgcgagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgactacga gaagcataag gtgtatgctt gtgaagtcac ccaccagggg 600
ctgagttcac cagtcacaaa atctttcaat agaggggaat gttga 645

<210> SEQ ID NO 125
<211> LENGTH: 645
<212> TYPE: DNA
<213> ORGANISM: Artificial Sequence
<220> FEATURE:
<223> OTHER INFORMATION: "Description of Artificial Sequence: Synthetic polynucleotide"

<400> SEQUENCE: 125
gacattcaga tgactcagtc tccctccttc ctgtcagcct ctgtgggcga cagggtgacc 60
atcacatgca aggcttccca ggatgtgagc accgccgtgg cttggtacca gcagaagcca 120
ggcaaggccc ccaagctgct gatctattcc gcctcttaca ggtataccgg agtgccatcc 180
cggttctccg gcagcggctc tggaacagac tttaccctga caatctccag cctgcagcct 240
gaggatttcg ccacctacta ttgccagcag cactacagca ccccatggac atttggcggc 300
ggcaccaagg tggagatcca gcagacagtg gccgctccca gcgtgttcat ctttcccccct 360 tctgacgagc agctgaagtc tggcacagct tccgtggtgt gcctgctgaa caatttctac 420
cctcgcgagg ccaaggtgca gtggaaggtg gataacgctc tgcagtccgg caatagccag 480
gagtctgtga ccgagcagga ctccaaggat agcacatatt ctctgtcttc caccctgaca 540
ctgtccaagg ccgactacga gaagcataag gtgtatgctt gtgaagtcac ccaccagggg 600
ctgagttcac cagtcacaaa atctttcaat agaggggaat gttga 645

<210> SEQ ID NO 126
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 126

Gln Val Gln Leu Gln Gln Ser Gly Ala Glu Leu Ala Lys Pro Gly Ser
1 5 10 15

Ser Val Lys Met Ser Cys Lys Ala Ser Gly Tyr Ala Phe Thr Ser Tyr
20 25 30

Trp Met His Trp Ile Lys Gln Arg Pro Gly Gln Gly Leu Glu Trp Ile
35 40 45

Gly Phe Ile Asn Pro Thr Thr Gly Tyr Ser Glu Tyr Asn Gln Lys Phe
50 55 60

Lys Asp Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Ala Arg Trp Gly Leu Pro Pro Phe Ala Tyr Trp Gly Gln Gly Thr Leu
100 105 110

Val Thr Val Ser Ala
115

<210> SEQ ID NO 127
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 127

Gln Val Gln Leu Gln Gln Ser Gly Ala Glu Leu Ala Lys Pro Gly Ala
1 5 10 15

Ser Val Lys Met Ser Cys Lys Thr Ser Gly Tyr Ser Phe Thr Ser Tyr
20 25 30

Trp Met His Trp Ile Lys Gln Arg Pro Gly Gln Gly Leu Glu Trp Ile
35 40 45

Gly Phe Ile Asn Pro Thr Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Ser Ser Glu Asp Ser Ala Val Tyr Tyr Cys
                85                  90                  95

Ser Arg Trp Gly Leu Pro Pro Phe Ala Tyr Trp Gly Gln Gly Thr Leu
            100                 105                 110

Val Thr Val Ser Ala
        115

<210> SEQ ID NO 128
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 128

Gln Val Gln Leu Gln Gln Ser Gly Ala Glu Leu Thr Lys Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ser Ile Asn Pro Ser Thr Gly Tyr Thr Glu Asp Asn Gln Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Leu Pro Pro Phe Ala Tyr Trp Gly Gln Gly Thr Leu
            100                 105                 110

Val Thr Val Ser Ala
        115

<210> SEQ ID NO 129
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 129

Gln Val Gln Leu Gln Gln Ser Gly Ala Glu Arg Ala Lys Pro Gly Ala
1               5                   10                  15

Ser Val Lys Met Ser Cys Lys Ala Ser Gly Tyr Ser Phe Thr Ser Tyr
            20                  25                  30

Trp Met His Trp Ile Lys Gln Arg Pro Gly Gln Gly Leu Glu Trp Ile
        35                  40                  45

Gly Phe Ile Asn Pro Asn Thr Gly His Thr Asp Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

```
Ser Arg Trp Gly Leu Pro Pro Phe Ala Tyr Trp Gly Gln Gly Thr Leu
            100                 105                 110

Val Thr Val Ser Ala
        115


<210> SEQ ID NO 130
<211> LENGTH: 117
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 130

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Ser Ala Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Asp Pro Arg Pro Phe Ala Tyr Trp Gly Gln Gly Thr Leu
            100                 105                 110

Val Thr Val Ser Ala
        115


<210> SEQ ID NO 131
<211> LENGTH: 117
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 131

Gln Val Gln Leu Gln Gln Ser Gly Ala Glu Leu Ala Lys Pro Gly Thr
1               5                   10                  15

Ser Val Lys Met Ser Cys Lys Ala Ser Gly Tyr Ser Phe Thr Ser Tyr
            20                  25                  30

Trp Val His Trp Val Lys Glu Arg Pro Gly Gln Gly Leu Glu Trp Ile
        35                  40                  45

Gly His Thr Asn Pro Asn Thr Gly Tyr Thr Glu Tyr Asn Gln Lys Phe
    50                  55                  60

Lys Asp Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Asp Pro Arg Pro Phe Ala Tyr Trp Gly Gln Gly Thr Leu
            100                 105                 110

Val Thr Val Ser Ala
        115


<210> SEQ ID NO 132
<211> LENGTH: 117
```

<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 132

Glu Val Gln Leu Gln Gln Ser Gly Thr Val Leu Ala Arg Pro Gly Ala
1               5                   10                  15

Ser Val Lys Met Ser Cys Arg Ala Ser Gly Tyr Ser Phe Ser Ser Tyr
            20                  25                  30

Trp Met His Trp Val Lys Gln Arg Pro Gly Gln Gly Leu Glu Trp Ile
        35                  40                  45

Gly Ser Ile Asn Pro Gly Asn Ser Asp Ala Phe Tyr Asn Gln Gln Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Trp Gly Leu Pro Pro Phe Ala Tyr Trp Gly Gln Gly Thr Leu
            100                 105                 110

Val Thr Val Ser Ala
        115

<210> SEQ ID NO 133
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 133

Glu Val Gln Leu Gln Gln Ser Gly Thr Val Leu Ala Gly Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Asp Leu Glu Trp Ile
        35                  40                  45

Gly Thr Ile Asn Pro Gly Lys Gly Asp Ser Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Trp Gly Leu Pro Pro Phe Ala Tyr Trp Gly Gln Gly Thr Leu
            100                 105                 110

Val Thr Val Ser Ala
        115

<210> SEQ ID NO 134
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 134

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Gln Ile Asn Pro Ser Asn Gly Arg Thr Gln Tyr Asn Glu Lys Phe
    50                  55                  60

Lys Ser Met Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 135
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 135

Gln Val Gln Leu Gln Gln Pro Gly Ala Glu Leu Val Lys Pro Gly Ala
1               5                   10                  15

Ser Val Arg Leu Ser Cys Glu Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Gln Ile Asn Pro Ser Asn Gly Arg Thr Gln Tyr Asn Glu Lys Phe
    50                  55                  60

Lys Ser Met Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 136
<211> LENGTH: 117
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 136

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Ala Phe Thr Ser Tyr
            20                  25                  30

```
Trp Met His Trp Val Lys Gln Arg Pro Gly Gln Gly Leu Glu Trp Ile
        35                  40                  45

Gly Gln Ile Asn Pro Ser Asn Gly Arg Ser Gln Tyr Asn Glu Lys Phe
    50                  55                  60

Lys Thr Met Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115


<210> SEQ ID NO 137
<211> LENGTH: 107
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 137

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105


<210> SEQ ID NO 138
<211> LENGTH: 107
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 138

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95
```

Thr Phe Gly Gly Gly Thr Lys Leu Glu Ile Lys
100 105

<210> SEQ ID NO 139
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 139

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Val Tyr Tyr Cys His Gln His Tyr Ser Thr Pro Trp
85 90 95

Thr Phe Gly Gly Gly Thr Lys Leu Glu Ile Lys
100 105

<210> SEQ ID NO 140
<211> LENGTH: 107
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 140

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Val Tyr Tyr Cys Leu Gln His Tyr Thr Thr Pro Trp
85 90 95

Thr Phe Gly Gly Gly Thr Lys Leu Glu Ile Lys
100 105

<210> SEQ ID NO 141
<211> LENGTH: 231
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 141

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Ala Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 142
<211> LENGTH: 232
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 142

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Ala Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

```
Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 143
<211> LENGTH: 329
<212> TYPE: PRT
<213> ORGANISM: Artificial Sequence
<220> FEATURE:
<223> OTHER INFORMATION: "Description of Artificial Sequence: Synthetic
      polypeptide"

<400> SEQUENCE: 143

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 144
<211> LENGTH: 330
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 144

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 145
<211> LENGTH: 231
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 145

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Ala Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 146
<211> LENGTH: 232
<212> TYPE: PRT

<213> ORGANISM: Artificial Sequence
<220> FEATURE:
<223> OTHER INFORMATION: "Description of Artificial Sequence: Synthetic polypeptide"

<400> SEQUENCE: 146

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Ala Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 147
<211> LENGTH: 329
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 147

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 148
<211> LENGTH: 330
<212> TYPE: PRT
<213> ORGANISM: Artificial Sequence
<220> FEATURE:
<223> OTHER INFORMATION: "Description of Artificial Sequence: Synthetic polypeptide"

<400> SEQUENCE: 148

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

-continued

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

CD40 ANTAGONIST ANTIBODY VARIANTS WITH IMPROVED PHARMACOKINETIC PROPERTIES

CROSS REFERENCE TO RELATED APPLICATIONS

This application is a national stage application (under 35 U.S.C. § 371) PCT/US2021/032815, filed on May 17, 2021, which claims the benefit of U.S. Provisional Application No. 63/026,499, filed May 18, 2020, each of which is hereby incorporated by reference in its entirety for all purposes.

SUBMISSION OF SEQUENCE LISTING

The instant application contains a Sequence Listing which has been submitted electronically in ASCII format and is hereby incorporated by reference in its entirety. Said ASCII copy, created on Nov. 11, 2022, is named 009616_00223_US_SL.txt and is 281,576 bytes in size.

FIELD

The disclosure provides variants of an antibody wherein the variant antibodies have improved pharmacokinetic properties relative to the corresponding unmodified antibody. In some cases, the antibody polypeptides bind CD40 and do not exhibit CD40 agonist activity. Compositions comprising antibodies, methods of use for treatment of diseases involving CD40 activity, and use in the preparation of a medicament for treatment of a disease involving CD40 activity are provided.

BACKGROUND

Biotherapeutic molecules are often the subject of modification experiments with the intent of trying to increase therapeutic effect, disease exposure, and/or safety profile. For antibody therapeutic molecules, modifications may include humanization, PEGylation, glycosylation, and conjugation to molecules such as albumin Pharmacokinetics (PK) refers to the movement of a drug into, through, and out of the body. Drug pharmacokinetics assesses the onset, duration, and intensity of a drug's effect.

Pharmacokinetics of an antibody therapeutic can be influenced by a wide range of properties, including molecular size, folding stability, solubility, target interaction, neonatal Fc binding capacity, and charge (see, e.g., Warnders et al., 2018, *Med. Res. Rev.* 38: 1837-1873; Leipold and Prabhu, 2019, *Clin. Transl. Sci.* 12: 130-139). Charge modification of an antibody may influence charge-dependent interactions. For instance, increasing the basic/positive charge on a protein (cationization) can increase off-target interaction with membranes and extracellular matrix and tends to reduce pharmacokinetics, whereas anionization of a protein that has basic charge patches generally improves PK. However, protein modification to intentionally modulate in vivo behavior can also result in unintentional and undesirable effects due to the interdependence of many of the properties of proteins. Thus, pursuing charge modification of an antibody to modulate PK is not straightforward and requires intelligent protein design/engineering, and experimentation to find those mutations that work.

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on Tx cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody, leading to the development of several monoclonal anti-CD40 antibodies, such as monoclonal antibody HCD122 (Lucatumumab), formerly known as Chiron 1212, fully human domain antibody BMS-986090 (U.S. Pat. No. 9,475,879). See also, e.g., WO 2018/217976 and WO 2018/217988.

SUMMARY

The disclosure provides variants of an antibody wherein the variant antibodies have improved pharmacokinetic properties relative to the corresponding unmodified antibody. A method for increasing at least one pharmacokinetic property is also provided. The disclosure further provides anti-CD40 monoclonal antibody variants having similar or improved pharmacokinetic properties relative to the corresponding non-modified parent antibody. The disclosure also provides a method for the intelligent design of antibody variants having similar or improved pharmacokinetics relative to a corresponding non-modified antibody.

An isolated antibody, or antigen binding portion thereof, is provided that specifically binds to human CD40, wherein the antibody comprises a first polypeptide portion comprising a heavy chain variable region (VH), and a second polypeptide portion comprising a light chain variable region (VL), wherein the heavy chain variable region and the light chain variable region are selected from:

(i) said heavy chain variable region comprises HC1

```
(QVQLVQSGAEVKKPGSSVKVSCKASGYAFTSYWMHWVRQAPGQGLEW
MGQINPTTGRSQYNEKFKTRVTITADKSTSTAYMELSSLRSEDTAVYY
CARWGLQPFAYWGQGTLVTVSS; SEQ ID NO. 40);
and said light chain variable region comprises LC4
(DIQMTQSPSFLSASVGDRVTITCKASQDVSTAVAWYQQKPGKAPQLL
IYSASYQYTGVPSQFSGSGSGTDFTLTISSLQPEDFATYYCQQHYSTP
WTFGGGTKVEIK; SEQ ID NO. 41);
```

(ii) said heavy chain variable region comprises HC1

```
(QVQLVQSGAEVKKPGSSVKVSCKASGYAFTSYWMHWVRQAPGQGLEW
MGQINPTTGRSQYNEKFKTRVTITADKSTSTAYMELSSLRSEDTAVYY
CARWGLQPFAYWGQGTLVTVSS; SEQ ID NO. 40);
and said light chain variable region comprises LC3
(DIQMTQSPSFLSASVGDRVTITCKASQDVSTAVAWYQQKPGKAPELL
IYSASYRYTGVPSRFSGSGSGTDFTLTISSLQPEDFATYYCQQHYSTP
WTFGGGTKVEIK; SEQ ID NO. 42);
```

(iii) said heavy chain variable region comprises HC15

(QVQLVQSGAEVKKPGSSVKVSCKASGYAFTSYWMHWVRQAPGQGLEW MGQINPTTGRSQYNEKFKTQVTITADKSTSTAYMELSSLRSEDTAVYY CARWGLQPFAYWGQGTLVTVSS; SEQ ID NO. 43);

and said light chain variable region comprises LC3

(DIQMTQSPSFLSASVGDRVTITCKASQDVSTAVAWYQQKPGKAPELL IYSASYRYTGVPSRFSGSGSGTDFTLTISSLQPEDFATYYCQQHYSTP WTFGGGTKVEIK; SEQ ID NO. 42);

(iv) said heavy chain variable region comprises HC4

(QVQLVQSGAEVEKPGSSVKVSCKASGYAFTSYWMHWVRQAPGQGLEW MGQINPTTGRSQYNEKFKTRVTITADKSTSTAYMELSSLRSEDTAVYY CARWGLQPFAYWGQGTLVTVSS; SEQ ID NO. 44);

and said light chain variable region comprises LC1

(DIQMTQSPSFLSASVGDRVTITCKASQDVSTAVAWYQQKPGKAPKLL IYSASYRYTGVPSRFSGSGSGTDFTLTISSLQPEDFATYYCQQHYSTP WTFGGGTKVEIK; SEQ ID NO. 45);

(v) said heavy chain variable region comprises HC4

(QVQLVQSGAEVEKPGSSVKVSCKASGYAFTSYWMHWVRQAPGQGL EWMGQINPTTGRSQYNEKFKTRVTITADKSTSTAYMELSSLRSEDT AVYYCARWGLQPFAYWGQGTLVTVSS; SEQ ID NO. 44);

and said light chain variable region comprises LC3

(DIQMTQSPSFLSASVGDRVTITCKASQDVSTAVAWYQQKPGKAPE LLIYSASYRYTGVPSRFSGSGSGTDFTLTISSLQPEDFATYYCQQH YSTPWTFGGGTKVEIK; SEQ ID NO. 42);

or (vi) said heavy chain variable region comprises HC5

(QVQLVQSGAEVEQPGSSVKVSCEASGYAFTSYWMHWVRQAPGQGL EWMGQINPTTGRSQYNEKFKTRVTITADKSTSTAYMELSSLRSEDTA VYYCARWGLQPFAYWGQGTLVTVSS; SEQ ID NO. 46);

and said light chain variable region comprises LC4

(DIQMTQSPSFLSASVGDRVTITCKASQDVSTAVAWYQQKPGKAPQ LLIYSASYQYTGVPSQFSGSGSGTDFTLTISSLQPEDFATYYCQQH YSTPWTFGGGTKVEIK; SEQ ID NO. 41).

The isolated antibody or antigen binding portion thereof can comprise the first polypeptide portion comprising a human heavy chain constant region; and the second polypeptide portion comprising a human light chain constant region. The isolated antibody or antigen binding portion thereof described herein can comprise a human IgG1 Fc domain comprising either (1) a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding; or (2) an alanine substituted at Kabat position 297.

In some embodiments of the isolated antibody or antigen binding portion thereof described herein, the first polypeptide portion comprises a heavy chain variable region and a heavy chain constant region, and the second polypeptide portion comprises a light chain variable region and a light chain constant region wherein:

(i) said heavy chain variable region comprises HC1

(QVQLVQSGAEVKKPGSSVKVSCKASGYAFTSYWMHWVRQAPGQGL EWMGQINPTTGRSQYNEKFKTRVTITADKSTSTAYMELSSLRSEDT AVYYCARWGLQPFAYWGQGTLVTVSS*ASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKRV*; SEQ ID NO. 47);

and said light chain variable region comprises LC4

(DIQMTQSPSFLSASVGDRVTITCKASQDVSTAVAWYQQKPGKAPQ LLIYSASYQYTGVPSQFSGSGSGTDFTLTISSLQPEDFATYYCQQH YSTPWTFGGGTKVEIK*RTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC*; SEQ ID NO. 20);

(ii) said heavy chain variable region comprises HC1

(QVQLVQSGAEVKKPGSSVKVSCKASGYAFTSYWMHWVRQAPGQGL EWMGQINPTTGRSQYNEKFKTRVTITADKSTSTAYMELSSLRSEDT AVYYCARWGLQPFAYWGQGTLVTVSS*ASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKRV*; SEQ ID NO. 47);

and said light chain variable region comprises LC3

(DIQMTQSPSFLSASVGDRVTITCKASQDVSTAVAWYQQKPGKAPE LLIYSASYRYTGVPSRFSGSGSGTDFTLTISSLQPEDFATYYCQQH YSTPWTFGGGTKVEIK*RTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPNTKSFNRGEC*; SEQ ID NO. 19);

(iii) said heavy chain variable region comprises HC15

(QVQLVQSGAEVKKPGSSVKVSCKASGYAFTSYWMHWVRQAPGQGL EWMGQINPTTGRSQYNEKFKTQVTITADKSTSTAYMELSSLRSEDT AVYYCARWGLQPFAYWGQGTLVTVSS*ASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKRVT*; SEQ ID NO. 48);

and said light chain variable region comprises LC3

(DIQMTQSPSFLSASVGDRVTITCKASQDVSTAVAWYQQKPGKAPE LLIYSASYRYTGVPSRFSGSGSGTDFTLTISSLQPEDFATYYCQQH YSTPWTFGGGTKVEIK*RTVAAPSVFIFPPSDEQLKSGTASVVCLLNN*

-continued

FYPREAKVQWKVDNALQSGNSQESVTEQDSKDSTYSLSSTLTLSKA

DYEKHKVYACEVTHQGLSSPNTKSFNRGEC; SEQ ID NO. 19);

(iv) said heavy chain variable region comprises HC4

(QVQLVQSGAEVKKPGSSVKVSCKASGYAFTSYWMHWVRQAPGQGL

EWMGQINPTTGRSQYNEKFKTRVTITADKSTSTAYMELSSLRSEDT

AVYYCARWGLQPFAYWGQGTLVTVSSASTKGPSVFPLAPSSKSTSG

GTAALGCLVKDYFPEPVTVSWNSGALTSGVHTFPAVLQSSGLYSLS

SVVTVPSSSLGTQTYICNVNHKPSNTKVDKRV; SEQ ID NO. 49);

and said light chain variable region comprises LC1

(DIQMTQSPSFLSASVGDRVTITCKASQDVSTAVAWYQQKPGKAPK

LLIYSASYRYTGVPSRFSGSGSGTDFTLTISSLQPEDFATYYCQQH

YSTPWTFGGGTKVEIKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGEC; SEQ ID NO. 17);

(v) said heavy chain variable region comprises HC4

(QVQLVQSGAEVKKPGSSVKVSCKASGYAFTSYWMHWVRQAPGQGL

EWMGQINPTTGRSQYNEKFKTRVTITADKSTSTAYMELSSLRSEDT

AVYYCARWGLQPFAYWGQGTLVTVSSASTKGPSVFPLAPSSKSTSG

GTAALGCLVKDYFPEPVTVSWNSGALTSGVHTFPAVLQSSGLYSLS

SVVTVPSSSLGTQTYICNVNHKPSNTKVDKRV; SEQ ID NO. 49);

and said light chain variable region comprises LC3

(DIQMTQSPSFLSASVGDRVTITCKASQDVSTAVAWYQQKPGKAPK

LLIYSASYRYTGVPSRFSGSGSGTDFTLTISSLQPEDFATYYCQQH

YSTPWTFGGGTKVEIKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPNTKSFNRGEC; SEQ ID NO. 19);

or (vi) said heavy chain variable region comprises HC5

(QVQLVQSGAEVKQPGSSVKVSCKASGYAFTSYWMHWVRQAPGQGL

EWMGQINPTTGRSQYNEKFKTRVTITADKSTSTAYMELSSLRSEDT

AVYYCARWGLQPFAYWGQGTLVTVSSASTKGPSVFPLAPSSKSTSG

GTAALGCLVKDYFPEPVTVSWNSGALTSGVHTFPAVLQSSGLYSLS

SVVTVPSSSLGTQTYICNVNHKPSNTKVDKRV; SEQ ID NO. 50);

and said light chain variable region comprises LC4

(DIQMTQSPSFLSASVGDRVTITCKASQDVSTAVAWYQQKPGKAPQ

LLIYSASYQYTGVPSQFSGSGSGTDFTLTISSLQPEDFATYYCQQH

YSTPWTFGGGTKVEIKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGEC; SEQ ID NO. 20).

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion has reduced FcγR binding. An exemplary antibody may have P238 mutated to lysine.

The isolated antibody or antigen binding portion thereof described herein can comprise an Fc domain which comprises an amino acid sequence selected from:

(SEQ ID NO: 22; IgG1-P238K (-C-term Lys))
EPKSCDKTHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG, (SEQ ID NO: 23; IgG1-P238K)
EPKSCDKTHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK, (SEQ ID NO: 24; CH1-IgG1-P238K (-C-term Lys))
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKYHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG, (SEQ ID NO: 25; CH1-IgG1-P238K)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKYHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK, (SEQ ID NO: 26; IgG1f-P238K (-C-term Lys))
EPKSCDKTHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPG,

-continued (SEQ ID NO: 27; IgG1f-P238K)
EPKSCDKTHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK, (SEQ ID NO: 28; CH1-IgG1f-P238K (-C-term Lys))
*ASTKGPSVFPLAPSSKSTSGGTAALGCLVKDYFPEPVTVSWNSGALTSG*

*VHTFPAVLQSSGLYSLSSVVTVPSSSLGTQTYICNVNHKPSNTKVDKRV*

EPKSCDKFHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPG,
or (SEQ ID No: 29; CH1-IgG1f-P238K)
*ASTKGPSVFPLAPSSKSTSGGTAALGCLVKDYFPEPVTVSWNSGALTSG*

*VHTFPAVLQSSGLYSLSSVVTVPSSSLGTQTYICNVNHKPSNTKVDKRV*

EPKSCDKYHTCPPCPAPELLGGKSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

The isolated antibody or antigen binding portion thereof can comprise a human IgG1 Fc domain comprising the amino acid sequence of SEQ ID NO: 22 or SEQ ID NO: 23.

An isolated antibody or antigen binding portion thereof described herein may comprise a human IgG1 Fc domain comprises a human IgG1 Fc domain comprising an alanine substituted at Kabat position 297.

An isolated antibody or antigen binding portion thereof as described herein can antagonize activities of CD40. The isolated antibody or antigen binding portion thereof described herein can be a chimeric antibody. The isolated antibody or antigen binding portion thereof described herein can be a humanized antibody. The isolated antibody or antigen binding portion thereof described herein can comprise a human heavy chain constant region and a human light chain constant region.

The antibody or antigen binding portion thereof disclosed herein may comprise an antigen binding portion selected from the group consisting of Fv, Fab, F(ab')2, Fab', dsFv, scFv, sc(Fv)2, diabodies, and scFv-Fc. An exemplary isolated antibody or antigen binding portion thereof as described herein is a scFv-Fc.

The antibody or antigen binding portion thereof disclosed herein can linked to a therapeutic agent.

The antibody or antigen binding portion thereof disclosed herein can be linked to a second functional moiety having a different binding specificity than said antibody or antigen binding portion thereof.

The antibody or antigen binding portion thereof disclosed herein can further comprise an additional moiety.

A nucleic acid molecule encoding an isolated antibody or antigen binding portion thereof is disclosed herein. An expression vector comprising the nucleic acid molecule is disclosed herein. Also disclosed is a cell transformed with the expression vector that can express an isolated antibody or antigen binding portion thereof as disclosed herein. Also disclosed is a method of preparing an anti-human CD40 antibody, or antigen binding portion thereof, comprising:

a) expressing the antibody, or antigen binding portion thereof, in the cell transformed with the expression vector comprising the nucleic acid molecule encoding an isolated antibody or antigen binding portion thereof disclosed herein; and b) isolating the antibody, or antigen binding portion thereof, from the cell.

Also provided is a pharmaceutical composition comprising: a) the antibody, or antigen binding portion thereof disclosed herein; and b) a pharmaceutically acceptable carrier.

A method is provided of treating or preventing an immune response in a subject comprising administering to the subject the antibody, or the antigen binding portion thereof, disclosed herein. Further provided is a method of treating or preventing an autoimmune or inflammatory disease in a subject, comprising administering to the subject the antibody, or the antigen binding portion, disclosed herein. Optionally, the antibody, or the antigen binding portion thereof, can be administered with an immunosuppressive/immunomodulatory and/or anti-inflammatory agent. Administration may be simultaneous or sequential. An exemplary agent for co-administration is a CTLA4 mutant molecule, such as L104EA29Y-Ig (belatacept).

In such method of treating or preventing an immune response in the subject, and in such method of treating or preventing an autoimmune or inflammatory disease in a subject, preferably the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Also contemplated is an antibody, or antigen binding portion thereof as disclosed here, for use as a medicament. Further contemplated is an antibody, or antigen binding portion thereof as disclosed here, or a medicament comprising the same, for use to treat a subject in need thereof. Further contemplated is an antibody, or antigen binding portion thereof as disclosed herein in a therapeutically-effective amount, for use in treating or preventing an immune response, wherein the antibody or antigen binding portion thereof is for administering to a patient in need thereof.

DETAILED DESCRIPTION

Figure 1:
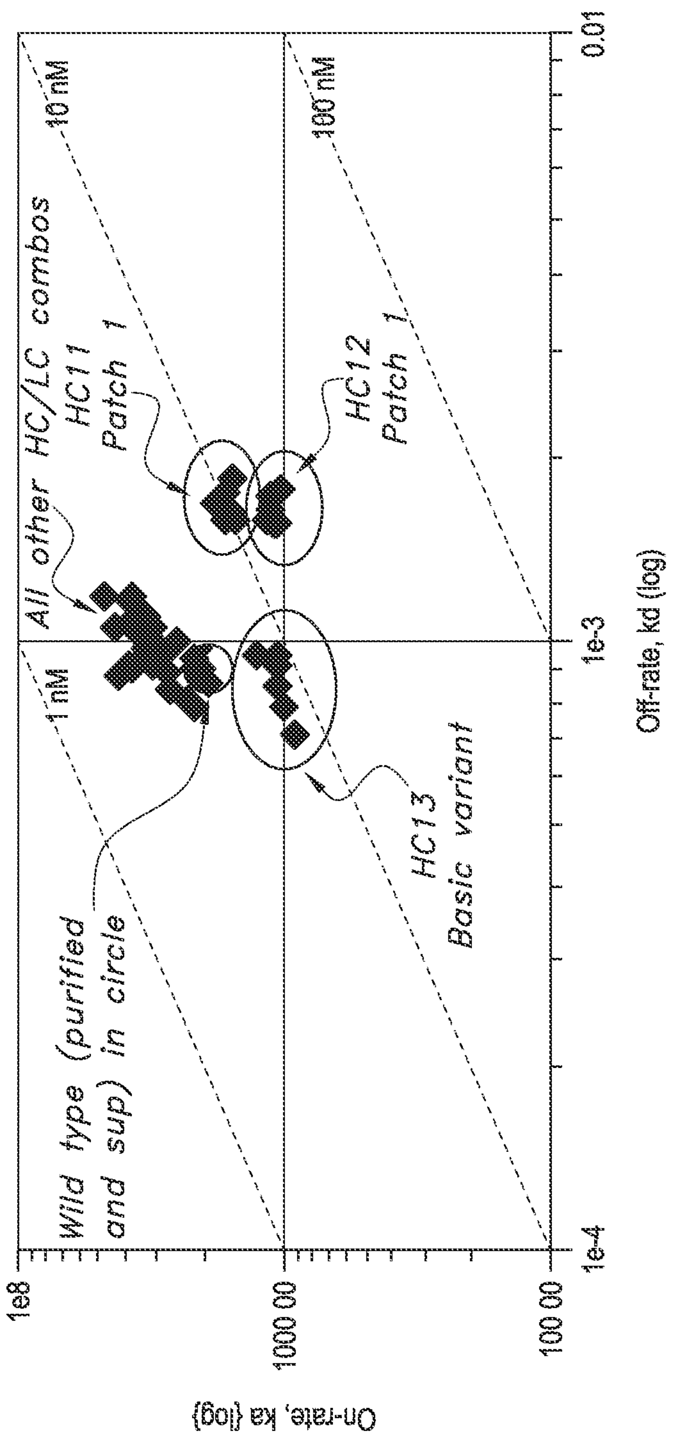
FIG. 1 depicts a graph of on-rate versus off-rate (iso affinity) plot for hCD40 binding to protein A-captured antibodies. The X-axis is off-rate (kd) and the y-axis is on-rate (ka); the graph is in log scale. Wild-type=data for HC1/LC1 antibody. HC13 Basic variant=data for antibodies HC13/LC1, HC13/LC2, HC13/LC3, HC13/LC4, HC13/LC5, and HC13/LC6. HC11 Patch 1=data for antibodies HC11/LC1, HC11/LC2, HC11/LC3, HC11/LC4, HC11/LC5, and HC11/LC6. HC12 Patch 1=data for antibodies HC12/LC1, HC12/LC2, HC12/LC3, HC12/LC4, HC12/LC5, and HC12/LC6.
Figure 2:
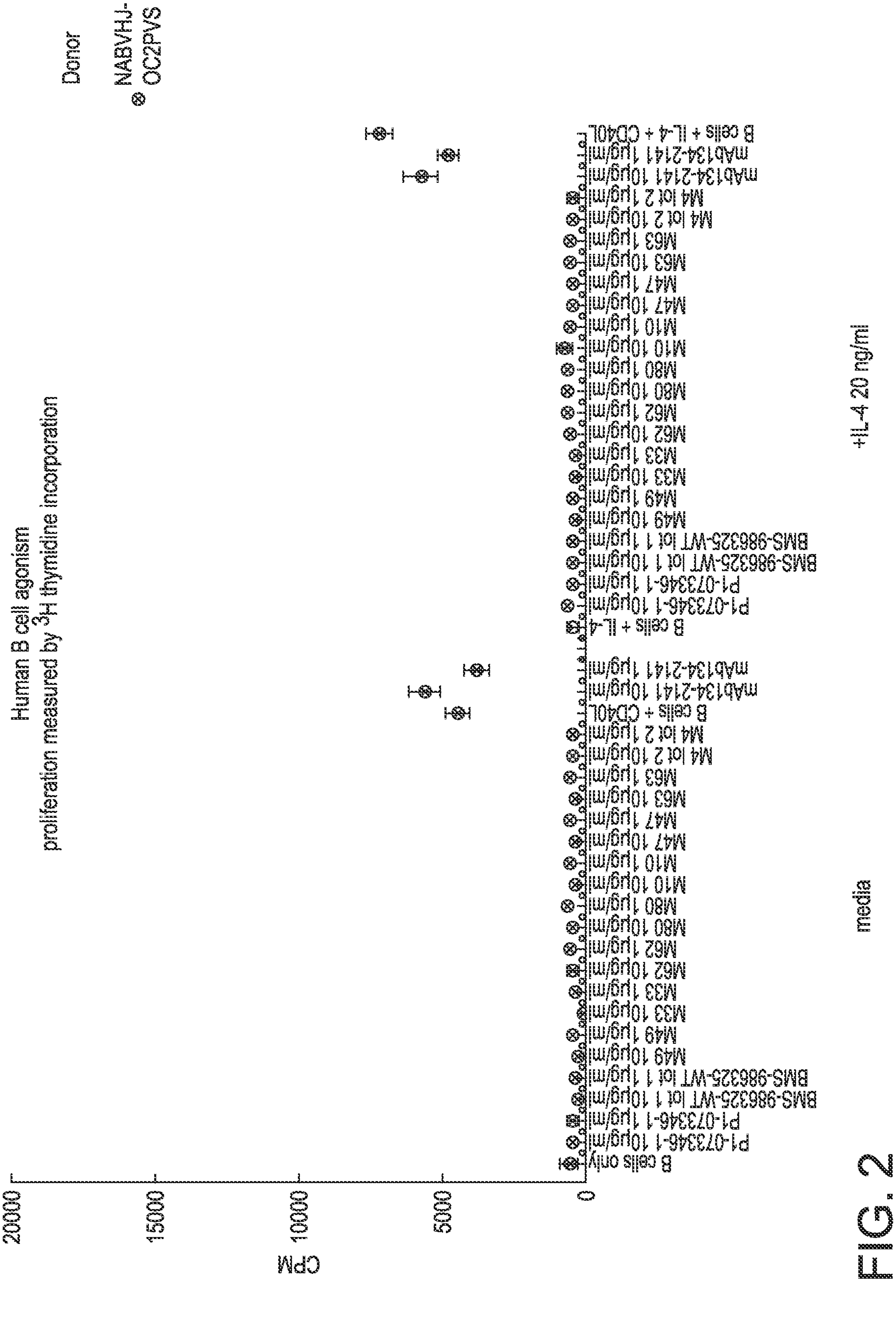
FIG. 2 depicts data for BMS-986325 and its variants agonism of human B cell proliferation, measured by $^3$H thymidine incorporation, in the presence of soluble human IL-4 (+IL-4 20 ng/ml) or absence of IL-4 (media). These data used human B cells from donor NABVHJ-OC2PVS.
Figure 3:
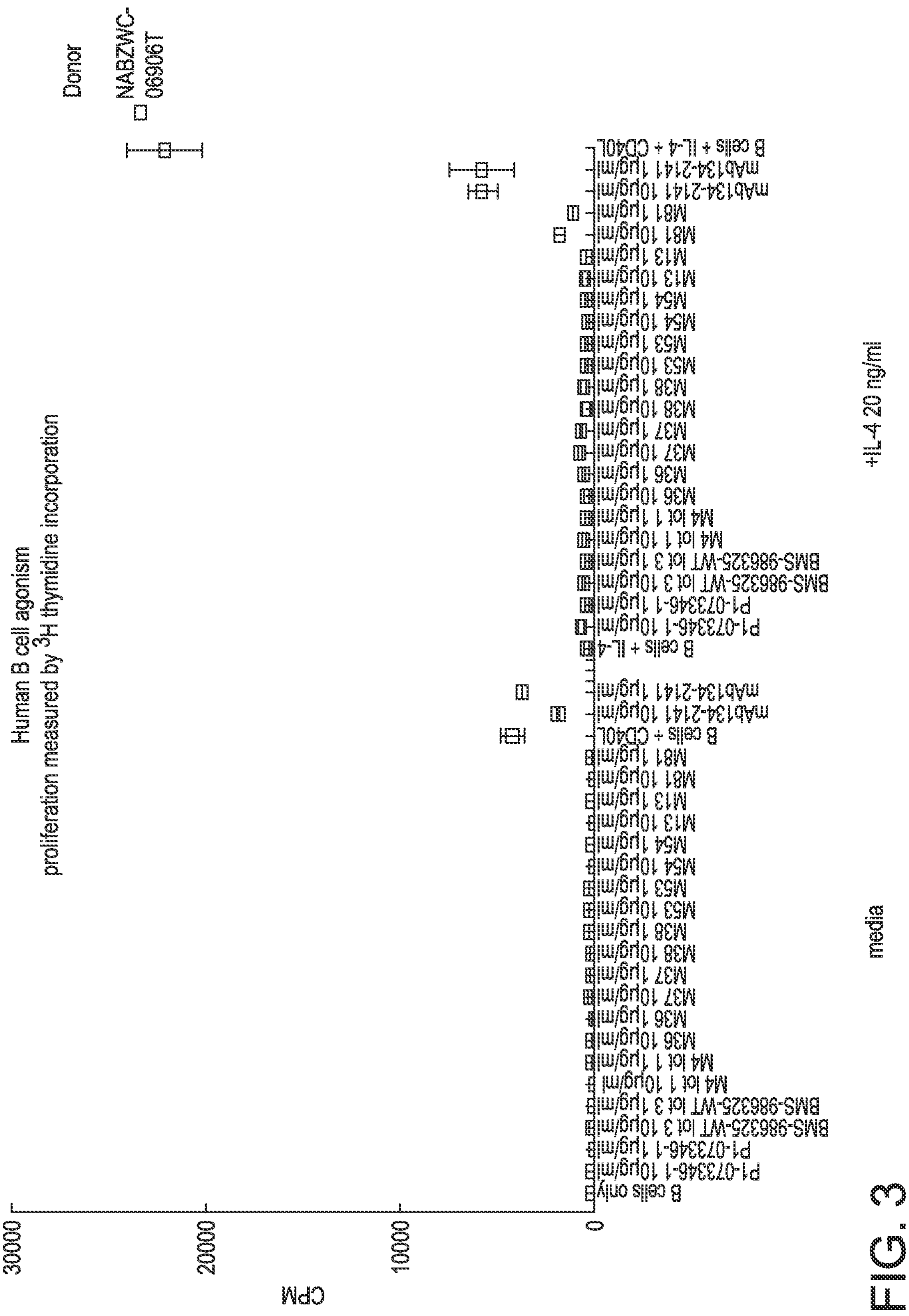
FIG. 3 depicts data for BMS-986325 and its variants agonism of human B cell proliferation, measured by $^3$H thymidine incorporation, in the presence of IL-4 (+IL-4 20 ng/ml) or absence of IL-4 (media). These data used human B cells from donor NABZWC-06906T.
Figure 4:
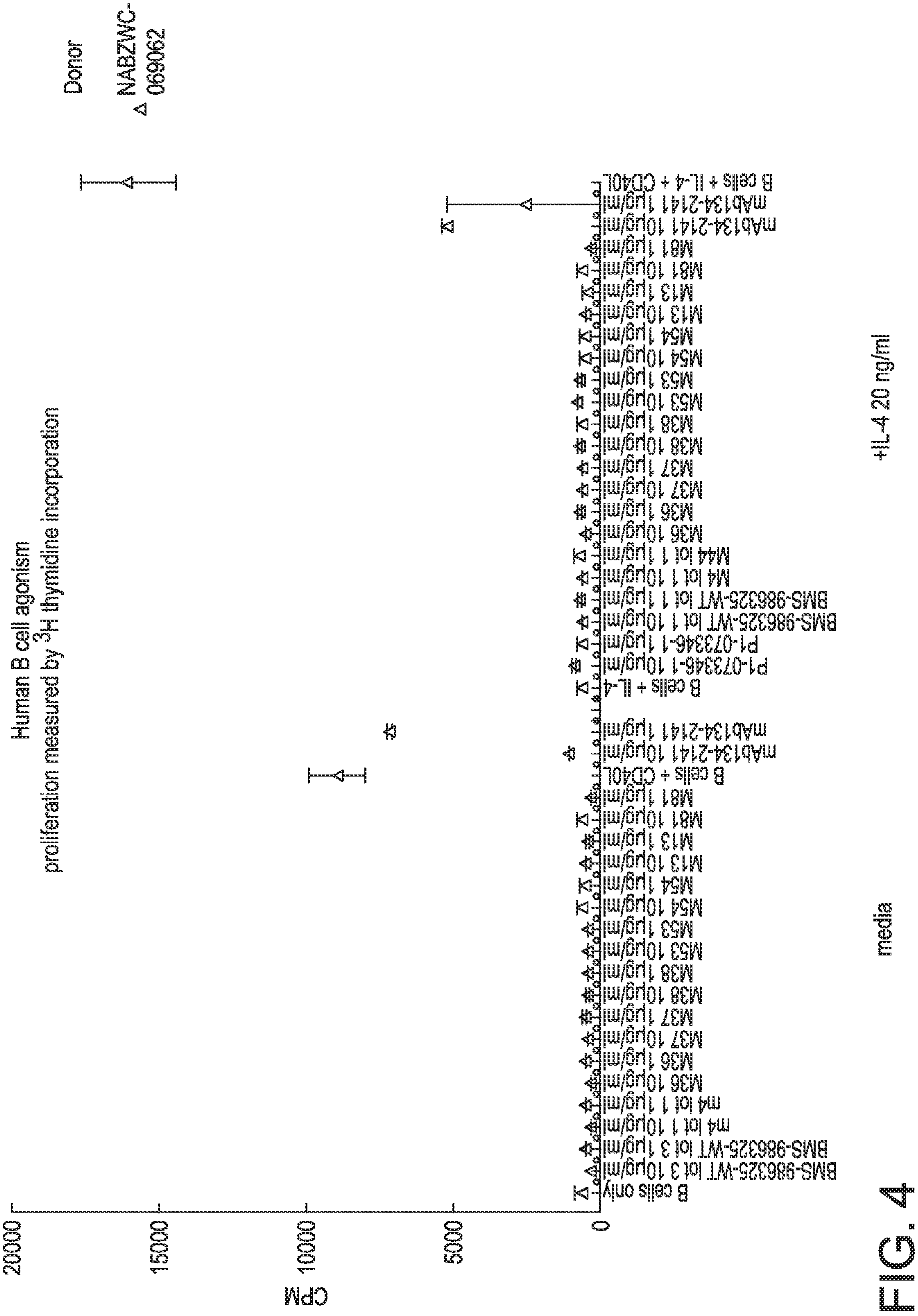
FIG. 4 depicts data for BMS-986325 and its variants agonism of human B cell proliferation, measured by $^3$H thymidine incorporation, in the presence of IL-4 (+IL-4 20 ng/ml) or absence of IL-4 (media). These data used human B cells from donor NABZWC-069062.

The disclosure provides variants of an antibody wherein the variant antibodies have improved pharmacokinetic properties relative to the corresponding unmodified antibody. As shown here, it has been found that the specific site or location of a mutation to modify a surface charge patches is critical to improving antibody PK. This finding is unexpected as the prior art suggested that simply modifying the total antibody charge was needed to effect PK modification. Advantageously, in some instances, variants with only one or two strategically positions mutations with a small change in overall charge e.g., −2 or −3, have equivalent or improved PK compared to variants have multiple mutations and a larger charge change e.g. −8.

The disclosure further provides variants of antibodies that bind CD40 wherein the variants antibodies have improved pharmacokinetic properties relative to the corresponding unmodified antibody. The antibody polypeptides bind CD40 and do not exhibit CD40 agonist activity. Compositions comprising antibodies, methods of use for treatment of diseases involving CD40 activity, and use in the preparation of a medicament for treatment of a disease involving CD40 activity are provided.

The variant antibodies of the disclosure were identified by the method described in Example 1.

Definitions & Abbreviations

Further abbreviations and definitions are provided below.

APC antigen presenting cells

AUC area under the curve

BSA bovine serum album

CD54 also referred to as ICAM-1

CDR complementarity determining regions $C_H$ or CH constant heavy chain $C_L$ or CL constant light chain CHO cell Chinese hamster ovary cell DC dendritic cell FcgR interchangeable with FcγR FcγR Fc-gamma-receptor FR Framework region GM-CSF granulocyte macrophage colony stimulating factor HC heavy chain ICAM-1 intracellular adhesion molecule 1 iDC immature dendritic cells

IFN interferon

IgG immunoglobulin G

IL-6 interleukin-6

LC light chain mAb monoclonal antibody mg milligram ml or mL milliliter ng nanogram nM nanomolar pI isoelectric point SPR surface plasmon resonance TNF tumor necrosis factor μg microgram μM micromolar $V_L$ or VL or Vl variable light chain domain Vκ or Vk or VK kappa variable light chain domain Vλ lambda variable light chain domain $V_H$ or VH or Vh variable heavy chain domain In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, "about" encompasses a range of values that are plus/minus 10% of a referenced value unless indicated otherwise in the specification.

It is understood that any and all whole or partial integers between the ranges set forth are included herein.

CD40 is also known and referred to as B-cell surface antigen CD40, Bp50, CD40L receptor, CDw40, CDW40, MGC9013, p50, TNFRSF5, and tumor necrosis factor (TNF) receptor superfamily member 5. "Human CD40" refers to the CD40 comprising the following amino acid sequence:

```
                                      (SEQ ID NO: 52)
MVRLPLQCVL WGCLLTAVHP EPPTACREKQ YLINSQCCSL

CQPGQKLVSD CTEFTETECL PCGESEFLDT WNRETHCHQH

KYCDPNLGLR VQQKGTSETD TICTCEEGWH CTSEACESCV

LHRSCSPGFG VKQIATGVSD TICEPCPVGF FSNVSSAFEK

CHPWTSCETK DLVVQQAGTN KTDVVCGPQD RLRALVVIPI
```

-continued

```
IFGILFAILL VLVFIKKVAK KPTNKAPHPK QEPQEINFPD

DLPGSNTAAP VQETLHGCQP VTQEDGKESR ISVQERQ.
```

As used herein, the term "variable domain" refers to immunoglobulin variable domains defined by Kabat et al., Sequences of Immunological Interest, 5th ed., U.S. Dept. Health & Human Services, Washington, D.C. (1991). The numbering and positioning of CDR amino acid residues within the variable domains is in accordance with the well-known Kabat numbering convention. VH, "variable heavy chain" and "variable heavy chain domain" refer to the variable domain of a heavy chain. VL, "variable light chain" and "variable light chain domain" refer to the variable domain of a light chain.

The term "human," when applied to antibodies, means that the antibody has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above.

An "isolated" compound as used herein means that the compound is removed from at least one component with which the compound is naturally associated with in nature.

An antibody of the present disclosure, such as an anti-CD40 antibody, comprises a variable heavy chain and a variable light chain, each of which contains three complementarity-determining regions (CDRs) and four framework regions (FRs), arranged from amino-terminus to carboxy-terminus in the following order: FR1, CDR1, FR2, CDR2, FR3, CDR3, FR4. The CDRs contain most of the residues that form specific interactions with the antigen and are primarily responsible for antigen recognition.

Pharmacokinetics (PK) refers to the movement of a drug into, through, and out of the body; PK assesses drug absorption, distribution, metabolism, and excretion of drugs from the body. Parameters for assessing pharmacokinetics include: AUC 0-inf (μM·h), T-half (h), MRT (h), CL (mL/h/kg) and Vss (L/kg).

| Abbreviation | Name |
|---|---|
| AUC 0-inf (uM · h) | Area under the concentration-time curve from time 0 to infinity |
| T-half (h) | Half-life |
| MRT (h), | Mean residence time |
| CL (mL/h/kg) | Clearance |
| Vss (L/kg) | Volume of distribution at steady state |

PK parameters can be assessed by methods described herein.

As used herein, "improved pharmacokinetic properties" means that at least one PK parameter for an antibody variant is increased (for AUC, T-half and MRT) or decreased (for CL and Vss) relative to the same PK parameter measured in the corresponding non-modified antibody. In embodiments, an antibody variant has improved pharmacokinetic properties in at least two PK parameters, at least three PK parameters, at least four PK parameters, or at least five PK parameters relative to the same PK parameters in the corresponding non-modified antibody. As used herein, an improved pharmacokinetic property refers to a pharmacokinetic property of a variant antibody that is at least 5%, 10%, 20%, 30%, 40%, 50%, 60%, 70%, 80%, 90%, or at least 100% greater than the same pharmacokinetic property of the corresponding unmodified antibody.

The exemplary anti-CD40 antibodies of the present disclosure are variants of humanized antibody BMS-986325 (also referred to as Y12XX-hz28). An overview of the amino acid sequences of the heavy chain variable region and light chain variable region of BMS-986325 is provided in Table 1.

TABLE 1

| Antibody | HC Variable Region | LC Variable Region |
|---|---|---|
| BMS-986325 (Y12XX-hz28) | QVQLVQSGAEVKKPGSSV KVSCKASGYAFTSYWMHW VRQAPGQGLEWMGQINPT TGRSQYNEKFKTRVTITA DKSTSTAYMELSSLRSED TAVYYCARWGLQPFAYWG QGTLVTVSS (HC1 = HC-wt; SEQ ID NO: 40) | DIQMTQSPSFLSASVGDR VTITCKASQDVSTAVAWY QQKPGKAPKLLIYSASYR YTGVPSRFSGSGSGTDFT LTISSLQPEDFATYYCQQ HYSTPWTFGGGTKVEIK (LC1 = LC-wt; SEQ ID NO: 45) |

Details of the amino acid sequences of BMS-986325 are provided in Table 2.

TABLE 2

| BMS-986325: Y12XX-hz28 sequence | | |
|---|---|---|
| Name | Sequence | Comment |
| Heavy chain variable region | QVQLVQSGAEVKKPGSSVKVSCKASGYAFT **SYWMH**WVRQAPGQGLEWMG**QINPTTGRSQY NEKFKT**RVTITADKSTSTAYMELSSLRSED TAVYYCAR**WGLQPFAY**WGQGTLVTVSS (HC1 = HC-wt; SEQ ID NO: 40) | Vh-hz14 (SEQ ID NO: 40; CDRs underlined) |
| VH-CDR1 | SYWMH SEQ ID NO: 53) | Amino acids 31-35 of SEQ ID NO: 40 |
| VH-CDR2 | QINPTTGRSQYNEKFKT (SEQ ID NO: 54) | Amino acids 50-66 of SEQ ID NO: 40 |
| VH-CDR3 | WGLQPFAY (SEQ ID NO: 55) | Amino acids 99-106 of SEQ ID NO: 40 |

TABLE 2-continued

BMS-986325: Y12XX-hz28 sequence

| Name | Sequence | Comment |
|---|---|---|
| HC_Y12XX-hz28-CH1-IgG1-P238K (is IgG1 with and without C-terminal lysine) | QVQLVQSGAEVKKPGSSVKVSCKASGYAFT**SYWMH**WVRQAPGQGLEWMG**QINPTTGRSQYNEKFKT**RVTITADKSTSTAYMELSSLRSEDTAVYYCAR**WGLQPFAY**WGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV*EPKSCDKTHTCPPCPAPELLGGKSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 56) | CDRs underlined; CH1 = amino acids 118-215 (italicized); IgG1-P238K = amino acids 216-446; P238K underlined; no C-terminal lysine |
| | QVQLVQSGAEVKKPGSSVKVSCKASGYAFT**SYWMH**WVRQAPGQGLEWMG**QINPTTGRSQYNEKFKT**RVTITADKSTSTAYMELSSLRSEDTAVYYCAR**WGLQPFAY**WGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV*EPKSCDKTHTCPPCPAPELLGGKSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 1) | CDRs underlined; CH1 = amino acids 118-215 (italicized); IgG1-P238K = amino acids 216-447; P238K underlined; C-terminal lysine present |
| Light chain variable region | DIQMTQSPSFLSASVGDRVTITC**KASQDVSTAVA**WYQQKPGKAPKLLIY**SASYRYT**GVPSRFSGSGSGTDFTLTISSLQPEDFATYYC**QQHYSTPWT**FGGGTKVEIK (LC1 = LC-wt; SEQ ID NO: 45) | Vk-hz2 (SEQ ID NO: 45; CDRs underlined) |
| VL-CDR1 | KASQDVSTAVA (SEQ ID NO: 31) | Amino acids 24-34 of SEQ ID NO: 45 |
| VL-CDR2 | SASYRYT (SEQ ID NO: 57) | Amino acids 50-56 of SEQ ID NO: 45 |
| VL-CDR3 | QQHYSTPWT (SEQ ID NO: 58) | Amino acids 89-97 of SEQ ID NO: 45 |
| LC_Y12XX-hz28 | DIQMTQSPSFLSASVGDRVTITC**KASQDVSTAVA**WYQQKPGKAPKLLIY**SASYRYT**GVPSRFSGSGSGTDFTLTISSLQPEDFATYYC**QQHYSTPWT**FGGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* (SEQ ID NO: 17) | CDRs underlined; CL = amino acids 108-214 (italicized) |

The anti-CD40 variant antibodies of the present disclosure have at least one specific anionizing mutation in a variable domain relative to the corresponding framework region at least in BMS-986325. The anionizing mutations are of either Lysine (Lys; K) or Arginine (Arg; R) residues generally located in framework regions of the variable chains, and in some variants a CDR. Generally, specific lysine and arginine residues can be mutated to an uncharged residue, such as Glutamine (Gln; Q) or Asparagine (Asn; N), or a negatively charged (acidic) residue, such as Glutamate (Glu; E) or Aspartate (Asp; D). To avoid potential deamidation or isomerization, mutation to Gln and Glu are prioritized over mutation to Asn and Asp respectively to avoid potential deamidation (Asn) or isomerization (Asp) issues that are common for the shorter Asn and Asp side chains. The disclosed variants have improved PK related to BMS-986325.

Combinations of heavy chain variable region and light chain variable region sequences of variants of BMS-986325 disclosed herein are provided in Tables 3-8. These combinations each have a change in variable region net charge, relative to BMS-986325. Specifically, each combination has a decrease in net positive charge, except for those combinations including HC13. The variants bind human CD40 with a KD value similar to the KD for BMS-986325 or no more than about 4-fold higher (as measured by hCD40 binding to BMS-986325 and BMS-986325 variant antibodies captured out of supernatants).

Table 3 comprises combinations of various heavy chain variable region sequences with light chain variable region LC1.

TABLE 3

| | | | |
|---|---|---|---|
| | LC1 | LC-wt | DIQMTQSPSFLSASVGDRVTITCKASQDVSTAVAWYQQKP GKAPKLLIYSASYRYTGVPSRFSGSGSGTDFTLTISSLQP EDFATYYCQQHYSTPWTFGGGTKVEIK (SEQ ID NO: 45) |
| Combo # | | | |
| M2 | HC2 | HC-K12Q, K13Q | QVQLVQSGAEV**QQ**PGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS SEQ ID NO: 59) |
| M3 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M4 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |
| M5 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M6 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M7 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M8 | HC8 | HC-R38Q, K63Q, R67Q | QVQLVOSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M9 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M16 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M10 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M15 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M11 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M12 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |

TABLE 3-continued

| | | | |
|---|---|---|---|
| M14 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |

Table 4 comprises combinations of various heavy chain variable region sequences with light chain variable region LC2.

TABLE 4

| | | | |
|---|---|---|---|
| | LC2 | **LC-K45Q** | DIQMTQSPSFLSASVGDRVTITCKASQDVSTAVAWYQQKP GKAP**Q**LLIY**S**ASYRYTGVPSRFSGSGSGTDFTLTISSLQP EDFATYYCQQHYSTPWTFGGGTKVEIK (SEQ ID NO: 70) |
| Combo # | | | |
| M17 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |
| M18 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M19 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M20 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |
| M21 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M22 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M23 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M24 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M25 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M32 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M26 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |

TABLE 4-continued

| | | | |
|---|---|---|---|
| M31 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M27 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M28 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |
| M30 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |
| M29 | HC13 | HC-E46K, E62K | QVQLVQSGAEVKKPGSSVKVSCKASGYAFTSYWMHWVRQA PGQGLKWMGQINPTTGRSQYNKKFKTRVTITADKSTSTAY MELSSLRSEDTAVYYCARWGLQPFAYWGQGTLVTVSS (SEQ ID NO: 71) |

Table 5 comprises combinations of various heavy chain variable region sequences with light chain variable region LC3.

TABLE 5

| | | | |
|---|---|---|---|
| | LC3 | **LC-K45E** | DIQMTQSPSFLSASVGDRVTITCKASQDVSTAVAWYQQKP GKAPELLIYSASYRYTGVPSRFSGSGSGTDFTLTISSLQP EDFATYYCQQHYSTPWTFGGGTKVEIK (SEQ ID NO: 42) |
| Combo # | | | |
| M33 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |
| M34 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M35 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M36 | HC4 | HC-K12E | QVQLVOSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |
| M37 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M38 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M39 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |

TABLE 5-continued

| | | | |
|---|---|---|---|
| M40 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M41 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M48 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M42 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M47 | HC15 | HC-R67Q | QVQLVQSGAEVKKPGSSVKVSCKASGYAFTSYWMHWVRQA PGQGLEWMGQINPTTGRSQYNEKFKQVTITADKSTSTAY MELSSLRSEDTAVYYCARWGLQPFAYWGQGTLVTVSS (SEQ ID NO: 43) |
| M43 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M44 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |
| M46 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |
| M45 | HC13 | HC-E46K, E62K | QVQLVQSGAEVKKPGSSVKVSCKASGYAFTSYWMHWVRQA PGQGLKWMGQINPTTGRSQYNKKFKTRVTITADKSTSTAY MELSSLRSEDTAVYYCARWGLQPFAYWGQGTLVTVSS (SEQ ID NO: 71) |

Table 6 comprises combinations of various heavy chain variable region sequences with light chain variable region LC4.

TABLE 6

| | | | |
|---|---|---|---|
| | LC4 | LC-K45Q, R54Q, R61Q | DIQMTQSPSFLSASVGDRVTITCKASQDVSTAVAWYQQKP GKAPQLLIYSASYQYTGVPSQFSGSGSGTDFTLTISSLQP EDFATYYCQQHYSTPWTFGGGTKVEIK (SEQ ID NO: 41) |
| Combo # | | | |
| M49 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |
| M50 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M51 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M52 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |

TABLE 6-continued

| | | | |
|---|---|---|---|
| M53 | HC5 | HC-K12E, K13Q, K23E | QVQLVQSGAEVEQPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 46) |
| M54 | HC6 | HC-K12V, K19S, K23A | QVQLVQSGAEVVKPGSSVSVSCAASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 61) |
| M55 | HC7 | HC-K23E | QVQLVQSGAEVKKPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 62) |
| M56 | HC8 | HC-R38Q, K63Q, R67Q | QVQLVQSGAEVKKPGSSVKVSCKASGYAFTSYWMHWVQQA<br>PGQGLEWMGQINPTTGRSQYNEQFKTQVTITADKSTSTAY<br>MELSSLRSEDTAVYYCARWGLQPFAYWGQGTLVTVSS<br>(SEQ ID NO: 63) |
| M57 | HC9 | HC-K63Q, R67E | QVQLVQSGAEVKKPGSSVKVSCKASGYAFTSYWMHWVRQA<br>PGQGLEWMGQINPTTGRSQYNEQFKTEVTITADKSTSTAY<br>MELSSLRSEDTAVYYCARWGLQPFAYWGQGTLVTVSS<br>(SEQ ID NO: 64) |
| M64 | HC16 | HC-K63Q | QVQLVQSGAEVKKPGSSVKVSCKASGYAFTSYWMHWVRQA<br>PGQGLEWMGQINPTTGRSQYNEQFKTRVTITADKSTSTAY<br>MELSSLRSEDTAVYYCARWGLQPFAYWGQGTLVTVSS<br>(SEQ ID NO: 65) |
| M58 | HC10 | HC-R67E | QVQLVQSGAEVKKPGSSVKVSCKASGYAFTSYWMHWVRQA<br>PGQGLEWMGQINPTTGRSQYNEKFKTEVTITADKSTSTAY<br>MELSSLRSEDTAVYYCARWGLQPFAYWGQGTLVTVSS<br>(SEQ ID NO: 66) |
| M63 | HC15 | HC-R67Q | QVQLVQSGAEVKKPGSSVKVSCKASGYAFTSYWMHWVRQA<br>PGQGLEWMGQINPTTGRSQYNEKFKTQVTITADKSTSTAY<br>MELSSLRSEDTAVYYCARWGLQPFAYWGQGTLVTVSS<br>(SEQ ID NO: 43) |
| M59 | HC11 | HC-R57E | QVQLVQSGAEVKKPGSSVKVSCKASGYAFTSYWMHWVRQA<br>PGQGLEWMGQINPTTGESQYNEKFKTRVTITADKSTSTAY<br>MELSSLRSEDTAVYYCARWGLQPFAYWGQGTLVTVSS<br>(SEQ ID NO: 67) |
| M60 | HC12 | HC-R57E, K74Q | QVQLVQSGAEVKKPGSSVKVSCKASGYAFTSYWMHWVRQA<br>PGQGLEWMGQINPTTGESQYNEKFKTRVTITADQSTSTAY<br>MELSSLRSEDTAVYYCARWGLQPFAYWGQGTLVTVSS<br>(SEQ ID NO: 68) |
| M62 | HC14 | HC-K74T | QVQLVQSGAEVKKPGSSVKVSCKASGYAFTSYWMHWVRQA<br>PGQGLEWMGQINPTTGRSQYNEKFKTRVTITADTSTSTAY<br>MELSSLRSEDTAVYYCARWGLQPFAYWGQGTLVTVSS<br>(SEQ ID NO: 69) |
| M61 | HC13 | HC-E46K, E62K | QVQLVQSGAEVKKPGSSVKVSCKASGYAFTSYWMHWVRQA<br>PGQGLKWMGQINPTTGRSQYNKKFKTRVTITADKSTSTAY<br>MELSSLRSEDTAVYYCARWGLQPFAYWGQGTLVTVSS<br>(SEQ ID NO: 71) |

Table 7 comprises combinations of various heavy chain variable region sequences with light chain variable region LC5.

TABLE 7

| | | | |
|---|---|---|---|
| | LC5 | LC-R61Q | DIQMTQSPSFLSASVGDRVTITCKASQDVSTAVAWYQQKP<br>GKAPKLLIYSASYRYTGVPSQFSGSGSGTDFTLTISSLQP<br>EDFATYYCQQHYSTPWTFGGGTKVEIK<br>(SEQ ID NO: 90) |
| Combo # | | | |
| M65 | HC1 | HC-wt | QVQLVQSGAEVKKPGSSVKVSCKASGYAFTSYWMHWVRQA<br>PGQGLEWMGQINPTTGRSQYNEKFKTRVTITADKSTSTAY |

TABLE 7-continued

| | | | |
|---|---|---|---|
| | | | MELSSLRSEDTAVYYCARWGLQPFAYWGQGTLVTVSS (SEQ ID NO: 40) |
| M66 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M67 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M68 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |
| M69 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M70 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M71 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M72 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M73 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M80 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M74 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M79 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M75 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M76 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |
| M78 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |
| M77 | HC13 | HC-E46K, E62K | QVQLVQSGAEVKKPGSSVKVSCKASGYAFTSYWMHWVRQA PGQGLKWMGQINPTTGRSQYNKKFKTRVTITADKSTSTAY MELSSLRSEDTAVYYCARWGLQPFAYWGQGTLVTVSS (SEQ ID NO: 71) |

Table 8 comprises combinations of various heavy chain variable region sequences with light chain variable region LC6.

TABLE 8

| | | | |
|---|---|---|---|
| | LC6 | LC-K107Q, R108Q | DIQMTQSPSFLSASVGDRVTITCKASQDVSTAVAWYQQKP GKAPKLLIYSASYRYTGVPSRFSGSGSGTDFTLTISSLQP EDFATYYCQQHYSTPWTFGGGTKVEI**QQ** (SEQ ID NO: 72) |
| Combo # | | | |
| M81 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |
| M82 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M83 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M84 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 44) |
| M85 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M86 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M87 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M88 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M89 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M96 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M90 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M95 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M91 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |

TABLE 8-continued

| | | | |
|---|---|---|---|
| M92 | HC12 | HC-R57E, K74Q | QVQLVQSGAEVKKPGSSVKVSCKASGYAFTSYWMHWVRQA<br>PGQGLEWMGQINPTTGESQYNEKFKTRVTITADQSTSTAY<br>MELSSLRSEDTAVYYCARWGLQPFAYWGQGTLVTVSS<br>(SEQ ID NO: 68) |
| M94 | HC14 | HC-K74T | QVQLVQSGAEVKKPGSSVKVSCKASGYAFTSYWMHWVRQA<br>PGQGLEWMGQINPTTGRSQYNEKFKTRVTITADTSTSTAY<br>MELSSLRSEDTAVYYCARWGLQPFAYWGQGTLVTVSS<br>(SEQ ID NO: 69) |
| M93 | HC13 | HC-E46K, E62K | QVQLVQSGAEVKKPGSSVKVSCKASGYAFTSYWMHWVRQA<br>PGQGLKWMGQINPTTGRSQYNKKFKTRVTITADKSTSTAY<br>MELSSLRSEDTAVYYCARWGLQPFAYWGQGTLVTVSS<br>(SEQ ID NO: 71) |

Heavy chain variable region and light chain variable region sequences of exemplary variants of BMS-986325 having improved PK are provided in Table 9.

TABLE 9

| ID | Heavy chain variable region Sequence | Light chain variable region Sequence |
|---|---|---|
| Key: | CDRs are underlined<br>CDR1: amino acids 31-35<br>CDR2: amino acids 50-66<br>CDR3: amino acids 99-106 | CDRs are underlined<br>CDR1: amino acids 24-34<br>CDR2: amino acids 50-56<br>CDR3: amino acids 89-97 |
| | HC1 (wt) | LC4 (K45Q, R54Q, R61Q) |
| M49 | QVQLVQSGAEVKKPGSSVKVSCKASGYAFTSY<br>WMHWVRQAPGQGLEWMGQINPTTGRSQYNE<br>KFKTRVTITADKSTSTAYMELSSLRSEDTAVYY<br>CARWGLQPFAYWGQGTLVTVSS<br>(SEQ ID NO: 40) | DIQMTQSPSFLSASVGDRVTITCKASQDVSTAV<br>AWYQQKPGKAPQLLIYSASYQYTGVPSQFSGS<br>GSGTDFTLTISSLQPEDFATYYCQQHYSTPWTF<br>GGGTKVEIK<br>(SEQ ID NO: 41)<br>K45Q, R54Q, R61Q: bolded underlined |
| | HC1 (wt) | LC3 (K45E) |
| M33 | QVQLVQSGAEVKKPGSSVKVSCKASGYAFTSY<br>WMHWVRQAPGQGLEWMGQINPTTGRSQYNE<br>KFKTRVTITADKSTSTAYMELSSLRSEDTAVYY<br>CARWGLQPFAYWGQGTLVTVSS<br>(SEQ ID NO: 40) | DIQMTQSPSFLSASVGDRVTITCKASQDVSTAV<br>AWYQQKPGKAPELLIYSASYRYTGVPSRFSGSG<br>SGTDFTLTISSLQPEDFATYYCQQHYSTPWTFG<br>GGTKVEIK<br>(SEQ ID NO: 42)<br>K45E: bolded underlined |
| | HC15 (R67Q) | LC3 (K45E) |
| M47 | QVQLVQSGAEVKKPGSSVKVSCKASGYAFTSY<br>WMHWVRQAPGQGLEWMGQINPTTGRSQYNE<br>KFKTQVTITADKSTSTAYMELSSLRSEDTAVYY<br>CARWGLQPFAYWGQGTLVTVSS<br>(SEQ ID NO: 43)<br>R67Q: bolded underlined | DIQMTQSPSFLSASVGDRVTITCKASQDVSTAV<br>AWYQQKPGKAPELLIYSASYRYTGVPSRFSGSG<br>SGTDFTLTISSLQPEDFATYYCQQHYSTPWTFG<br>GGTKVEIK<br>(SEQ ID NO: 42)<br>K45E: bolded underlined |
| M4 | HC4 (K12E) | LC1 (wt) |
| | QVQLVQSGAEVEKPGSSVKVSCKASGYAFTSY<br>WMHWVRQAPGQGLEWMGQINPTTGRSQYNE<br>KFKTRVIIADKSISAYMELSSLRSEDTAVYY<br>CARWGLQPFAYWGQGTLVTVSS<br>(SEQ ID No. 44)<br>K12E: bolded underlined | DIQMTQSPSFLSASVGDRVTITCKASQDVSTAV<br>AWYQQKPGKAPKLLIY**S**ASYRYTGVPSRFSGSG<br>SGTDFTLTISSLQPEDFATYYC***QQHYSTPWT***FGG<br>GTKVEIK<br>(SEQ ID NO. 45) |
| | HC4 (K12E) | LC3 (K45E) |
| M36 | QVQLVQSGAEVEKPGSSVKVSCKASGYAFTSY<br>WMHWVRQAPGQGLEWMGQINPTTGRSQYNE<br>KFKTRVTITADKSTSTAYMELSSLRSEDTAVYY<br>CARWGLQPFAYWGQGTLVTVSS<br>(SEQ ID No. 44)<br>K12E: bolded underlined | DIQMTQSPSFLSASVGDRVTITCKASQDVSTAV<br>AWYQQKPGKAPELLIYSASYRYTGVPSRFSGSG<br>SGTDFTLTISSLQPEDFATYYCQQHYSTPWTFG<br>GGTKVEIK<br>(SEQ ID NO: 42)<br>K45E: bolded underlined |

TABLE 9-continued

| ID | Heavy chain variable region Sequence | Light chain variable region Sequence |
|---|---|---|
| M53 | HC5 (K12E, K13Q, K23E) | LC4 (K45Q, R54Q, R61Q) |
| | QVQLVQSGAEVEQPGSSVKVSCEASGYAFTSY WMHWVRQAPGQGLEWMGQINPTTGRSQYNE KFKTRVTITADKSTSTAYMELSSLRSEDTAVYY CARWGLQPFAYWGQGTLVTVSS (SEQ ID NO. 46) K12E, K13Q, K23E: bolded underlined | DIQMTQSPSFLSASVGDRVTITCKASQDVSTAV AWYQQKPGKAPQLLIYSASYQYTGVPSQFSGS GSGTDFTLTISSLQPEDFATYYCQQHYSTPWTF GGGTKVEIK (SEQ ID NO: 41) K45Q, R54Q, R61Q: bolded underlined |

Exemplary CD40 antibodies of the present disclosure can include an isolated antibody, or antigen binding portion thereof, that specifically binds to human CD40, wherein said antibody comprises a first polypeptide portion comprising a heavy chain variable region, and a second polypeptide portion comprising a light chain variable region, wherein:

(i) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 40);

and said light chain variable region comprises LC4 (DIQMTQSPSFLSASVGDRVTITCKASQDVSTAVAWYQQKPGKAPQLLIYSASYQYTGVPSQFSGSGSGTDFTLTISSLQPEDFATYYCQQHYSTPWTFGGGTKVEIK: SEQ ID NO. 41);

(ii) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 40);

and said light chain variable region comprises LC3 (DIQMTQSPSFLSASVGDRVTITCKASQDVSTAVAWYQQKPGKAPEELLIYSASYRYTGVPSRFSGSGSGTDFTLTISSLQPEDFATYYCQQHYSTPWTFGGGTKVEIK: SEQ ID NO. 42);

(iii) said heavy chain variable region comprises HC15

(QVQLVQSGAEVKKPGSSVKVSCKASGYAFTSYWMHWVRQAPGQGLEWMGQINPTTGRSQYNEKFKTQVTITADKSTSTAYMELSSLRSEDTAVYYCARWGLQPFAYWGQGTLVTVSS; SEQ ID NO. 43);

and said light chain variable region comprises LC3 (DIQMTQSPSFLSASVGDRVTITCKASQDVSTAVAWYQQKPGKAPELLIYSASYRYTGVPSRFSGSGSGTDFTLTISSLQPEDFATYYCQQHYSTPWTFGGGTKVEIK; SEQ ID NO. 42);

(iv) said heavy chain variable region comprises HC4

(QVQLVQSGAEVEKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 44);

and said light chain variable region comprises LC1 (DIQMTQSPSFLSASVGDRVTITCKASQDVSTAVAWYQQKPGKAPKLLIYSASYRYTGVPSRFSGSGSGTDFTLTISSLQPEDFATYYCQQHYSTPWTFGGGTKVEIK; SEQ ID NO. 45);

(v) said heavy chain variable region comprises HC4

(QVQLVQSGAEVEKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 44);
and said light chain variable region comprises LC3 (DIQMTQSPSFLSASVGDRVTITCKASQDVSTAVAWYQQKPGKAPELLIYSASYRYTGVPSRFSGSGSGTDFTLTISSLQPEDFATYYCQQHYSTPWTFGGGTKVEIK: SEQ ID NO. 42);

or (vi) said heavy chain variable region comprises HC5

(QVQLVQSGAEVEQPGSSVKVSCEASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 46);

and said light chain variable region comprises LC4 (DIQMTQSPSFLSASVGDRVTITCKASQDVSTAVAWYQQKPGKAPQLLIYSASYQYTGVPSQFSGSGSGTDFTLTISSLQPEDFATYYCQQHYSTPWTFGGGTKVEIK: SEQ ID NO. 41).

Exemplary CD40 antibodies of the present disclosure can include an isolated antibody, or antigen binding portion thereof, that specifically binds to human CD40, wherein said antibody comprises a first polypeptide portion comprising a heavy chain variable region, and a second polypeptide portion comprising a light chain variable region, wherein:

(i) said heavy chain variable region comprises HC1

(QVQLVQSGAEVKKPGSSVKVSCKASGYAFTSYWMHWVRQAPGQGLEWMG
QINPTTGRSQYNEKFKTRVTITADKSTSTAYMELSSLRSEDTAVYYCARW
GLQPFAYWGQGTLVTVSS; SEQ ID NO. 40);

and said light chain variable region comprises LC3
(DIQMTQSPSFLSASVGDRVTITCKASQDVSTAVAWYQQKPGKAPELLI
YSASYRYTGVPSRFSGSGSGTDFTLTISSLQPEDFATYYCQQHYSTPWTF
GGGTKVEIK; SEQ ID NO. 42);

or (ii) said heavy chain variable region comprises HC15 (QVQLVQSGAEVKKPGSSVKVSCKASGYAFT-SYWMHWVRQAPGQGLEWMGQINPT TGR-SQYNEKFKT Q VTITADKSTSTAYMELSSLRSED-TAVYYCARWGLQPFAYWGQG TLVTVSS; SEQ ID NO. 43); and said light chain variable region comprises LC3 (DIQMTQSPSFLSASVGDRVTITCK-ASQDVSTAVAWYQQKPGKAP E LLIYSASYRYTGVPSRFSGSGSGTDFTLTISSL-QPEDFATYYCQQHYSTPWTFGGGTKVEIK; SEQ ID NO. 42). These two exemplary antibodies have the fewest mutations while also have a particularly advantageous combination of properties, including at least one improved PK parameter.

An "antibody" (Ab) shall include, without limitation, an immunoglobulin that binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, $F(ab')_2$, scFv (single-chain variable fragment), Fab', dsFv, sc(Fv)2, and scFv-Fc.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

As used herein, "specific binding" refers to the binding of an antigen by an antibody with a dissociation constant ($K_d$) of about 1 μM or lower as measured, for example, by surface plasmon resonance (SPR). Suitable assay systems include the BIAcore™ (GE Healthcare Life Sciences, Marlborough, MA) surface plasmon resonance system and BIAcore™ kinetic evaluation software (e.g., version 2.1).

Binding of the present antibodies to CD40 antagonizes at least one CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

CALR (P27797);
ERP44 (Q9BS26);
FBL (P22087);
POLR2H (P52434);
RFC5 (P40937);
SGK1 (000141);
SLC30A7 (Q8NEW0);
SLC39A7 (Q92504);
TRAF2 (Q5T1L5);
TRAF3 (Q13114);
TRAF6 (Q9Y4K3);
TXN (Q5T937);
UGGT1 (Q9NYU2); and
USP15 (Q9Y4E8).

For example, a CD40 "activity" includes an interaction with TRAF2. CD40/TRAF2 interaction activates NF-κB and JNK. See Davies et al., Mol. Cell Biol. 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the CD40 activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody may antagonize some or all CD40 activity, while not activating CD40. For example, the antibody may not activate B cell proliferation. The antibody may not activate cytokine secretion by T cells, where the cytokine is at least one cytokine selected from the group consisting of IL-2, IL-6, IL-10, IL-13, TNF-α, and IFN-γ.

The isolated antibody or antigen binding portion thereof can antagonize one or more activities of CD40. The isolated antibody or antigen binding portion thereof can be a chimeric antibody. The isolated antibody or antigen binding portion thereof can be a humanized antibody. The isolated antibody or antigen binding portion thereof can comprise a human heavy chain constant region and a human light chain constant region.

In certain aspects, the present disclosure describes variant framework regions (FR) and in some instances CDRs of the variable domains, wherein certain positions having a basic amino acid are mutated to a neutral or an acidic amino acid. The variant FRs disclosed may be variants of a framework region encoded by a human germline antibody gene segment such as a VH1 heavy chain germline and a VK1 light chain germline, or variants of modified FRs of a human germline antibody gene segment, for instance, variants arising from mutagenic affinity maturation of antibody libraries. Preferred framework sequences for use in the antibodies described herein are those that are structurally similar to the framework sequences used by anti-CD40 antibodies described herein. It is contemplated that $V_H$ CDR1, 2 and 3 sequences, and the $V_L$ CDR1, 2 and 3 sequences of any antibody can be grafted onto framework regions disclosed herein to improve one or more PK parameters. It is also contemplated that, as described herein, certain positions in CDRs that have a basic amino acid can also be modified.

Thus, the disclosure contemplates monoclonal antibody variants having similar or improved pharmacokinetic properties relative to the corresponding non-modified parent antibody. The parent antibody comprises a first polypeptide portion comprising a heavy chain variable region, said heavy chain variable region having the amino acid sequence QVQLVQSGAEVKKPGSSVKVSCKASG-YAFTXXXXXWVRQAPGQGLEWMGXXXX XXXXXXXXXXXXXRVTITADKST-STAYMELSSLRSEDTAVYYCARXXXXXXXXW GQGTLVTVSS (SEQ ID NO: 73); and a second polypeptide portion comprising a light chain variable region, said light chain variable region having the amino acid sequence DIQMTQSPSFL-SASVGDRVTITCXXXXXXXXXXXWYQQKPGKAP-KWYXXXXXXX XGVPSRFSGSGSGTDFTLTISSLQPED-FATYYCXXXXXXXXXFGGGTKVEIK. (SEQ ID NO: 74) or DIQMTQSPSFL-SASVGDRVTITCXXXXXXXXXXXWYQQKPGKAP-KWYXXXXXXX XGVPSRFSGSGSGTDFTLTISSLQPED-FATYYCXXXXXXXXXFGGGTKVEIKR (SEQ ID NO: 75) In SEQ ID NO: 75, position 108 is the first amino acid of the constant region (CL). Position 108 can be a basic amino acid, such as an arginine as shown in SEQ ID NO: 75.

The antibody variants comprise at least one anionizing mutation at a basic residue. The heavy chain variable region of the variant can comprise a mutation at at least one position having a basic residue in the parent antibody, the at least one position selected from the group consisting of 12, 13, 19, 23, 38, 57, 63, 67, and 74, and combinations thereof, of SEQ ID NO: 73. The heavy chain variable region of the variant can comprise at least one mutation as a position selected from the group consisting of K12, K13, K19, K23, R38, R57, K63, R67, and R74 and combinations thereof. The mutation can replace the basic amino acid with either a neutral amino acid or an acidic amino acid. Exemplary neutral amino acids include glutamine, asparagine, valine, serine, alanine, and threonine. Exemplary acid amino acids include glutamate and aspartate. Combinations of mutations can be made at two or more of positions 12, 13, 19, 23, 38, 57, 63, 67, and 74 of SEQ ID NO: 73. Examples include, but are not limited to, mutations at positions 12 and 13; mutations at positions 12, 13, and 23; mutations at positions 38, 63, and 67; mutations at positions 63 and 67; and mutations at positions 57 and 74. In some variant antibodies, examples of combinations include, but are not limited to, mutations at K12 and K13Q; mutations at K12, K13, and K23; mutations at R38, K63 and R67; mutations at K63 and R67; and mutations at R57 and K74. Exemplary combinations of mutations include K12Q, and K13Q; K12Q, K13Q, and K23Q; K12E, K13Q, and K23E; K12V, K19S, and K23A; R38Q, K63Q, and R67Q; K63Q and R67E; and R57E and K74Q.

Heavy Chain Variable Region—Vh Germline

| Basic Residue | Exemplified Modifications | Location in heavy chain variable region |
|---|---|---|
| K12 | Q, E, V | FR1 |
| K13 | Q | FR1 |
| K19 | S | FR1 |
| K23 | Q, E, A | FR1 |
| R38 | Q | FR2 |
| R57 | E | CDR2 |
| K63 | Q | CDR2 |
| R67 | Q, E | FR3 |
| K74 | Q, T | FR3 |

The light chain variable region of the variant can comprise a mutation at at least one position having a basic residue in the parent antibody, the at least one position selected from the group consisting of 45, 54, 61, and 107, and combinations thereof, of SEQ ID NO: 74 or the at least one position selected from the group consisting of 45, 54, 61, 107, and 108, and combinations thereof, of SEQ ID NO: 75. The light chain variable region of the variant can comprise a mutation at at least one position selected from the group consisting of K45, R54, R61, K107 and if present, R108, and combinations thereof. The mutation can replace the basic amino acid with a neutral amino acid or an acidic amino acid. Exemplary neutral amino acids include glutamine (E), asparagine (N), valine (V), serine (S), alanine (A), and threonine (T). In some cases, the neutral amino acid is glutamine. Exemplary acidic amino acids include glutamate (E) and aspartate (E). In some cases, the acidic amino acid is glutamate. Combinations of mutations can be made at two or more of positions 45, 54, 61, and 107 of SEQ ID NO: 74, or 45, 54, 61, 107, and 108 of SEQ ID NO: 75. Examples include, but are not limited to, mutation at positions 45, 54, and 61; or mutation at positions 107 and 108. In some variant antibodies, examples of combinations include, but are not limited to, K45, R54 and R61; and K107 and K108. Exemplary combinations of mutations include K45Q, R54Q and R61Q; and K107Q and K108Q.

Light Chain Variable Region—Vk Germline

| Basic Residue | Exemplified Modifications | Location in light chain variable region |
|---|---|---|
| K45 | Q, E | FR2 |
| R54 | Q | CDR2 |
| R61 | Q | FR3 |
| K107 | Q | FR4 |
| R108 | Q | 1st residue of CL |

The disclosure further provides a method for improving at least one pharmacokinetic property of a parent antibody. The method comprises mutating a residue at at least one position selected from 12, 13, 19, 23, 38, 57, 63, 67, and 74 of SEQ ID NO: 73 and/or 45, 54, 61, and 107 of SEQ ID NO: 74 to produce a variant having at least one improved pharmacokinetic property, relative to the non-modified parent antibody. In some cases, the method comprises mutating a residue at at least one position selected from 12, 13, 19, 23, 38, 57, 63, 67, and 74 of SEQ ID NO: 73 and/or 45, 54, 61, 107, and 108 of SEQ ID NO: 75 to produce a variant having at least one improved pharmacokinetic property, relative to the non-modified parent antibody.

In practicing the method, the mutation can be to a neutral amino acid or to an acidic amino acid. Exemplary neutral amino acids include glutamine, asparagine, valine, serine, alanine, and threonine. Exemplary acid amino acids include glutamate and aspartate.

Combinations of mutations can be made at residues at two or more of positions 45, 54, 61, and 107, and combinations thereof, of SEQ ID NO: 74, or 45, 54, 61, 107, and 108, and combinations thereof, of SEQ ID NO: 75. Examples include, but are not limited to, mutation at positions 45, 54, and 61 of SEQ ID NO: 74; or mutations at 107 and 108 of SEQ ID NO: 75.

Combinations of mutations can be made at two or more positions 12, 13, 19, 23, 38, 57, 63, 67, and 74, and combinations thereof, of SEQ ID NO: 73. Examples include, but are not limited to, mutations at positions 12 and 13; positions 12, 13, and 23; positions 38, 63, and 67; positions 63 and 67, and positions 57 and 74.

The improved pharmacokinetic property obtained by the method can be area under the concentration-time curve from time 0 to infinity (AUC 0-inf (uM·h)), half-life (T-half (h)), mean residence time (MRT (h)), clearance (CL (mL/h/kg), and volume of distribution at steady state (Vss (L/kg)).

Exemplary combinations of variant framework regions are provided in Table 10.

TABLE 10

| ID | Heavy chain variable region Sequence | Light chain variable region Sequence |
|---|---|---|
| Key: | CDRs are underlined<br>CDR1: amino acids 31-35<br>CDR2: amino acids 50-66<br>CDR3: amino acids 99-106<br>X = any amino acid | CDRs are underlined<br>CDR1: amino acids 24-34<br>CDR2: amino acids 50-56<br>CDR3: amino acids 89-97<br>X = any amino acid |
| | HC1 (wt) Framework | LC4 (K45Q, R54Q, R61Q) Framework |
| M49-framework | QVQLVQSGAEVKKPGSSVKVSCKAS<br>GYAFTXXXXXWVRQAPGQGLEWM<br>GXXXXXXXXXXXXXXXXXRVTITA<br>DKSTSTAYMELSSLRSEDTAVYYCA<br>RXXXXXXXXWGQGTLVTVSS<br>(SEQ ID NO: 73) | DIQMTQSPSFLSASVGDRVTITCXXXX<br>XXXXXXXWYQQKPGKAPQLLIYXXX<br>XQXXGVPSQFSGSGSGTDFTLTISSLQP<br>EDFATYYCXXXXXXXXXFGGGTKVEI<br>K<br>(SEQ ID NO: 80)<br>K45Q, R54Q, R61Q: bolded underlined |
| | HC1 (wt) Framework | LC3 (K45E) Framework |
| M33-framework | QVQLVQSGAEVKKPGSSVKVSCKAS<br>GYAFTXXXXXWVRQAPGQGLEWM<br>GXXXXXXXXXXXXXXXXXRVTITA<br>DKSTSTAYMELSSLRSEDTAVYYCA<br>RXXXXXXXXWGQGTLVTVSS<br>(SEQ ID NO: 73) | DIQMTQSPSFLSASVGDRVTITCXXXX<br>XXXXXXXWYQQKPGKAPELLIYXXX<br>XXXXGVPSRFSGSGSGTDFTLTISSLQP<br>EDFATYYCXXXXXXXXXFGGGTKVEI<br>K<br>(SEQ ID NO: 81)<br>K45E: bolded underlined |
| | HC15 (R67Q) Framework | LC3 (K45E) Framework |
| M47-framework | QVQLVQSGAEVKKPGSSVKVSCKAS<br>GYAFTXXXXXWVRQAPGQGLEWM<br>GXXXXXXXXXXXXXXXXXQVTITA<br>DKSTSTAYMELSSLRSEDTAVYYCA<br>RXXXXXXXXWGQGTLVTVSS<br>(SEQ ID NO: 76)<br>R67Q: bolded underlined | DIQMTQSPSFLSASVGDRVTITCXXXX<br>XXXXXXXWYQQKPGKAPELLIYXXX<br>XXXXGVPSRFSGSGSGTDFTLTISSLQP<br>EDFATYYCXXXXXXXXXFGGGTKVEI<br>K<br>(SEQ ID NO: 81)<br>K45E: bolded underlined |
| | HC4 (K12E) Framework | LC1 (wt) Framework |
| M4-framework | QVQLVQSGAEVEKPGSSVKVSCKAS<br>GYAFTXXXXXWVRQAPGQGLEWM<br>GXXXXXXXXXXXXXXXXXRVTITA<br>DKSTSTAYMELSSLRSEDTAVYYCA<br>RXXXXXXXXWGQGTLVTVSS<br>(SEQ ID No. 78)<br>K12E: bolded underlined | DIQMTQSPSFLSASVGDRVTITCXXXX<br>XXXXXXXWYQQKPGKAPKLLIYXXX<br>XXXXGVPSRFSGSGSGTDFTLTISSLQP<br>EDFATYYCXXXXXXXXXFGGGTKVEI<br>K<br>(SEQ ID NO. 74) |
| | HC4 (K12E) Framework | LC3 (K45E) Framework |
| M36-framework | QVQLVQSGAEVEKPGSSVKVSCKAS<br>GYAFTXXXXXWVRQAPGQGLEWM<br>GXXXXXXXXXXXXXXXXXRVTITA<br>DKSTSTAYMELSSLRSEDTAVYYCA<br>RXXXXXXXXWGQGTLVTVSS<br>(SEQ ID No. 78)<br>K12E: bolded underlined | DIQMTQSPSFLSASVGDRVTITCXXXX<br>XXXXXXXWYQQKPGKAPELLIYXXX<br>XXXXGVPSRFSGSGSGTDFTLTISSLQP<br>EDFATYYCXXXXXXXXXFGGGTKVEI<br>K<br>(SEQ ID NO: 81)<br>K45E: bolded underlined |

TABLE 10-continued

| ID | Heavy chain variable region Sequence | Light chain variable region Sequence |
|---|---|---|
| | HC5 (K12E,K13Q,K23E) Framework | LC4 (K45Q,R54Q,R61Q) Framework |
| M53-framework | QVQLVQSGAEVEQPGSSVKVSCEAS<br>GYAFTXXXXXWVRQAPGQGLEWM<br>GXXXXXXXXXXXXXXXXXRVTITA<br>DKSTSTAYMELSSLRSEDTAVYYCA<br>RXXXXXXXXWGQGTLVTVSS<br>(SEQ ID NO. 79)<br>K12E, K13Q, K23E: bolded underlined | DIQMTQSPSFLSASVGDRVTITCXXXX<br>XXXXXXXWYQQKPGKAPQLLIYXXX<br>XQXXGVPSQFSGSGSGTDFTLTISSLQP<br>EDFATYYCXXXXXXXXXFGGGTKVEI<br>K<br>(SEQ ID NO: 80)<br>K45Q, R54Q, R61Q: bolded underlined |

Antibodies contemplated in the present disclosure can include an isolated antibody, or antigen binding portion thereof, that specifically binds to an antigen, wherein said antibody comprises a first polypeptide portion comprising a heavy chain variable region, and a second polypeptide portion comprising a light chain variable region, wherein:

(i) said heavy chain variable region comprises the HC1 framework (QVQLVQSGAEVKKPGSSVKVSCKASGYAFTXXXXXWVRQAPGQGLEWMGXXXXXXXXXXXXXXXXXRVTITADKSTSTAYMELSSLRSEDTAVYYCARXXXXXXXXWGQGTLVTVSS; SEQ ID NO. 73);

and said light chain variable region comprises the LC4 framework (DIQMTQSPSFLSASVGDRVTITCXXXXXXXXXXXWYQQKPGKAPQLLIYXXXXQXXGVPSQFSGSGSGTDFTLTISSLQPEDFATYYCXXXXXXXXXFGGGTKVEIK: SEQ ID NO. 80);

(ii) said heavy chain variable region comprises the HC1 framework (QVQLVQSGAEVKKPGSSVKVSCKASGYAFTXXXXXWVRQAPGQGLEWMGXXXXXXXXXXXXXXXXXRVTITADKSTSTAYMELSSLRSEDTAVYYCARXXXXXXXXWGQGTLVTVSS; SEQ ID NO. 73);

and said light chain variable region comprises the LC3 framework (DIQMTQSPSFLSASVGDRVTITCXXXXXXXXXXXWYQQKPGKAPELLIYXXXXXXXGVPSRFSGSGSGTDFTLTISSLQPEDFATYYCXXXXXXXXXFGGGTKVEIK: SEQ ID NO. 81);

(iii) said heavy chain variable region comprises the HC15 framework (QVQLVQSGAEVKKPGSSVKVSCKASGYAFTXXXXXWVRQAPGQGLEWMGXXXXXXXXXXXXXXXXXQVTITADKSTSTAYMELSSLRSEDTAVYYCARXXXXXXXXWGQGTLVTVSS; SEQ ID NO. 76);

and said light chain variable region comprises the LC3 framework (DIQMTQSPSFLSASVGDRVTITCXXXXXXXXXXXWYQQKPGKAPELLIYXXXXXXXGVPSRFSGSGSGTDFTLTISSLQPEDFATYYCXXXXXXXXXFGGGTKVEIK: SEQ ID NO. 81);

(iv) said heavy chain variable region comprises the HC4 framework (QVQLVQSGAEVEKPGSSVKVSCKASGYAFTXXXXXWVRQAPGQGLEWMGXXXXXXXXXXXXXXXXXRVTITADKSTSTAYMELSSLRSEDTAVYYCARXXXXXXXXWGQGTLVTVSS; SEQ ID NO. 78);

and said light chain variable region comprises the LC1 framework (DIQMTQSPSFLSASVGDRVTITCXXXXXXXXXXXWYQQKPGKAPKLLIYXXXXXXXGVPSRFSGSGSGTDFTLTISSLQPEDFATYYCXXXXXXXXXFGGGTKVEIK: SEQ ID NO. 74);

(v) said heavy chain variable region comprises the HC4 framework (QVQLVQSGAEVEKPGSSVKVSCKASGYAFTXXXXXWVRQAPGQGLEWMGXXXXXXXXXXXXXXXXXRVTITADKSTSTAYMELSSLRSEDTAVYYCARXXXXXXXXWGQGTLVTVSS; SEQ ID NO. 78);

and said light chain variable region comprises the LC3 framework (DIQMTQSPSFLSASVGDRVTITCXXXXXXXXXXXWYQQKPGKAPELLIYXXXXXXXGVPSRFSGSGSGTDFTLTISSLQPEDFATYYCXXXXXXXXXFGGGTKVEIK; SEQ ID NO. 81);

or (vi) said heavy chain variable region comprises the HC5 framework (QVQLVQSGAEVEQPGSSVKVSCEASGYAFTXXXXXWVRQAPGQGLEWMGXXXXXXXXXXXXXXXXXRVTITADKSTSTAYMELSSLRSEDTAVYYCARXXXXXXXXWGQGTLVTVSS; SEQ ID NO. 79);

and said light chain variable region comprises the LC4 framework (DIQMTQSPSFLSASVGDRVTITCXXXXXXXXXXXWYQQKPGKAPQLLIYXXXXQXXGVPSQFSGSGSGTDFTLTISSLQPEDFATYYCXXXXXXXXXFGGGTKVEIK: SEQ ID NO. 80).

Antibodies contemplated in the present disclosure can include an isolated antibody, or antigen binding portion thereof, that specifically binds to an antigen, wherein said antibody comprises a first polypeptide portion comprising a heavy chain variable region, and a second polypeptide portion comprising a light chain variable region, wherein said heavy chain variable region comprises the HC1 framework (QVQLVQSGAEVKKPGSSVKVSCKASGYAFTXXXXXWVRQAPGQGLEWMG

XXXXXXXXXXXXXXXXXRVTITADKSTSTAYMELSSLRSEDTAVYYCARX

XXXXXXXWGQGTLVTVSS; SEQ ID NO. 73);
and said light chain variable region comprises the LC3 framework

DIQMTQSPSFLSASVGDRVTITCXXXXXXXXXXXWYQQKPGKAPELLIY

XXXXXXXGVPSRFSGSGSGTDFTLTISSLQPEDFATYYCXXXXXXXXXFG

GGTKVEIK; SEQ ID NO: 81).

Antibodies contemplated in the present disclosure can include an isolated antibody, or antigen binding portion thereof, that specifically binds to an antigen, wherein said antibody comprises a first polypeptide portion comprising a heavy chain variable region, and a second polypeptide portion comprising a light chain variable region, wherein said heavy chain variable region comprises the HC15 framework (QVQLVQSGAEVKKPGSSVKVSCKASGYAFTXXXXXWVRQAPGQGLEWMG

XXXXXXXXXXXXXXXXXQVTITADKSTSTAYMELSSLRSEDTAVYYCAR

XXXXXXXXWGQGTLVTVSS; SEQ ID NO. 76);
and said light chain variable region comprises the LC3 framework (DIQMTQSPSFLSASVGDRVTITCXXXXXXXXXXXWYQQKPGKAPELLI

YXXXXXXXGVPSRFSGSGSGTDFTLTISSLQPEDFATYYCXXXXXXXXXF

GGGTKVEIK: SEQ ID NO. 81).

Fc Domain and Constant Region

The carboxyl-terminal "half" of a heavy chain defines a constant region (Fc) and which is primarily responsible for effector function. As used herein, the term "Fc domain" refers to the constant region antibody sequences comprising CH2 and CH3 constant domains as delimited according to Kabat et al., *Sequences of Immunological Interest,* $5^{th}$ ed., U.S. Dept. Health & Human Services, Washington, D.C. (1991). The Fc region may be derived from a human IgG. For instance, the Fc region may be derived from a human IgG1 or a human IgG4 Fc region. A heavy variable domain can be fused to an Fc domain The carboxyl terminus of the variable domain may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. Optionally, the protein may comprise the hinge region after the CH1 domain in whole or in part. Optionally an amino acid linker sequence is present between the variable domain and the Fc domain. The carboxyl terminus of the light variable domain may be linked or fused to the amino terminus of a CL domain.

An exemplary sequence for a heavy chain CH1 is amino acids 118-215 of SEQ ID NO: 82

(ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV; SEQ ID NO: 82). An exemplary sequence for a light chain CL is amino acids 108-214 of SEQ ID NO: 83

(RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC; SEQ ID NO: 83).

Exemplary heavy chain variable region and light chain variable region sequences of exemplary variants of BMS-986325 having improved PK are provided in Table 11. In these sequences, the heavy chain comprises an exemplary CH1 domain and the light chain comprises an exemplary CL domain.

TABLE 11

| ID | VH Chain Sequence | VL Chain Sequence |
|---|---|---|
| Key: | CDRs are underlined<br>CDR1: amino acids 31-35<br>CDR2: amino acids 50-66<br>CDR3: amino acids 99-106<br>CH1 = amino acids 118-215 (italicized) | CDRs are underlined<br>CDR1: amino acids 24-34<br>CDR2: amino acids 50-56<br>CDR3: amino acids 89-97<br>CL = amino acids 108-214 (italicized) |
| | HC1 (wt) | LC4 (K45Q, R54Q, R61Q) |
| M49 | QVQLVQSGAEVKKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSS*ASTKGPSVFPLAPS*<br>*SKSTSGGTAALGCLVKDYFPEPVTVSWN*<br>*SGALTSGVHTFPAVLQSSGLYSLSSVVTV*<br>*PSSSLGTQTYICNVNHKPSNTKVDKRV*<br>(SEQ ID NO: 47) | DIQMTQSPSFLSASVGDRVTITCKASQ<br>DVSTAVAWYQQKPGKAPQLLIYSASY<br>QYTGVPSQFSGSGSGTDFTLTISSLQPE<br>DFATYYCQQHYSTPWTFGGGTKVEIK<br>*RTVAAPSVFIFPPSDEQLKSGTASVVCLLN*<br>*NFYPREAKVQWKVDNALQSGNSQESVTE*<br>*QDSKDSTYSLSSTLTLSKADYEKHKVYAC*<br>*EVTHQGLSSPVTKSFNRGEC*<br>(SEQ ID NO: 20)<br>K45Q, R54Q, R61Q: bolded underlined |
| | HC1 (wt) | LC3 (K45E) |
| M33 | QVQLVQSGAEVKKPGSSVKVSCKASG<br>YAFTSYWMHWVRQAPGQGLEWMGQ | DIQMTQSPSFLSASVGDRVTITCKASQ<br>DVSTAVAWYQQKPGKAPELLIYSASY |

TABLE 11-continued

| ID | VH Chain Sequence | VL Chain Sequence |
|---|---|---|
| | INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRV<br>(SEQ ID NO: 47) | RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| | HC15 (R67Q) | LC3 (K45E) |
| M47 | QVQLVQSGAEVKKPGSSVKVSCKASG<br>YAFTSYWMHWVRQAPGQGLEWMGQ<br>INPTTGRSQYNEKFKTQVTITADKSTS<br>TAYMELSSLRSEDTAVYYCARWGLQP<br>FAYWGQGTLVTVSSASTKGPSVFPLAP<br>SSKSTSGGTAALGCLVKDYFPEPVTVSW<br>NSGALTSGVHTFPAVLQSSGLYSLSSVVT<br>VPSSSLGTQTYICNVNHKPSNTKVDKRV<br>(SEQ ID NO: 86)<br>R67Q: bolded underlined | DIQMTQSPSFLSASVGDRVTITCKASQ<br>DVSTAVAWYQQKPGKAPELLIYSASY<br>RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| M4 | HC4 (K12E) | LC1 (wt) |
| | QVQLVQSGAEVEKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRV<br>(SEQ ID No. 49)<br>K12E: bolded underlined | DIQMTQSPSFLSASVGDRVTITCKASQ<br>DVSTAVAWYQQKPGKAPKLLIYSASY<br>RYTGVPSRFSGSGSGTDFTLTISSLQPE<br>DFATYYC**QQHYSTPWT**FGGGTKVEIK<br>RTVAAPSVFIFPPSDEQLKSGTASVNCLL<br>NNFYPREAKVQWKVDNALQSGNSQESVT<br>EQDSKDSTYSLSSTLTLSKADYEKHKVYA<br>CEVTHQGLSSPVTKSFNRGEC<br>(SEQ ID NO. 17) |
| | HC4 | LC3 (K45E) |
| M36 | QVQLVQSGAEVEKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRV<br>(SEQ ID No. 49)<br>K12E: bolded underlined | DIQMTQSPSFLSASVGDRVTITCKASQ<br>DVSTAVAWYQQKPGKAPELLIYSASY<br>RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| M53 | HC5 (K12E, K13Q, K23E) | LC4 (K45Q, R54Q, R61Q) |
| | QVQLVQSGAEVEQPGSSVKVSCEASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRV<br>(SEQ ID NO. 50)<br>K12E, K13Q, K23E: bolded underlined | DIQMTQSPSFLSASVGDRVTITCKASQ<br>DVSTAVAWYQQKPGKAPQLLIYSASY<br>QYTGVPSQFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 20)<br>K45Q, R54Q, R61Q: bolded underlined |

The antibody can be a fusion antibody comprising a first variable domain that specifically binds human CD40, and a second domain comprising an Fc domain Exemplary Fc domains used in the fusion protein can include human IgG domains Exemplary human IgG Fc domains include IgG4 Fc domain and IgG1 Fc domain. While human IgG heavy chain genes encode a C-terminal lysine, the lysine is often absent from endogenous antibodies as a result of cleavage while in blood circulation. Antibodies having IgG heavy chains including a C-terminal lysine, when expressed in mammalian cell cultures, may also have variable levels of C-terminal lysine present (Cai et al, 2011, *Biotechnol. Bioeng.* 108(2): 404-12). Accordingly, the C-terminal lysine of any IgG heavy chain Fc domain disclosed herein may be omitted.

The isolated antibody or antigen binding portion thereof described herein, can comprise an Fc domain which comprises an amino acid sequence of: EPKSCDKTHTCPPCPA-PELLGG(P/K)SVFLFPPKPKDTLMISRTPEVTCVV VDVSHEDPEVKFNWYVDGVEVHNAKTKPREEQY(N/A)STYRVVSVLTV LHQDWLNGKEYKCKVSNKALPA-PIEKTISKAKGQPREPQVYTLPPSR(D/E) E(L/M) TKNQVSLTCLVKGFYPSDIAVEWESNGQPENNYKT-TPPVLDSDGSF FLYSKLTVDKSRWQQGNVF-SCSVMHEALHNHYTQKSLSLSPG(K/not present) (Fc consensus; SEQ ID NO: 87). The parenthetical notation indicates possible amino acid identities at the position. For instance, Kabat position 238 can be either Proline (P) or Lysine (K), which is notated as (P/K). Additional exemplary, non-limiting consensus sequences are SEQ ID NOs: 118-120:

(SEQ ID NO: 118)
EPKSCDKTHT CPPCPAPELL GGXSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR XEXTKNQVSL TCLVKGFYPS

DIAVEWESNG QPENNYKTTP PVLDSDGSFF LYSKLTVDKS

RWQQGNVFSC SVMHEALHNH YTQKSLSLSP GX;

(SEQ ID NO: 119)
EPKSCDKTHT CPPCPAPELL GGPSVFLFPP KPKDTLMISR

TPEVTCVVVD VSHEDPEVKF NWYVDGVEVH NAKTKPREEQ

YASTYRVVSV LTVLHQDWLN GKEYKCKVSN KALPAPIEKT

ISKAKGQPRE PQVYTLPPSR XEXTKNQVSL TCLVKGFYPS

DIAVEWESNG QPENNYKTTP PVLDSDGSFF LYSKLTVDKS

RWQQGNVFSC SVMHEALHNH YTQKSLSLSP GX;
and (SEQ ID NO: 120)
EPKSCDKTHT CPPCPAPELL GGXSVFLFPP KPKDTLMISR

TPEVTCVVVD VSHEDPEVKF NWYVDGVEVH NAKTKPREEQ

YXSTYRVVSV LTVLHQDWLN GKEYKCKVSN KALPAPIEKT

ISKAKGQPRE PQVYTLPPSR XEXTKNQVSL TCLVKGFYPS

DIAVEWESNG QPENNYKTTP PVLDSDGSFF LYSKLTVDKS

RWQQGNVFSC SVMHEALHNH YTQKSLSLSP GX.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcγR binding. The isolated antibody or antigen binding portion thereof described herein can have P238 mutated to lysine in a human IgG1 Fc domain.

The isolated antibody or antigen binding portion thereof comprises an Fc domain which comprises an amino acid sequence selected from: SEQ ID NOs: 22-29.

EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPG (SEQ ID NO: 22; IgG1-P238K (-C-term Lys)),

-continued

EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK (SEQ ID NO: 23; IgG1-P238K),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG (SEQ ID NO: 24; CH1-IgG1-P238K (-C-term Lys)),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 25; CH1-IgG1-P238K),

EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPG (SEQ ID NO: 26; IgG1f-P238K (-C-term Lys)),

EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK (SEQ ID NO: 27; IgG1f-P238K),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG (SEQ ID NO: 28; CH1-IgG1f-P238K (-C-term Lys)),

-continued or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID No: 29; CH1-IgG1f-P238K).

Exemplary sequences comprising the IgG1 Fc domains above include the four different VH chain sequences set forth in Table 12.

The isolated antibody or antigen binding portion thereof described herein can comprise a human IgG1 Fc domain comprising an alanine substituted at Kabat position 297. For example, the isolated antibody or antigen binding portion thereof comprises an Fc domain which comprises an amino acid sequence selected from: SEQ ID NOs: 141-148.

Exemplary heavy chain variable region and light chain variable region sequences of exemplary variants of BMS-986325 having improved PK are provided in Table 12. In these sequences, the heavy chain comprises an exemplary CH1 domain and a human IgG1 C domain comprising a mutation at Kabat position 238 that reduces binding to Fc-gamma-receptors (FcγRs), wherein proline 238 (P238) is mutated to one of the residues selected from the group consisting of lysine (K). The light chain comprises an exemplary CL domain

TABLE 12

| ID | VH Chain Sequence | VL Chain Sequence |
|---|---|---|
| Key: | CDRs are underlined<br>CDR1: amino acids 31-35<br>CDR2: amino acids 50-66<br>CDR3: amino acids 99-106<br>CH1 = amino acids 118-215 (italicized)<br>IgG1-P238K = amino acids 216-446)<br>P238K underlined<br>C-terminal lysine is optional | CDRs are underlined<br>CDR1: amino acids 24-34<br>CDR2: amino acids 50-56<br>CDR3: amino acids 89-97<br>CL = amino acids 108-214 (italicized) |
| | HC1 (wt) | LC4 (K45Q, R54Q, R61Q) |
| M49 | QVQLVQSGAEVKKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRVEP<br>KSCDKTHTCPPCPAPELLGGKSVFLFP<br>PKPKDTLMISRTPEVTCVVVDVSHEDP<br>EVKFNWYVDGVEVHNAKTKPREEQY<br>NSTYRVVSVLTVLHQDWLNGKEYKC<br>KVSNKALPAPIEKTISKAKGQPREPQV<br>YTLPPSRDELTKNQVSLTCLVKGFYPS<br>DIAVEWESNGQPENNYKTTPPVLDSD<br>GSFFLYSKLTVDKSRWQQGNVFSCSV<br>MHEALHNHYTQKSLSLSPGK<br>(SEQ ID NO: 1) | DIQMTQSPSFLSASVGDRVTITCKASQ<br>DVSTAVAWYQQKPGKAPQLLIYSASY<br>QYTGVPSQFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 20)<br>K45Q, R54Q, R61Q: bolded underlined |
| | HC1 (wt) | LC3 (K45E) |
| M33 | QVQLVQSGAEVKKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRVEP<br>KSCDKTHTCPPCPAPELLGGKSVFLFP<br>PKPKDTLMISRTPEVTCVVVDVSHEDP<br>EVKFNWYVDGVEVHNAKTKPREEQY<br>NSTYRVVSVLTVLHQDWLNGKEYKC<br>KVSNKALPAPIEKTISKAKGQPREPQV<br>YTLPPSRDELTKNQVSLTCLVKGFYPS<br>DIAVEWESNGQPENNYKTTPPVLDSD<br>GSFFLYSKLTVDKSRWQQGNVFSCSV<br>MHEALHNHYTQKSLSLSPGK<br>(SEQ ID NO: 1) | DIQMTQSPSFLSASVGDRVTITCKASQ<br>DVSTAVAWYQQKPGKAPELLIYSASY<br>RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| | HC15 (R67Q) | LC3 (K45E) |
| M47 | QVQLVQSGAEVKKPGSSVKVSCKASG<br>YAFTSYWMHWVRQAPGQGLEWMGQ | DIQMTQSPSFLSASVGDRVTITCKASQ<br>DVSTAVAWYQQKPGKAPELLIYSASY |

TABLE 12-continued

| ID | VH Chain Sequence | VL Chain Sequence |
|---|---|---|
| | INPTTGRSQYNEKFKTQVTITADKSTS<br>TAYMELSSLRSEDTAVYYCARWGLQP<br>FAYWGQGTLVTVSSASTKGPSVFPLAP<br>SSKSTSGGTAALGCLVKDYFPEPVTVSW<br>NSGALTSGVHTFPAVLQSSGLYSLSSVVT<br>VPSSSLGTQTYICNVNHKPSNTKVDKRVE<br>PKSCDKTHTCPPCPAPELLGGKSVFLF<br>PPKPKDTLMISRTPEVTCVVVDVSHED<br>PEVKFNWYVDGVEVHNAKTKPREEQ<br>YNSTYRVVSVLTVLHQDWLNGKEYK<br>CKVSNKALPAPIEKTISKAKGQPREPQ<br>VYTLPPSRDELTKNQVSLTCLVKGFYP<br>SDIAVEWESNGQPENNYKTTPPVLDS<br>DGSFFLYSKLTVDKSRWQQGNVFSCS<br>VMHEALHNHYTQKSLSLSPGK<br>(SEQ ID NO: 15)<br>R67Q: bolded underlined | RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| M4 | HC4 (K12E) | LC1 (wt) |
| | QVQLVQSGAEVEKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRVEP<br>KSCDKTHTCPPCPAPELLGGKSVFLFP<br>PKPKDTLMISRTPEVTCVVVDVSHEDP<br>EVKFNWYVDGVEVHNAKTKPREEQY<br>NSTYRVVSVLTVLHQDWLNGKEYKC<br>KVSNKALPAPIEKTISKAKGQPREPQV<br>YTLPPSRDELTKNQVSLTCLVKGFYPS<br>DIAVEWESNGQPENNYKTTPPVLDSD<br>GSFFLYSKLTVDKSRWQQGNVFSCSV<br>MHEALHNHYTQKSLSLSPGK<br>(SEQ ID No. 4)<br>K12E: bolded underlined | DIQMTQSPSFLSASVGDRVTITCKASQ<br>DVSTAVAWYQQKPGKAPKLLIYSASY<br>RYTGVPSRFSGSGSGTDFTLTISSLQPE<br>DFATYYCQQHYSTPWTFGGGTKVEIK<br>RTVAAPSVFIFPPSDEQLKSGTASVVCLL<br>NNFYPREAKVQWKVDNALQSGNSQESVT<br>EQDSKDSTYSLSSTLTLSKADYEKHKVYA<br>CEVTHQGLSSPVTKSFNRGEC<br>(SEQ ID NO. 17) |
| | HC4 (K12E) | LC3 (K45E) |
| M36 | QVQLVQSGAEVEKPGSSVKVSCKASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRVEP<br>KSCDKTHTCPPCPAPELLGGKSVFLFP<br>PKPKDTLMISRTPEVTCVVVDVSHEDP<br>EVKFNWYVDGVEVHNAKTKPREEQY<br>NSTYRVVSVLTVLHQDWLNGKEYKC<br>KVSNKALPAPIEKTISKAKGQPREPQV<br>YTLPPSRDELTKNQVSLTCLVKGFYPS<br>DIAVEWESNGQPENNYKTTPPVLDSD<br>GSFFLYSKLTVDKSRWQQGNVFSCSV<br>MHEALHNHYTQKSLSLSPGK<br>(SEQ ID No. 4)<br>K12E: bolded underlined | DIQMTQSPSFLSASVGDRVTITCKASQ<br>DVSTAVAWYQQKPGKAPELLIYSASY<br>RYTGVPSRFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 19)<br>K45E: bolded underlined |
| M53 | HC5 (K12E, K13Q, K23E) | LC4 (K45Q, R54Q, R61Q) |
| | QVQLVQSGAEVEQPGSSVKVSCEASG<br>YAFTSYWMHWVRQAPGQGLEWMGQ<br>INPTTGRSQYNEKFKTRVTITADKSTST<br>AYMELSSLRSEDTAVYYCARWGLQPF<br>AYWGQGTLVTVSSASTKGPSVFPLAPS<br>SKSTSGGTAALGCLVKDYFPEPVTVSWN<br>SGALTSGVHTFPAVLQSSGLYSLSSVVTV<br>PSSSLGTQTYICNVNHKPSNTKVDKRVEP<br>KSCDKTHTCPPCPAPELLGGKSVFLFP<br>PKPKDTLMISRTPEVTCVVVDVSHEDP<br>EVKFNWYVDGVEVHNAKTKPREEQY<br>NSTYRVVSVLTVLHQDWLNGKEYKC<br>KVSNKALPAPIEKTISKAKGQPREPQV<br>YTLPPSRDELTKNQVSLTCLVKGFYPS | DIQMTQSPSFLSASVGDRVTITCKASQ<br>DVSTAVAWYQQKPGKAPQLLIYSASY<br>QYTGVPSQFSGSGSGTDFTLTISSLQPE<br>DFATYYCQQHYSTPWTFGGGTKVEIK<br>RTVAAPSVFIFPPSDEQLKSGTASVVCLLN<br>NFYPREAKVQWKVDNALQSGNSQESVTE<br>QDSKDSTYSLSSTLTLSKADYEKHKVYAC<br>EVTHQGLSSPVTKSFNRGEC<br>(SEQ ID NO: 20)<br>K45Q, R54Q, R61Q: bolded underlined |

TABLE 12-continued

| ID | VH Chain Sequence | VL Chain Sequence |
|---|---|---|
| | DIAVEWESNGQPENNYKTTPPVLDSD<br>GSFFLYSKLTVDKSRWQQGNVFSCSV<br>MHEALHNHYTQKSLSLSPGK<br>(SEQ ID NO. 5)<br>K12E, K13Q, K23E: bolded underlined | |

The antigen binding portion thereof of any antibody disclosed herein, can be selected from the group consisting of Fv, Fab, F(ab')2, Fab', dsFv, scFv, $sc(Fv)_2$, diabodies, and scFv-Fc.

The antibody or antigen binding portion thereof disclosed herein can be an immunoconjugate, wherein the antibody or antigen-binding portion thereof is linked to a therapeutic agent.

The antibody or antigen binding portion thereof disclosed herein can be a bispecific antibody, wherein the antibody or antigen-binding portion thereof is linked to a second functional moiety having a different binding specificity than said antibody or antigen binding portion thereof.

The antibody or antigen binding portion thereof disclosed herein can further comprise an additional moiety.

The variable regions of the present antibodies may optionally be linked to an Fc domain by an "amino acid linker" or "linker." For example, the C-terminus of a variable heavy chain domain may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 92), and a linker comprising 2, 3, 4, or 5 copies of GGGGS (SEQ ID NOs: 93 to 96, respectively). Table 13 lists suitable linker sequences for use in the present disclosure.

TABLE 13

| Representative Linker Sequences | |
|---|---|
| GGGGS | SEQ ID NO: 92 |
| $(GGGGS)_2$ | SEQ ID NO: 93 |
| $(GGGGS)_3$ | SEQ ID NO: 94 |
| (GGGGS)4 | SEQ ID NO: 95 |
| $(GGGGS)_5$ | SEQ ID NO: 96 |
| AST | SEQ ID NO: 97 |
| TVAAPS | SEQ ID NO: 98 |
| TVA | SEQ ID NO: 99 |
| ASTSGPS | SEQ ID NO: 100 |

Antibody Preparation

The antibody can be produced and purified using ordinary skill in a suitable mammalian host cell line, such as CHO, 293, COS, NSO, and the like, followed by purification using one or a combination of methods, including protein A affinity chromatography, ion exchange, reverse phase techniques, or the like.

As well known in the art, multiple codons can encode the same amino acid. Nucleic acids encoding a protein sequence thus include nucleic acids having codon degeneracy. The polypeptide sequences disclosed herein can be encoded by a variety of nucleic acids. The genetic code is universal and well known. Nucleic acids encoding any polypeptide sequence disclosed herein can be readily conceived based on conventional knowledge in the art as well as optimized for production. While the possible number of nucleic acid sequence encoding a given polypeptide is large, given a standard table of the genetic code, and aided by a computer, the ordinarily skilled artisan can easily generate every possible combination of nucleic acid sequences that encode a given polypeptide.

Representative nucleic acid sequences encoding four of the heavy chain variable domains are provided below. In these sequences, nucleotides 1-351 encode the heavy chain variable region in which nucleotides 91-105 encode CDR1, nucleotides 148-195 encode CDR2, and nucleotides 295-318_encode CDR3 of the variable domain of the heavy chain. Nucleotides 352-645 encode a CH1 domain, and nucleotides 646-1341_encode IgG1-P238K. Nucleotides 1342-1344_are a stop codon.

A representative nucleic acid sequence encoding the heavy chain variable domain (HCl i.e., HC-wt) of M39 and M33 (CDRs are underlined) and including a constant region CH1 (italicized) and Fc domain IgG1-P238K is:

(SEQ ID NO: 101)

CAGGTGCAGCTGGTGCAGTCTGGTGCCGAGGTCAAAAAGCCAGGCTCCA

GCGTGAAGGTGAGCTGCAAGGCCTCTGGCTACGCTTTCACCTCTTATTG

GATGCACTGGGTGAGACAGGCTCCTGGACAGGGCCTGGAGTGGATGGGC

CAGATCAACCCAACCACCGGCAGAAGCCAGTACAATGAGAAGTTTAAGA

CCCGCGTGACCATCACAGCCGACAAGTCCACCAGCACAGCTTATATGGA

GCTGTCTTCCCTGAGGTCCGAGGATACAGCCGTGTACTATTGCGCTCGG

TGGGGCCTGCAGCCTTTCGCTTACTGGGGCCAGGGCACCCTGGTGACAG

TGAGCTCT*GCGTCGACCAAGGGCCCATCCGTGTTTCCACTGGCTCCCTC*

*CAGCAAGTCTACCTCCGGAGGAACAGCCGCTCTGGGATGTCTGGTGAAG*

*GACTACTTCCCAGAGCCCGTGACAGTGTCCTGGAACAGCGGCGCCCTGA*

*CCTCCGGCGTGCATACATTTCCAGCTGTGCTGCAGTCTTCCGGCCTGTA*

*CAGCCTGAGCTCTGTGGTGACCGTGCCCTCCAGCTCTCTGGGCACCCAG*

*ACATATATCTGCAACGTGAATCACAAGCCATCCAATACAAAGGTGGACA*

*AGAGGGTG*GAGCCCAAGAGCAGAGAAAAGACCCATACATGCCCACCTTG

-continued

```
TCCTGCTCCAGAGCTGCTGGGAGGCAAGAGCGTGTTCCTGTTTCCACCC
AAGCCCAAGGACACCCTGATGATCTCTCGGACCCCTGAGGTGACATGCG
TGGTGGTGGACGTGTCCCACGAGGACCCCGAGGTGAAGTTCAACTGGTA
CGTGGATGGCGTGGAGGTGCATAATGCTAAGACCAAGCCTAGGGAGGAG
CAGTACAACAGCACCTATCGGGTGGTGTCTGTGCTGACAGTGCTGCACC
AGGACTGGCTGAACGGCAAGGAGTATAAGTGCAAGGTGAGCAATAAGGC
CCTGCCCGCTCCTATCGAGAAGACCATCTCTAAGGCCAAGGGCCAGCCT
AGAGAGCCACAGGTGTACACACTGCCTCCAAGCCGCGACGAGCTGACCA
AGAACCAGGTGTCTCTGACATGTCTGGTGAAGGGCTTCTATCCCTCTGA
TATCGCTGTGGAGTGGGAGTCCAATGGCCAGCCTGAGAACAATTACAAG
ACCACACCCCCTGTGCTGGACTCTGATGGCTCCTTCTTTCTGTATTCCA
AGCTGACCGTGGATAAGAGCCGCTGGCAGCAGGGCAACGTGTTCTCCTG
TTCTGTGATGCACGAAGCACTGCACAACCATTACACCCAGAAAAGCCTG
TCACTGTCACCCGGAAAATGA.
```

A representative nucleic acid sequence encoding the heavy chain variable domain (HC-15) of M47 and including a constant region CH1 and Fc domain IgG1-P238K is:

```
                                              (SEQ ID NO: 102)
CAGGTGCAGCTGGTGCAGTCTGGGGCTGAAGTCAAGAAGCCAGGCTCCA
GCGTGAAGGTGAGCTGCAAGGCCTCTGGCTACGCTTTCACCTCCTATTG
GATGCACTGGGTGAGACAGGCTCCTGGACAGGGCCTGGAGTGGATGGGC
CAGATCAACCCAACCACAGGCCGCAGCCAGTACAATGAGAAGTTTAAGA
CCCAGGTGACCATCACAGCCGACAAGTCCACCAGCACAGCTTATATGGA
GCTGTCTTCCCTGAGATCTGAGGATACAGCCGTGTACTATTGCGCTCGC
TGGGGCCTGCAGCCTTTCGCTTACTGGGGCCAGGGCACCCTGGTGACAG
TGAGCTCTGCGTCGACCAAGGGCCCAAGCGTGTTTCCACTGGCTCCCTC
CAGCAAGTCTACCTCCGGAGGAACAGCCGCTCTGGGATGTCTGGTGAAG
GACTACTTCCCAGAGCCCGTGACAGTGTCCTGGAACAGCGGCGCCCTGA
CCAGCGGAGTGCATACATTTCCAGCTGTGCTGCAGTCTTCCGGCCTGTA
CTCTCTGAGCTCTGTGGTGACCGTGCCCTCCAGCTCTCTGGGCACCCAG
ACATATATCTGCAACGTGAATCACAAGCCAAGCAATACAAAGGTGGACA
AGAGGGTGGAGCCCAAGTCTTGTGATAAGACCCATACATGCCCACCTTG
TCCTGCTCCAGAGCTGCTGGGCGGCAAGTCCGTGTTCCTGTTTCCACCC
AAGCCCAAGGACACCCTGATGATCTCCAGGACCCCTGAGGTGACATGCG
TGGTGGTGGACGTGAGCCACGAGGACCCCGAGGTGAAGTTCAACTGGTA
CGTGGATGGCGTGGAGGTGCATAATGCTAAGACCAAGCCTAGGGAGGAG
CAGTACAACTCTACCTATCGGGTGGTGTCCGTGCTGACAGTGCTGCACC
AGGACTGGCTGAACGGCAAGGAGTATAAGTGCAAGGTGTCTAATAAGGC
CCTGCCCGCTCCTATCGAGAAGACCATCTCCAAGGCCAAGGGCCAGCCT
AGGGAGCCACAGGTGTACACACTGCCTCCATCTCGGGACGAGCTGACCA
AGAACCAGGTGTCCCTGACATGTCTGGTGAAGGGCTTCTATCCCTCCGA
```

-continued

```
TATCGCTGTGGAGTGGGAGAGCAATGGCCAGCCTGAGAACAATTACAAG
ACCACACCCCCTGTGCTGGACTCTGATGGCTCCTTCTTTCTGTATAGCA
AGCTGACCGTGGATAAGTCTCGGTGGCAGCAGGGCAACGTGTTCTCCTG
TTCTGTGATGCACGAAGCACTGCACAACCACTACACTCAGAAGTCACTG
TCACTGTCTCCTGGCAAATGA.
```

A representative nucleic acid sequence encoding the heavy chain variable domain (HC-4) of M4 and M36 and including a constant region CH1 and Fc domain IgG1-P238K is:

```
                                              (SEQ ID NO: 103)
CAGGTGCAGCTGGTGCAGTCCGGTGCCGAGGTCGAGAAGCCAGGCTCCA
GCGTGAAGGTGAGCTGCAAGGCCTCTGGCTACGCTTTCACCTCCTATTG
GATGCACTGGGTGAGACAGGCTCCTGGACAGGGCCTGGAGTGGATGGGC
CAGATCAACCCAACCACAGGCAGAAGCCAGTACAATGAGAAGTTTAAGA
CCCGCGTGACCATCACAGCCGACAAGTCCACCAGCACAGCTTATATGGA
GCTGTCTTCCCTGAGGTCTGAGGATACAGCCGTGTACTATTGCGCTCGG
TGGGGCCTGCAGCCTTTCGCTTACTGGGGCCAGGGCACCCTGGTGACAG
TGAGCTCTGCGTCGACCAAGGGCCCAAGCGTGTTTCCACTGGCTCCCTC
CAGCAAGTCTACCTCCGGAGGCACAGCCGCTCTGGGATGTCTGGTGAAG
GACTACTTCCCAGAGCCCGTGACAGTGTCCTGGAACAGCGGCGCCCTGA
CCAGCGGAGTGCATACATTTCCAGCTGTGCTGCAGTCTTCCGGCCTGTA
CTCTCTGAGCTCTGTGGTGACCGTGCCCTCCAGCTCTCTGGGCACCCAG
ACATATATCTGCAACGTGAATCACAAGCCAAGCAATACAAAGGTGGACA
AGAGGGTGGAGCCCAAGTCTTGTGATAAGACCCATACATGCCCACCTTG
TCCTGCTCCAGAGCTGCTGGGCGGCAAGTCCGTGTTCCTGTTTCCACCC
AAGCCCAAGGACACCCTGATGATCTCCCGGACCCCTGAGGTGACATGCG
TGGTGGTGGACGTGAGCCACGAGGACCCCGAGGTGAAGTTCAACTGGTA
CGTGGATGGCGTGGAGGTGCATAATGCTAAGACCAAGCCTAGGGAGGAG
CAGTACAACTCTACCTATCGGGTGGTGTCCGTGCTGACAGTGCTGCACC
AGGACTGGCTGAACGGCAAGGAGTATAAGTGCAAGGTGTCTAATAAGGC
CCTGCCCGCTCCTATCGAGAAGACCATCTCCAAGGCCAAGGGCCAGCCT
AGAGAGCCACAGGTGTACACACTGCCTCCATCTCGCGACGAGCTGACCA
AGAACCAGGTGTCCCTGACATGTCTGGTGAAGGGCTTCTATCCCTCCGA
TATCGCTGTGGAGTGGGAGAGCAATGGCCAGCCTGAGAACAATTACAAG
ACCACACCCCCTGTGCTGGACTCTGATGGCTCCTTCTTTCTGTATAGCA
AGCTGACCGTGGATAAGTCTCGCTGGCAGCAGGGCAACGTGTTCTCCTG
TTCTGTGATGCACGAAGCACTGCACAACCATTACACTCAGAAGTCACTG
TCACTGTCTCCTGGGAAATGA.
```

A representative nucleic acid sequence encoding the heavy chain variable domain (HC-5) of M53 and including a constant region CH1 and Fc domain IgG1-P238K is:

(SEQ ID NO: 104)
CAGGTGCAGCTGGTGCAGTCCGGTGCCGAGGTCGAGCAGCCAGGCTCCA
GCGTGAAGGTGAGCTGCGAGGCCTCTGGCTACGCTTTCACCTCCTATTG
GATGCACTGGGTGAGACAGGCTCCTGGACAGGGCCTGGAGTGGATGGGC
CAGATCAACCCAACCACAGGCAGAAGCCAGTACAATGAGAAGTTTAAGA
CCCGCGTGACCATCACAGCCGACAAGTCCACCAGCACAGCTTATATGGA
GCTGTCTTCCCTGAGGTCTGAGGATACAGCCGTGTACTATTGCGCTCGG
TGGGGCCTGCAGCCTTTCGCTTACTGGGGCCAGGGCACCCTGGTGACAG
TGAGCTCTGCGTCGACCAAGGGCCCAAGCGTGTTTCCACTGGCTCCCTC
CAGCAAGTCTACCTCCGGAGGCACAGCCGCTCTGGGATGTCTGGTGAAG
GACTACTTCCCAGAGCCCGTGACAGTGTCCTGGAACAGCGGCGCCCTGA
CCAGCGGAGTGCATACATTTCCAGCTGTGCTGCAGTCTTCCGGCCTGTA
CTCTCTGAGCTCTGTGGTGACCGTGCCCTCCAGCTCTCTGGGCACCCAG
ACATATATCTGCAACGTGAATCACAAGCCAAGCAATACAAAGGTGGACA
AGAGGGTGGAGCCCAAGTCTTGTGATAAGACCCATACATGCCCACCTTG
TCCTGCTCCAGAGCTGCTGGGCGGCAAGTCCGTGTTCCTGTTTCCACCC
AAGCCCAAGGACACCCTGATGATCTCCCGGACCCCTGAGGTGACATGCG
TGGTGGTGGACGTGAGCCACGAGGACCCCGAGGTGAAGTTCAACTGGTA
CGTGGATGGCGTGGAGGTGCATAATGCTAAGACCAAGCCTAGGGAGGAG
CAGTACAACTCTACCTATCGGGTGGTGTCCGTGCTGACAGTGCTGCACC
AGGACTGGCTGAACGGCAAGGAGTATAAGTGCAAGGTGTCTAATAAGGC
CCTGCCCGCTCCTATCGAGAAGACCATCTCCAAGGCCAAGGGCCAGCCT
AGAGAGCCACAGGTGTACACACTGCCTCCATCTCGCGACGAGCTGACCA
AGAACCAGGTGTCCCTGACATGTCTGGTGAAGGGCTTCTATCCCTCCGA
TATCGCTGTGGAGTGGGAGAGCAATGGCCAGCCTGAGAACAATTACAAG
ACCACACCCCCTGTGCTGGACTCTGATGGCTCCTTCTTTCTGTATAGCA
AGCTGACCGTGGATAAGTCTCGCTGGCAGCAGGGCAACGTGTTCTCCTG
TTCTGTGATGCACGAAGCACTGCACAACCATTACACTCAGAAGTCACTG
TCACTGTCTCCTGGGAAATGA.

Representative nucleic acid sequences encoding three of the light chain variable domains are provided below. In these sequences, nucleotides 1-321 encode the light chain variable region in which nucleotides 70-102 encode CDR1, nucleotides 148-168 encode CDR2, and nucleotides 265-291 encode CDR3. Nucleotides 322-642 encode a CL. Nucleotides 643-645 are a stop codon.

A representative nucleic acid sequence encoding the light chain variable domain (LC4) of M49 and M53 (CDRs are underlined) and including a constant region CL (italicized) is:

(SEQ ID NO: 105)
GACATTCAGATGACTCAGTCTCCCTCCTTCCTGTCAGCCTCTGTGGGCG
ACAGGGTGACCATCACATGCAAGGCTTCCCAGGATGTGAGCACCGCCGT
GGCTTGGTACCAGCAGAAGCCAGGCAAGGCCCCCCAGCTGCTGATCTAT
TCCGCCTCTTACCAGTATACCGGAGTGCCATCCCAGTTCTCCGGCAGCG
GCTCTGGAACAGACTTTACCCTGACAATCTCCAGCCTGCAGCCTGAGGA
TTTCGCCACCTACTATTGCCAGCAGCACTACAGCACCCCATGGACATTT
GGCGGCGGCACCAAGGTGGAGATCAAG*AGAACAGTGGCCGCTCCCAGCG*
*TGTTCATCTTTCCCCCTTCTGACGAGCAGCTGAAGTCTGGCACAGCTTC*
*CGTGGTGTGCCTGCTGAACAATTTCTACCCTCGCGAGGCCAAGGTGCAG*
*TGGAAGGTGGATAACGCTCTGCAGTCCGGCAATAGCCAGGAGTCTGTGA*
*CCGAGCAGGACTCCAAGGATAGCACATATTCTCTGTCTTCCACCCTGAC*
*ACTGTCCAAGGCCGACTACGAGAAGCATAAGGTGTATGCTTGTGAAGTC*
*ACCCACCAGGGGCTGAGTTCACCAGTCACAAAATCTTTCAATAGAGGGG*
*AATGT*TGA.

A representative nucleic acid sequence encoding the light chain variable domain (LC3) of M33, M47, and M36 and including a constant region CL is:

(SEQ ID NO: 106)
GACATTCAGATGACTCAGTCTCCCTCCTTCCTGTCAGCCTCTGTGGGCG
ACAGGGTGACCATCACATGCAAGGCTTCCCAGGATGTGAGCACCGCCGT
GGCTTGGTACCAGCAGAAGCCAGGCAAGGCCCCCGAGCTGCTGATCTAT
TCCGCCTCTTACAGGTATACCGGAGTGCCATCCCGGTTCTCCGGCAGCG
GCTCTGGAACAGACTTTACCCTGACAATCTCCAGCCTGCAGCCTGAGGA
TTTCGCCACCTACTATTGCCAGCAGCACTACAGCACCCCATGGACATTT
GGCGGCGGCACCAAGGTGGAGATCAAG*AGAACAGTGGCCGCTCCCAGCG*
*TGTTCATCTTTCCCCCTTCTGACGAGCAGCTGAAGTCTGGCACAGCTTC*
*CGTGGTGTGCCTGCTGAACAATTTCTACCCTCGCGAGGCCAAGGTGCAG*
*TGGAAGGTGGATAACGCTCTGCAGTCCGGCAATAGCCAGGAGTCTGTGA*
*CCGAGCAGGACTCCAAGGATAGCACATATTCTCTGTCTTCCACCCTGAC*
*ACTGTCCAAGGCCGACTACGAGAAGCATAAGGTGTATGCTTGTGAAGTC*
*ACCCACCAGGGGCTGAGTTCACCAGTCACAAAATCTTTCAATAGAGGGG*
*AATGT*TGA.

A representative nucleic acid sequence encoding the light chain variable domain (LC1 i.e. LC-wt) of M4 and including a constant region CL is:

(SEQ ID NO. 107)
GACATCCAGATGACCCAGTCCCCCTCCTTCCTGTCTGCCTCCGTGGGCG
ACAGAGTGACCATCACCTGTAAGGCTTCCCAGGATGTGAGCACAGCCGT
GGCTTGGTACCAGCAGAAGCCAGGCAAGGCCCCCAAGCTGCTGATCTAT
TCCGCCTCTTACAGGTATACCGGCGTGCCCTCTCGGTTCTCCGGCAGCG
GCTCTGGCACAGACTTTACCCTGACAATCTCCAGCCTGCAGCCTGAGGA

-continued

```
TTTCGCCACCTACTATTGCCAGCAGCACTACTCCACCCCATGGACATTT

GGCGGCGGCACCAAGGTGGAGATCAAGAGGACAGTGGCCGCTCCCAGCG

TGTTCATCTTTCCCCCTTCTGACGAGCAGCTGAAGTCTGGCACCGCTTC

CGTGGTGTGCCTGCTGAACAATTTCTACCCTCGGGAGGCCAAGGTGCAG

TGGAAGGTGGATAACGCTCTGCAGTCCGGCAATAGCCAGGAGTCTGTGA

CCGAGCAGGACTCCAAGGATAGCACATATTCTCTGTCTTCCACCCTGAC

ACTGTCCAAGGCCGATTACGAGAAGCACAAGGTGTATGCTTGCGAGGTG

ACCCATCAGGGCCTGAGCTCTCCCGTGACAAAGAGCTTTAACCGCGGCG

AGTGTTGA.
```

Exemplary coding sequences are summarized below in Table 14. The sequences are provided in the sequence listing.

TABLE 14

| Chain designation | Name | SEQ ID NO: |
|---|---|---|
| HC1 | HC-wt | 101 |
| HC2 | HC-K12Q, K13Q | 108 |
| HC3 | HC-K12Q, K13Q, K23Q | 109 |
| HC4 | HC-K12E | 103 |
| HC5 | HC-K12E, K13Q, K23E | 104 |
| HC6 | HC-K12V, K19S, K23A | 110 |
| HC7 | HC-K23E | 111 |
| HC8 | HC-R38Q, K63Q, R67Q | 112 |
| HC9 | HC-K63Q, R67E | 113 |
| HC10 | HC-R67E | 114 |
| HC11 | HC-R57E | 115 |
| HC12 | HC-R57E, K74Q | 116 |
| HC13 | HC-E46K, E62K | 117 |
| HC14 | HC-K74T | 121 |
| HC15 | HC-R67Q | 102 |
| HC16 | HC-K63Q | 122 |
| LC1 | LC-wt | 107 |
| LC2 | LC-K45Q | 123 |
| LC3 | LC-K45E | 106 |
| LC4 | LC-K45Q, R54Q, R61Q | 105 |
| LC5 | LC-R61Q | 124 |
| LC6 | LC-K107Q, R108Q | 125 |

The coding sequence for the heavy and/or light chain optionally may encode a signal peptide, such as MRAWIFFLLCLAGRALA (SEQ ID NO: 51), at the 5' end of the coding sequence. An exemplary nucleic acid coding sequence for this signal peptide is

```
                                         (SEQ ID NO: 32)
ATGAGGGCTTGGATCTTCTTTCTGCTCTGCCTGGCCGGGAGAGCGCTCG

CA.
```

Accordingly, a nucleic acid encoding an antibody disclosed herein is also contemplated. Such a nucleic acid may be inserted into a vector, such as a suitable expression vector, e.g., pHEN-1 (Hoogenboom et al. (1991) *Nucleic Acids Res.* 19: 4133-4137). Further provided is an isolated host cell comprising the vector and/or the nucleic acid.

The antibody of the disclosure can be produced and purified using only ordinary skill in any suitable mammalian host cell line, such as CHO (Chinese hamster ovary cells), 293 (human embryonic kidney 293 cells), COS cells, NSO cells, and the like, followed by purification using one or a combination of methods, including protein A affinity chromatography, ion exchange, reverse phase techniques, or the like.

Pharmaceutical Compositions and Methods of Treatment

A pharmaceutical composition comprises a therapeutically-effective amount of one or more antibodies of the present disclosure and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are known in the art. See, e.g., Remington, THE SCIENCE AND PRACTICE OF PHARMACY, A. Gennaro, et al., eds., 21st ed., Mack Publishing Co. (2005).

In certain embodiments, the pharmaceutical composition may be administered alone or in combination therapy, (i.e., simultaneously or sequentially) with an immuno-suppressive/immunomodulatory and/or anti-inflammatory agent. An exemplary type of agent is a cytotoxic T lymphocyte-associated protein 4 (CTLA4) mutant molecule. An exemplary CTLA4 mutant molecule is L104EA29Y-Ig (belatacept) which is a modified CTLA4-Ig. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

In certain embodiments, a method of treating an immune disease in a patient in need of such treatment may comprise administering to the patient a therapeutically effective amount of the antibody, or antigen binding portion thereof, as described herein. Further provided is a method of treating or preventing an autoimmune or inflammatory disease in a patient in need of such treatment may comprise administering to the patient a therapeutically effective amount of the antibody, or antigen binding portion thereof, as described herein. Also provided is the use of an antibody, or antigen binding portion thereof, of the disclosure, or a pharmaceutically acceptable salt thereof, for treating an immune disease in a patient in need of such treatment and/or for treating or preventing an autoimmune or inflammatory disease in a patient in need of such treatment, that may comprise administering to the patient a therapeutically effective amount of the antibody, or antigen binding portion thereof. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

In certain embodiments, the use of an antibody, or antigen binding portion thereof, of the disclosure, or a pharmaceutically acceptable salt thereof, in the preparation of a medicament for treatment of an immune disease and/or for treating or preventing an autoimmune or inflammatory disease in a patient in a patient in need of such treatment, is also provided. The medicament can, for example, be administered in combination with an immunosuppressive/immunomodulatory and/or anti-inflammatory agent.

As used herein, a "patient" means an animal, e.g., mammal, including a human. For example, the patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. Thus, the patient may be diagnosed with an autoimmune disease or inflammatory disease. An "autoimmune disease" refers to any disease associated with the development of an autoimmune reaction in an individual, including a cellular and/or a humoral immune reaction. An example of an autoimmune disease is inflammatory bowel disease (IBD), including, but not limited to ulcerative colitis and Crohn's disease. Other autoimmune diseases include systemic lupus erythematosus, multiple sclerosis, rheumatoid arthritis, diabetes, psoriasis, scleroderma, and atherosclerosis. Graft-related diseases include graft versus host disease (GVHD), acute transplantation rejection, and chronic transplantation rejection.

In certain embodiments, diseases that can be treated by administering the antibody of the disclosure may be selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Any suitable method or route can be used to administer the antibody, or antigen binding portion thereof, or the pharmaceutical composition. Routes of administration include, for example, intravenous, intraperitoneal, subcutaneous, or intramuscular administration. A therapeutically effective dose of administered antibody depends on numerous factors, including, for example, the type and severity of the disease being treated, the use of combination therapy, the route of administration of the antibody, or antigen binding portion thereof, or pharmaceutical composition, and the weight of the patient. A non-limiting range for a therapeutically effective amount of an antibody is 0.1-20 milligram/kilogram (mg/kg), and in an aspect, 1-10 mg/kg, relative to the body weight of the patient.

Kits

A kit useful for treating an immune disease in a human patient is provided. A kit useful for treating or preventing an autoimmune disease or inflammatory disease in a human patient is also provided. The kit can comprise (a) a dose of an antibody, or antigen binding portion thereof, of the present disclosure and (b) instructional material for using the antibody, or antigen binding portion thereof, in the method of treating an immune disease, or for using the antibody, or antigen binding portion thereof, in the method of treating or preventing an autoimmune or inflammatory disease, in a patient.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container that contains the compound and/or composition of the invention or be shipped together with a container, which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXEMPLARY EMBODIMENTS

Embodiment 1: An isolated antibody, or antigen binding portion thereof, that specifically binds to human CD40, wherein said antibody comprises a first polypeptide portion comprising a heavy chain variable region, and a second polypeptide portion comprising a light chain variable region, wherein:

(i) said heavy chain variable region comprises an amino acid sequence selected from: HC2, HC3, HC4, HC5, HC6, HC7, HC8, HC9, HC16, HC10, HC15, HC11, HC12, and HC 14; and said light chain variable region comprises LC1 as shown in Table 3;

TABLE 3

| | | | |
|---|---|---|---|
| | LC1 | LC-wt | DIQMTQSPSFLSASVGDRVTITCKASQDVSTAVAWYQQKP GKAPKLLIYSASYRYTGVPSRFSGSGSGTDFTLTISSLQP EDFATYYCQQHYSTPWTFGGGTKVEIK (SEQ ID NO: 45) |
| Combo # | | | |
| M2 | HC2 | HC-K12Q, K13Q | QVQLVQSGAEVQQPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 59) |
| M3 | HC3 | HC-K12Q, K13Q, K23Q | QVQLVQSGAEVQQPGSSVKVSCQASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 60) |
| M4 | HC4 | HC-K12E | QVQLVQSGAEVEKPGSSVKVSCKASGYAFTSYWMHWVRQA PGQGLEWMGQINPTTGRSQYNEKFKTRVTITADKSTSTAY |

TABLE 3-continued

| | | | |
|---|---|---|---|
| | | | MELSSLRSEDTAVYYCARWGLQPFAYWGQGTLVTVSS (SEQ ID NO: 44) |
| M5 | HC5 | HC-K12E, K13Q, K23E | QVQLVQSGAEVEQPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 46) |
| M6 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M7 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M8 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M9 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M16 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M10 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M15 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M11 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M12 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |
| M14 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |

(ii) said heavy chain variable region comprises an amino acid sequence selected from: HC1, HC2, HC3, HC4, HC5, HC6, HC7, HC8, HC9, HC16, HC10, HC15, HC11, HC12, and HC 14, and H13; and said light chain variable region comprises LC2 as shown in Table 4;

TABLE 4

| | | | |
|---|---|---|---|
| | LC2 | LC-K45Q | DIQMTQSPSFLSASVGDRVTITCKASQDVSTAVAWYQQKP GKAPQLLIYSASYRYTGVPSRFSGSGSGTDFTLTISSLQP EDFATYYCQQHYSTPWTFGGGTKVEIK (SEQ ID NO: 70) |
| Combo # | | | |
| M17 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |

TABLE 4-continued

| | | | |
|---|---|---|---|
| M18 | HC2 | HC-K12Q,<br>K13Q | QVQLVQSGAEVQQPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 59) |
| M19 | HC3 | HC-K12Q,<br>K13Q,<br>K23Q | QVQLVQSGAEVQQPGSSVKVSCQASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 60) |
| M20 | HC4 | HC-K12E | QVQLVQSGAEVEKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 44) |
| M21 | HC5 | HC-K12E,<br>K13Q,<br>K23E | QVQLVQSGAEVEQPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 46) |
| M22 | HC6 | HC-K12V,<br>K19S,<br>K23A | QVQLVQSGAEVVKPGSSVSVSCAASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 61) |
| M23 | HC7 | HC-K23E | QVQLVQSGAEVKKPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 62) |
| M24 | HC8 | HC-R38Q,<br>K63Q,<br>R67Q | QVQLVQSGAEVKKPGSSVKVSCKASGYAFTSYWMHWVQQA<br>PGQGLEWMGQINPTTGRSQYNEQFKTQVTITADKSTSTAY<br>MELSSLRSEDTAVYYCARWGLQPFAYWGQGTLVTVSS<br>(SEQ ID NO: 63) |
| M25 | HC9 | HC-K63Q,<br>R67E | QVQLVQSGAEVKKPGSSVKVSCKASGYAFTSYWMHWVRQA<br>PGQGLEWMGQINPTTGRSQYNEQFKTEVTITADKSTSTAY<br>MELSSLRSEDTAVYYCARWGLQPFAYWGQGTLVTVSS<br>(SEQ ID NO: 64) |
| M32 | HC16 | HC-K63Q | QVQLVQSGAEVKKPGSSVKVSCKASGYAFTSYWMHWVRQA<br>PGQGLEWMGQINPTTGRSQYNEQFKTRVTITADKSTSTAY<br>MELSSLRSEDTAVYYCARWGLQPFAYWGQGTLVTVSS<br>(SEQ ID NO: 65) |
| M26 | HC10 | HC-R67E | QVQLVQSGAEVKKPGSSVKVSCKASGYAFTSYWMHWVRQA<br>PGQGLEWMGQINPTTGRSQYNEKFKTEVTITADKSTSTAY<br>MELSSLRSEDTAVYYCARWGLQPFAYWGQGTLVTVSS<br>(SEQ ID NO: 66) |
| M31 | HC15 | HC-R67Q | QVQLVQSGAEVKKPGSSVKVSCKASGYAFTSYWMHWVRQA<br>PGQGLEWMGQINPTTGRSQYNEKFKTQVTITADKSTSTAY<br>MELSSLRSEDTAVYYCARWGLQPFAYWGQGTLVTVSS<br>(SEQ ID NO: 43) |
| M27 | HC11 | HC-R57E | QVQLVQSGAEVKKPGSSVKVSCKASGYAFTSYWMHWVRQA<br>PGQGLEWMGQINPTTGESQYNEKFKTRVTITADKSTSTAY<br>MELSSLRSEDTAVYYCARWGLQPFAYWGQGTLVTVSS<br>(SEQ ID NO: 67) |
| M28 | HC12 | HC-R57E,<br>K74Q | QVQLVQSGAEVKKPGSSVKVSCKASGYAFTSYWMHWVRQA<br>PGQGLEWMGQINPTTGESQYNEKFKTRVTITADQSTSTAY<br>MELSSLRSEDTAVYYCARWGLQPFAYWGQGTLVTVSS<br>(SEQ ID NO: 68) |
| M30 | HC14 | HC-K74T | QVQLVQSGAEVKKPGSSVKVSCKASGYAFTSYWMHWVRQA<br>PGQGLEWMGQINPTTGRSQYNEKFKTRVTITADTSTSTAY<br>MELSSLRSEDTAVYYCARWGLQPFAYWGQGTLVTVSS<br>(SEQ ID NO: 69) |
| M29 | HC13 | HC-E46K,<br>E62K | QVQLVQSGAEVKKPGSSVKVSCKASGYAFTSYWMHWVRQA<br>PGQGLKWMGQINPTTGRSQYNKKFKTRVTITADKSTSTAY<br>MELSSLRSEDTAVYYCARWGLQPFAYWGQGTLVTVSS<br>(SEQ ID NO: 71) |

(iii) said heavy chain variable region comprises an amino acid sequence selected from: HC1, HC2, HC3, HC4, HC5, HC6, HC7, HC8, HC9, HC16, HC10, HC15, HC11, HC12, and HC 14, and H13; and said light chain variable region comprises LC3 as shown in Table 5;

TABLE 5

| | | | |
|---|---|---|---|
| | LC3 | LC-K45E | DIQMTQSPSFLSASVGDRVTITCKASQDVSTAVAWYQQKP<br>GKAPELLIYSASYRYTGVPSRFSGSGSGTDFTLTISSLQP<br>EDFATYYCQQHYSTPWTFGGGTKVEIK<br>(SEQ ID NO: 42) |
| Combo # | | | |
| M33 | HC1 | HC-wt | QVQLVQSGAEVKKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 40) |
| M34 | HC2 | HC-K12Q,<br>K13Q | QVQLVQSGAEVQQPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 59) |
| M35 | HC3 | HC-K12Q,<br>K13Q,<br>K23Q | QVQLVQSGAEVQQPGSSVKVSCQASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 60) |
| M36 | HC4 | HC-K12E | QVQLVQSGAEVEKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 44) |
| M37 | HC5 | HC-K12E,<br>K13Q,<br>K23E | QVQLVQSGAEVEQPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 46) |
| M38 | HC6 | HC-K12V,<br>K19S,<br>K23A | QVQLVQSGAEVVKPGSSVSVSCAASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 61) |
| M39 | HC7 | HC-K23E | QVQLVQSGAEVKKPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 62) |
| M40 | HC8 | HC-R38Q,<br>K63Q,<br>R67Q | QVQLVQSGAEVKKPGSSVKVSCKASGYAFTSYWMHWVQQA<br>PGQGLEWMGQINPTTGRSQYNEQFKTQVTITADKSTSTAY<br>MELSSLRSEDTAVYYCARWGLQPFAYWGQGTLVTVSS<br>(SEQ ID NO: 63) |
| M41 | HC9 | HC-K63Q,<br>R67E | QVQLVQSGAEVKKPGSSVKVSCKASGYAFTSYWMHWVRQA<br>PGQGLEWMGQINPTTGRSQYNEQFKTEVTITADKSTSTAY<br>MELSSLRSEDTAVYYCARWGLQPFAYWGQGTLVTVSS<br>(SEQ ID NO: 64) |
| M48 | HC16 | HC-K63Q | QVQLVQSGAEVKKPGSSVKVSCKASGYAFTSYWMHWVRQA<br>PGQGLEWMGQINPTTGRSQYNEQFKTRVTITADKSTSTAY<br>MELSSLRSEDTAVYYCARWGLQPFAYWGQGTLVTVSS<br>(SEQ ID NO: 65) |
| M42 | HC10 | HC-R67E | QVQLVQSGAEVKKPGSSVKVSCKASGYAFTSYWMHWVRQA<br>PGQGLEWMGQINPTTGRSQYNEKFKTEVTITADKSTSTAY<br>MELSSLRSEDTAVYYCARWGLQPFAYWGQGTLVTVSS<br>(SEQ ID NO: 66) |
| M47 | HC15 | HC-R67Q | QVQLVQSGAEVKKPGSSVKVSCKASGYAFTSYWMHWVRQA<br>PGQGLEWMGQINPTTGRSQYNEKFKTQVTITADKSTSTAY<br>MELSSLRSEDTAVYYCARWGLQPFAYWGQGTLVTVSS<br>(SEQ ID NO: 43) |
| M43 | HC11 | HC-R57E | QVQLVQSGAEVKKPGSSVKVSCKASGYAFTSYWMHWVRQA<br>PGQGLEWMGQINPTTGESQYNEKFKTRVTITADKSTSTAY<br>MELSSLRSEDTAVYYCARWGLQPFAYWGQGTLVTVSS<br>(SEQ ID NO: 67) |

TABLE 5-continued

| | | | |
|---|---|---|---|
| M44 | HC12 | HC-R57E,<br>K74Q | QVQLVQSGAEVKKPGSSVKVSCKASGYAFTSYWMHWVRQA<br>PGQGLEWMGQINPTTGESQYNEKFKTRVTITADQSTSTAY<br>MELSSLRSEDTAVYYCARWGLQPFAYWGQGTLVTVSS<br>(SEQ ID NO: 68) |
| M46 | HC14 | HC-K74T | QVQLVQSGAEVKKPGSSVKVSCKASGYAFTSYWMHWVRQA<br>PGQGLEWMGQINPTTGRSQYNEKFKTRVTITADTSTSTAY<br>MELSSLRSEDTAVYYCARWGLQPFAYWGQGTLVTVSS<br>(SEQ ID NO: 69) |
| M45 | HC13 | HC-E46K,<br>E62K | QVQLVQSGAEVKKPGSSVKVSCKASGYAFTSYWMHWVRQA<br>PGQGLKWMGQINPTTGRSQYNKKFKTRVTITADKSTSTAY<br>MELSSLRSEDTAVYYCARWGLQPFAYWGQGTLVTVSS<br>(SEQ ID NO: 71) |

(iv) said heavy chain variable region comprises an amino acid sequence selected from: HC1, HC2, HC3, HC4, HC5, HC6, HC7, HC8, HC9, HC16, HC10, HC15, HC11, HC12, and HC 14, and H13; and said light chain variable region comprises LC4 as shown in Table 6;

TABLE 6

| | | | |
|---|---|---|---|
| | LC4 | LC-K45Q,<br>R54Q,<br>R61Q | DIQMTQSPSFLSASVGDRVTITCKASQDVSTAVAWYQQKP<br>GKAPQLLIYSASYQYTGVPSQFSGSGSGTDFTLTISSLQP<br>EDFATYYCQQHYSTPWTFGGGTKVEIK<br>(SEQ ID NO: 41) |
| Combo # | | | |
| M49 | HC1 | HC-wt | QVQLVQSGAEVKKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 40) |
| M50 | HC2 | HC-K12Q,<br>K13Q | QVQLVQSGAEVQQPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 59) |
| M51 | HC3 | HC-K12Q,<br>K13Q,<br>K23Q | QVQLVQSGAEVQQPGSSVKVSCQASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 60) |
| M52 | HC4 | HC-K12E | QVQLVQSGAEVEKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 44) |
| M53 | HC5 | HC-K12E,<br>K13Q,<br>K23E | QVQLVQSGAEVEQPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 46) |
| M54 | HC6 | HC-K12V,<br>K19S,<br>K23A | QVQLVQSGAEVVKPGSSVSVSCAASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 61) |
| M55 | HC7 | HC-K23E | QVQLVQSGAEVKKPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 62) |
| M56 | HC8 | HC-R38Q,<br>K63Q,<br>R67Q | QVQLVQSGAEVKKPGSSVKVSCKASGYAFTSYWMHWVQQA<br>PGQGLEWMGQINPTTGRSQYNEQFKTQVTITADKSTSTAY<br>MELSSLRSEDTAVYYCARWGLQPFAYWGQGTLVTVSS<br>(SEQ ID NO: 63) |
| M57 | HC9 | HC-K63Q,<br>R67E | QVQLVQSGAEVKKPGSSVKVSCKASGYAFTSYWMHWVRQA<br>PGQGLEWMGQINPTTGRSQYNEQFKTEVTITADKSTSTAY<br>MELSSLRSEDTAVYYCARWGLQPFAYWGQGTLVTVSS<br>(SEQ ID NO: 64) |

TABLE 6-continued

| | | | |
|---|---|---|---|
| M64 | HC16 | HC-K63Q | QVQLVQSGAEVKKPGSSVKVSCKASGYAFTSYWMHWVRQA<br>PGQGLEWMGQINPTTGRSQYNEQFKTRVTITADKSTSTAY<br>MELSSLRSEDTAVYYCARWGLQPFAYWGQGTLVTVSS<br>(SEQ ID NO: 65) |
| M58 | HC10 | HC-R67E | QVQLVQSGAEVKKPGSSVKVSCKASGYAFTSYWMHWVRQA<br>PGQGLEWMGQINPTTGRSQYNEKFKTEVTITADKSTSTAY<br>MELSSLRSEDTAVYYCARWGLQPFAYWGQGTLVTVSS<br>(SEQ ID NO: 66) |
| M63 | HC15 | HC-R67Q | QVQLVQSGAEVKKPGSSVKVSCKASGYAFTSYWMHWVRQA<br>PGQGLEWMGQINPTTGRSQYNEKFKTQVTITADKSTSTAY<br>MELSSLRSEDTAVYYCARWGLQPFAYWGQGTLVTVSS<br>(SEQ ID NO: 43) |
| M59 | HC11 | HC-R57E | QVQLVQSGAEVKKPGSSVKVSCKASGYAFTSYWMHWVRQA<br>PGQGLEWMGQINPTTGESQYNEKFKTRVTITADKSTSTAY<br>MELSSLRSEDTAVYYCARWGLQPFAYWGQGTLVTVSS<br>(SEQ ID NO: 67) |
| M60 | HC12 | HC-R57E,<br>K74Q | QVQLVQSGAEVKKPGSSVKVSCKASGYAFTSYWMHWVRQA<br>PGQGLEWMGQINPTTGESQYNEKFKTRVTITADQSTSTAY<br>MELSSLRSEDTAVYYCARWGLQPFAYWGQGTLVTVSS<br>(SEQ ID NO: 68) |
| M62 | HC14 | HC-K74T | QVQLVQSGAEVKKPGSSVKVSCKASGYAFTSYWMHWVRQA<br>PGQGLEWMGQINPTTGRSQYNEKFKTRVTITADTSTSTAY<br>MELSSLRSEDTAVYYCARWGLQPFAYWGQGTLVTVSS<br>(SEQ ID NO: 69) |
| M61 | HC13 | HC-E46K,<br>E62K | QVQLVQSGAEVKKPGSSVKVSCKASGYAFTSYWMHWVRQA<br>PGQGLKWMGQINPTTGRSQYNKKFKTRVTITADKSTSTAY<br>MELSSLRSEDTAVYYCARWGLQPFAYWGQGTLVTVSS<br>(SEQ ID NO: 71) |

(v) said heavy chain variable region comprises an amino acid sequence selected from: HC1, HC2, HC3, HC4, HC5, HC6, HC7, HC8, HC9, HC16, HC10, HC15, HC11, HC12, and HC 14, and H13; and said light chain variable region comprises LC5 as shown in Table 7;

TABLE 7

| | | | |
|---|---|---|---|
| | LC5 | LC-R61Q | DIQMTQSPSFLSASVGDRVTITCKASQDVSTAVAWYQQKP<br>GKAPKLLIYSASYRYTGVPSQFSGSGSGTDFTLTISSLQP<br>EDFATYYCQQHYSTPWTFGGGTKVEIK<br>(SEQ ID NO: 90) |
| Combo # | | | |
| M65 | HC1 | HC-wt | QVQLVQSGAEVKKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 40) |
| M66 | HC2 | HC-K12Q,<br>K13Q | QVQLVQSGAEVQQPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 59) |
| M67 | HC3 | HC-K12Q,<br>K13Q,<br>K23Q | QVQLVQSGAEVQQPGSSVKVSCQASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 60) |
| M68 | HC4 | HC-K12E | QVQLVQSGAEVEKPGSSVKVSCKASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 44) |
| M69 | HC5 | HC-K12E,<br>K13Q,<br>K23E | QVQLVQSGAEVEQPGSSVKVSCEASGYAFTSYWMHWVRQA<br>PGQGLEWMGQINPTTGRSQYNEKFKTRVTITADKSTSTAY<br>MELSSLRSEDTAVYYCARWGLQPFAYWGQGTLVTVSS<br>(SEQ ID NO: 46) |

TABLE 7-continued

| | | | |
|---|---|---|---|
| M70 | HC6 | HC-K12V, K19S, K23A | QVQLVQSGAEVVKPGSSVSVSCAASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 61) |
| M71 | HC7 | HC-K23E | QVQLVQSGAEVKKPGSSVKVSCEASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 62) |
| M72 | HC8 | HC-R38Q, K63Q, R67Q | QVQLVQSGAEVKKPGSSVKVSCKASGYAFTSYWMHWVQQA PGQGLEWMGQINPTTGRSQYNEQFKTQVTITADKSTSTAY MELSSLRSEDTAVYYCARWGLQPFAYWGQGTLVTVSS (SEQ ID NO: 63) |
| M73 | HC9 | HC-K63Q, R67E | QVQLVQSGAEVKKPGSSVKVSCKASGYAFTSYWMHWVRQA PGQGLEWMGQINPTTGRSQYNEQFKTEVTITADKSTSTAY MELSSLRSEDTAVYYCARWGLQPFAYWGQGTLVTVSS (SEQ ID NO: 64) |
| M80 | HC16 | HC-K63Q | QVQLVQSGAEVKKPGSSVKVSCKASGYAFTSYWMHWVRQA PGQGLEWMGQINPTTGRSQYNEQFKTRVTITADKSTSTAY MELSSLRSEDTAVYYCARWGLQPFAYWGQGTLVTVSS (SEQ ID NO: 65) |
| M74 | HC10 | HC-R67E | QVQLVQSGAEVKKPGSSVKVSCKASGYAFTSYWMHWVRQA PGQGLEWMGQINPTTGRSQYNEKFKTEVTITADKSTSTAY MELSSLRSEDTAVYYCARWGLQPFAYWGQGTLVTVSS (SEQ ID NO: 66) |
| M79 | HC15 | HC-R67Q | QVQLVQSGAEVKKPGSSVKVSCKASGYAFTSYWMHWVRQA PGQGLEWMGQINPTTGRSQYNEKFKTQVTITADKSTSTAY MELSSLRSEDTAVYYCARWGLQPFAYWGQGTLVTVSS (SEQ ID NO: 43) |
| M75 | HC11 | HC-R57E | QVQLVQSGAEVKKPGSSVKVSCKASGYAFTSYWMHWVRQA PGQGLEWMGQINPTTGESQYNEKFKTRVTITADKSTSTAY MELSSLRSEDTAVYYCARWGLQPFAYWGQGTLVTVSS (SEQ ID NO: 67) |
| M76 | HC12 | HC-R57E, K74Q | QVQLVQSGAEVKKPGSSVKVSCKASGYAFTSYWMHWVRQA PGQGLEWMGQINPTTGESQYNEKFKTRVTITADQSTSTAY MELSSLRSEDTAVYYCARWGLQPFAYWGQGTLVTVSS (SEQ ID NO: 68) |
| M78 | HC14 | HC-K74T | QVQLVQSGAEVKKPGSSVKVSCKASGYAFTSYWMHWVRQA PGQGLEWMGQINPTTGRSQYNEKFKTRVTITADTSTSTAY MELSSLRSEDTAVYYCARWGLQPFAYWGQGTLVTVSS (SEQ ID NO: 69) |
| M77 | HC13 | HC-E46K, E62K | QVQLVQSGAEVKKPGSSVKVSCKASGYAFTSYWMHWVRQA PGQGLKWMGQINPTTGRSQYNKKFKTRVTITADKSTSTAY MELSSLRSEDTAVYYCARWGLQPFAYWGQGTLVTVSS (SEQ ID NO: 71) |

or (vi) said heavy chain variable region comprises an amino acid sequence selected from: HC1, HC2, HC3, HC4, HC5, HC6, HC7, HC8, HC9, HC16, HC10, HC15, HC11, HC12, and HC 14, and H13; and said light chain variable region comprises LC6 as shown in Table 8;

TABLE 8

| | | | |
|---|---|---|---|
| | LC6 | LC-K107Q, R108Q | DIQMTQSPSFLSASVGDRVTITCKASQDVSTAVAWYQQKP GKAPKLLIYSASYRYTGVPSRFSGSGSGTDFTLTISSLQP EDFATYYCQQHYSTPWTFGGGTKVEI**QQ** (SEQ ID NO: 72) |
| Combo # | | | |
| M81 | HC1 | HC-wt | QVQLVQSGAEVKKPGSSVKVSCKASGYAFTSYWMHWVRQA PGQGLEWMGQINPTTGRSQYNEKFKTRVTITADKSTSTAY MELSSLRSEDTAVYYCARWGLQPFAYWGQGTLVTVSS (SEQ ID NO: 40) |

TABLE 8-continued

| | | | |
|---|---|---|---|
| M82 | HC2 | HC-K12Q, K13Q | QVQLVQSGAEVQQPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 59) |
| M83 | HC3 | HC-K12Q, K13Q, K23Q | QVQLVQSGAEVQQPGSSVKVSCQASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 60) |
| M84 | HC4 | HC-K12E | QVQLVQSGAEVEKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 44) |
| M85 | HC5 | HC-K12E, K13Q, K23E | QVQLVQSGAEVEQPGSSVKVSCEASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 46) |
| M86 | HC6 | HC-K12V, K19S, K23A | QVQLVQSGAEVVKPGSSVSVSCAASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 61) |
| M87 | HC7 | HC-K23E | QVQLVQSGAEVKKPGSSVKVSCEASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 62) |
| M88 | HC8 | HC-R38Q, K63Q, R67Q | QVQLVQSGAEVKKPGSSVKVSCKASGYAFTSYWMHWVQQAPGQGLEWMGQINPTTGRSQYNEQFKTQVTITADKSTSTAYMELSSLRSEDTAVYYCARWGLQPFAYWGQGTLVTVSS (SEQ ID NO: 63) |
| M89 | HC9 | HC-K63Q, R67E | QVQLVQSGAEVKKPGSSVKVSCKASGYAFTSYWMHWVRQAPGQGLEWMGQINPTTGRSQYNEQFKTEVTITADKSTSTAYMELSSLRSEDTAVYYCARWGLQPFAYWGQGTLVTVSS (SEQ ID NO: 64) |
| M96 | HC16 | HC-K63Q | QVQLVQSGAEVKKPGSSVKVSCKASGYAFTSYWMHWVRQAPGQGLEWMGQINPTTGRSQYNEQFKTRVTITADKSTSTAYMELSSLRSEDTAVYYCARWGLQPFAYWGQGTLVTVSS (SEQ ID NO: 65) |
| M90 | HC10 | HC-R67E | QVQLVQSGAEVKKPGSSVKVSCKASGYAFTSYWMHWVRQAPGQGLEWMGQINPTTGRSQYNEKFKTEVTITADKSTSTAYMELSSLRSEDTAVYYCARWGLQPFAYWGQGTLVTVSS (SEQ ID NO: 66) |
| M95 | HC15 | HC-R67Q | QVQLVQSGAEVKKPGSSVKVSCKASGYAFTSYWMHWVRQAPGQGLEWMGQINPTTGRSQYNEKFKTQVTITADKSTSTAYMELSSLRSEDTAVYYCARWGLQPFAYWGQGTLVTVSS (SEQ ID NO: 43) |
| M91 | HC11 | HC-R57E | QVQLVQSGAEVKKPGSSVKVSCKASGYAFTSYWMHWVRQAPGQGLEWMGQINPTTGESQYNEKFKTRVTITADKSTSTAYMELSSLRSEDTAVYYCARWGLQPFAYWGQGTLVTVSS (SEQ ID NO: 67) |
| M92 | HC12 | HC-R57E, K74Q | QVQLVQSGAEVKKPGSSVKVSCKASGYAFTSYWMHWVRQAPGQGLEWMGQINPTTGESQYNEKFKTRVTITADQSTSTAYMELSSLRSEDTAVYYCARWGLQPFAYWGQGTLVTVSS (SEQ ID NO: 68) |
| M94 | HC14 | HC-K74T | QVQLVQSGAEVKKPGSSVKVSCKASGYAFTSYWMHWVRQAPGQGLEWMGQINPTTGRSQYNEKFKTRVTITADTSTSTAYMELSSLRSEDTAVYYCARWGLQPFAYWGQGTLVTVSS (SEQ ID NO: 69) |
| M93 | HC13 | HC-E46K, E62K | QVQLVQSGAEVKKPGSSVKVSCKASGYAFTSYWMHWVRQAPGQGLKWMGQINPTTGRSQYNKKFKTRVTITADKSTSTAYMELSSLRSEDTAVYYCARWGLQPFAYWGQGTLVTVSS (SEQ ID NO: 71) |

Embodiment 2. An isolated antibody, or antigen binding portion thereof, that specifically binds to human CD40, wherein said antibody comprises a first polypeptide portion comprising a heavy chain variable region, and a second polypeptide portion comprising a light chain variable region, wherein:

(i) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 40);

and said light chain variable region comprises LC4

(DIQMTQSPSFLSASVGDRVTITCKASQDVSTAVAWYQQKPGKAPQLLIYSASYQYTGVPSQFSGSGSGTDFTLTISSLQPEDFATYYCQQHYSTPWTFGGGTKVEIK; SEQ ID NO. 41);

(ii) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 40);

and said light chain variable region comprises LC3

(DIQMTQSPSFLSASVGDRVTITCKASQDVSTAVAWYQQKPGKAPELLIYSASYRYTGVPSRFSGSGSGTDFTLTISSLQPEDFATYYCQQHYSTPWTFGGGTKVEIK; SEQ ID NO. 42);

(iii) said heavy chain variable region comprises HC15

(QVQLVQSGAEVKKPGSSVKVSCKASGYAFTSYWMHWVRQAPGQGLEWMGQINPTTGRSQYNEKFKTQVTITADKSTSTAYMELSSLRSEDTAVYYCARWGLQPFAYWGQGTLVTVSS; SEQ ID NO. 43);

and said light chain variable region comprises LC3

(DIQMTQSPSFLSASVGDRVTITCKASQDVSTAVAWYQQKPGKAPELLIYSASYRYTGVPSRFSGSGSGTDFTLTISSLQPEDFATYYCQQHYSTPWTFGGGTKVEIK; SEQ ID NO. 42);

(iv) said heavy chain variable region comprises HC4

(QVQLVQSGAEVEKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 44);
and said light chain variable region comprises LC1

(DIQMTQSPSFLSASVGDRVTITCKASQDVSTAVAWYQQKPGKAPKLLIYSASYRYTGVPSRFSGSGSGTDFTLTISSLQPEDFATYYCQQHYSTPWTFGGGTKVEIK; SEQ ID NO. 45);

(v) said heavy chain variable region comprises HC4

(QVQLVQSGAEVEKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 44);
and said light chain variable region comprises LC3

(DIQMTQSPSFLSASVGDRVTITCKASQDVSTAVAWYQQKPGKAPELLIYSASYRYTGVPSRFSGSGSGTDFTLTISSLQPEDFATYYCQQHYSTPWTFGGGTKVEIK: SEQ ID NO. 42);

or (vi) said heavy chain variable region comprises HC5

(QVQLVQSGAEVEQPGSSVKVSCEASGYAFTSYWMHWVRQAPGQGLEWMGQINPTTGRSQYNEKFKTRVTITADKSTSTAYMELSSLRSEDTAVYYCARWGLQPFAYWGQGTLVTVSS; SEQ ID NO. 46);
and said light chain variable region comprises LC4

(DIQMTQSPSFLSASVGDRVTITCKASQDVSTAVAWYQQKPGKAPQLLIYSASYQYTGVPSQFSGSGSGTDFTLTISSLQPEDFATYYCQQHYSTPWTFGGGTKVEIK; SEQ ID NO. 41).

Embodiment 3. The isolated antibody, or antigen binding portion thereof, of embodiment 2, wherein said antibody comprises a first polypeptide portion comprising a heavy chain variable region, and a second polypeptide portion comprising a light chain variable region, wherein:

(i) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV*; SEQ ID NO. 47);
and said light chain variable region comprises LC4

(DIQMTQSPSFLSASVGDRVTITCKASQDVSTAVAWYQQKPGKAPQLLIYSASYQYTGVPSQFSGSGSGTDFTLTISSLQPEDFATYYCQQHYSTPWTFGGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*; SEQ ID NO. 20);

(ii) said heavy chain variable region comprises HC1

(QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV*; SEQ ID NO. 47);

-continued and said light chain variable region comprises LC3

(DIQMTQSPSFLSASVGDRVTITCKASQDVSTAVAWYQQKPGKAPELLI
YSASYRYTGVPSRFSGSGSGTDFTLTISSLQPEDFATYYCQQHYSTPWT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSYNTKSFNRGEC; SEQ ID NO. 19);

(iii) said heavy chain variable region comprises HC15

(QVQLVQSGAEVKKPGSSVKVSCKASGYAFTSYWMHWVRQAPGQGLEWM
GQINPTTGRSQYNEKFKTQVTITADKSTSTAYMELSSLRSEDTAVYYC
ARWGLQPFAYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKRV; SEQ ID NO. 86);

and said light chain variable region comprises LC3

(DIQMTQSPSFLSASVGDRVTITCKASQDVSTAVAWYQQKPGKAPEL
LIYSASYRYTGVPSRFSGSGSGTDFTLTISSLQPEDFATYYCQQHYSTP
WTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYA
CEVTHQGLSSYNTKSFNRGEC; SEQ ID NO. 19);

(iv) said heavy chain variable region comprises HC4

(QVQLVQSGAEVEKPGSSVKVSCKASGYAFTSYWMHWVRQAPGQGLEW
MGQINPTTGRSQYNEKFKTRVTITADKSTSTAYMELSSLRSEDTAVYYC
ARWGLQPFAYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKRV; SEQ ID NO. 49);

and said light chain variable region comprises LC1

(DIQMTQSPSFLSASVGDRVTITCKASQDVSTAVAWYQQKPGKAPKLLI
YSASYRYTGVPSRFSGSGSGTDFTLTISSLQPEDFATYYCQQHYSTPWT
FGGGTKVEIKRTVAAPSVFIFPPSDEQLKSGTASVVCLLNNFYPREAKV
QWKVDNALQSGNSQESVTEQDSKDSTYSLSSYETLSKADYEKHKVYACE
VTHQGLSSPVTKSFNRGEC; SEQ ID NO. 17);

(v) said heavy chain variable region comprises HC4

(QVQLVQSGAEVEKPGSSVKVSCKASGYAFTSYWMHWVRQAPGQGLEW
MGQINPTTGRSQYNEKFKTRVTITADKSTSTAYMELSSLRSEDTAVYYC
ARWGLQPFAYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKRV; SEQ ID NO. 49);

and said light chain variable region comprises LC3

(DIQMTQSPSFLSASVGDRVTITCKASQDVSTAVAWYQQKPGKAPEL
LIYSASYRYTGVPSRFSGSGSGTDFTLTISSLQPEDFATYYCQQHYSTP
WTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYA
CEVTHQGLSSYNTKSFNRGEC; SEQ ID NO. 19);

or (vi) said heavy chain variable region comprises HC5

(QVQLVQSGAEVEQPGSSVKVSCEASGYAFTSYWMHWVRQAPGQGLE
WMGQINPTTGRSQYNEKFKTRVTITADKSTSTAYMELSSLRSEDTAVYY
CARWGLQPFAYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKRV; SEQ ID NO. 50);

and said light chain variable region comprises LC4

(DIQMTQSPSFLSASVGDRVTITCKASQDVSTAVAWYQQKPGKAPQLL
IYSASYQYTGVPSQFSGSGSGTDFTLTISSLQPEDFATYYCQQHYST
PWTFGGGTKVEIKRTVAAPSVFIFPPSDEQLKSGTASVVCLLNNFYPRE
AKVQWKVDNALQSGNSQESVTEQDSKDSTYSLSSTLTLSKADYEKHKVY
ACEVTHQGLSSPVTKSFNRGEC; SEQ ID NO. 20).

Embodiment 4. The isolated antibody, or antigen binding portion thereof, of embodiment 2, wherein said first polypeptide portion comprises or consists of an amino acid sequence selected from the group consisting of:

(i)

QVQLVQSGAEVKKPGSSVKVSCKASGYAFTSYWMHWVRQAPGQGLEW
MGQINPTTGRSQYNEKFKTQVTITADKSTSTAYMELSSLRSEDTAV
YYCARWGLQPFAYWGQGTLVTVSSASTKGPSVFPLAPSSKSTSGGTA
ALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPEL
LGGKSVFLFPPKPKDTLMISRTPEVTCVVVDVSHEDPEVKFNWYVDG
VEVHNAKTKPREEQYNSTYRVVSVLTVLHQDWLNGKEYKCKVSNKAL
PAPIEKTISKAKGQPREPQVYTLPPSRDELTKNQVSLTCLVKGFYPS
DIAVEWESNGQPENNYKTTPPVLDSDGSFFLYSKLTVDKSRWQQGNV
FSCSVMHEALHNHYTQKSLSLSPG (HC15-P238K-no C-term lysine; SEQ ID NO: 35);

QVQLVQSGAEVEKPGSSVKVSCKASGYAFTSYWMHWVRQAPGQGLE
WMGQINPTTGRSQYNEKFKTRVTITADKSTSTAYMELSSLRSEDTAV
YYCARWGLQPFAYWGQGTLVTVSSASTKGPSVFPLAPSSKSTSGGTA
ALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPEL

-continued

LGGKSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPG (HC4-P238K-no C-term lysine; SEQ ID No. 36);

(iii)

QVQLVQSGAEVEQPGSSVKVSCEASGYAFTSYWMHWVRQAPGQG

LEWMGQINPTTGRSQYNEKFKTRVTITADKSTSTAYMELSSLRSEDT

AVYYCARWGLQPFAYWGQGTLVTVSS*ASTKGPSVFPLAPSSKSTSGG*

*TAALGCLVKDYFPEPVTVSWNSGALTSGVHTFPAVLQSSGLYSLSSV*

*VTVPSSSLGTQTYICNVNHKPSNTKVDKRV*EPKSCDKTHTCPPCPAP

ELLGGKSVFLFPPKPKDTLMISRTPEVTCVVVDVSHEDPEVKFNWYV

DGVEVHNAKTKPREEQYNSTYRVVSVLTVLHQDWLNGKEYKCKVSNK

ALPAPIEKTISKAKGQPREPQVYTLPPSRDELTKNQVSLTCLVKGFY

PSDIAVEWESNGQPENNYKTTPPVLDSDGSFFLYSKLTVDKSRWQQG

NVFSCSVMHEALHNHYTQKSLSLSPG (HC5-P238K; no C-term lysine); SEQ ID. 37).

Embodiment 5. The isolated antibody, or antigen binding portion thereof, of embodiment 2, wherein said antibody comprises a first polypeptide portion comprising a heavy chain variable region, and a second polypeptide portion comprising a light chain variable region, wherein:

(i) said heavy chain variable region comprises HC1

(QVQLVQSGAEVKKPGSSVKVSCKASGYAFTSYWMHWVRQAPGQGLE

WMGQINPTTGRSQYNEKFKTRVTITADKSTSTAYMELSSLRSEDTAV

YYCARWGLQPFAYWGQGTLVTVSS*ASTKGPSVFPLAPSSKSTSGGTA*

*ALGCLVKDYFPEPVTVSWNSGALTSGVHTFPAVLQSSGLYSLSSVVT*

*VPSSSLGTQTYICNVNHKPSNTKVDKRV*EPKSCDKTHTCPPCPAPEL

LGGKSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPG; HC1-P238K; no C-term lysine; SEQ ID NO. 38);
and said light chain variable region comprises LC4
(DIQMTQSPSFLSASVGDRVTITCKASQDVSTAVAWYQQKPGKAPQ

LLIYSASYQYTGVPSQFSGSGSGTDFTLTISSLQPEDFATYYCQQ

HYSTPWTFGGGTKVEIK*RTVAAPSVFIFPPSDEQLKSGTASVVCLL*

*NNFYPREAKVQWKVDNALQSGNSQESVTEQDSKDSTYSLSSTLTLS*

*KADYEKHKVYACEVTHQGLSSPVTKSFNRGEC*; SEQ ID NO. 20);

(ii) said heavy chain variable region comprises HC1

(QVQLVQSGAEVKKPGSSVKVSCKASGYAFTSYWMHWVRQAPGQGLE

WMGQINPTTGRSQYNEKFKTRVTITADKSTSTAYMELSSLRSEDTAV

YYCARWGLQPFAYWGQGTLVTVSS*ASTKGPSVFPLAPSSKSTSGGTA*

*ALGCLVKDYFPEPVTVSWNSGALTSGVHTFPAVLQSSGLYSLSSVVT*

*VPSSSLGTQTYICNVNHKPSNTKVDKRV*EPKSCDKTHTCPPCPAPEL

LGGKSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPG; HC1-P238K; no C-term lysine; SEQ ID NO. 38);
and said light chain variable region comprises LC3

(DIQMTQSPSFLSASVGDRVTITCKASQDVSTAVAWYQQKPGKAPE

LLIYSASYRYTGVPSRFSGSGSGTDFTLTISSLQPEDFATYYCQQH

YSTPWTFGGGTKVEIK*RTVAAPSVFIFPPSDEQLKSGTASVVCLLN*

*NFYPREAKVQWKVDNALQSGNSQESVTEQDSKDSTYSLSSTLTLSK*

*ADYEKHKVYACEVTHQGLSSYNTKSFNRGEC*; SEQ ID NO. 19);

(iii) said heavy chain variable region comprises HC15

(QVQLVQSGAEVEKPGSSVKVSCKASGYAFTSYWMHWVRQAPGQG

LEWMGQINPTTGRSQYNEKFKTRVTITADKSTSTAYMELSSLRSEDT

AVYYCARWGLQPFAYWGQGTLVTVSS*ASTKGPSVFPLAPSSKSTSGG*

*TAALGCLVKDYFPEPVTVSWNSGALTSGVHTFPAVLQSSGLYSLSSV*

*VTVPSSSLGTQTYICNVNHKPSNTKVDKRV*EPKSCDKTHTCPPCPAP

ELLGGKSVFLFPPKPKDTLMISRTPEVTCVVVDVSHEDPEVKFNWYV

DGVEVHNAKTKPREEQYNSTYRVVSVLTVLHQDWLNGKEYKCKVSNK

ALPAPIEKTISKAKGQPREPQVYTLPPSRDELTKNQVSLTCLVKGFY

PSDIAVEWESNGQPENNYKTTPPVLDSDGSFFLYSKLTVDKSRWQQG

NVFSCSVMHEALHNHYTQKSLSLSPG; HC15-P238K; no C-term lysine; SEQ ID NO. 39);
and said light chain variable region comprises LC3

(DIQMTQSPSFLSASVGDRVTITCKASQDVSTAVAWYQQKPGKAPEL

LIYSASYRYTGVPSRFSGSGSGTDFTLTISSLQPEDFATYYCQQHYS

TPWTFGGGTKVEIKR*TVAAPSVFIFPPSDEQLKSGTASVVCLLNNFY*

PREAKVQWKVDNALQSGNSQESVTEQDSKDSTYSLSSTLTLSKADYE

*KHKVYACEVTHQGLSSYNTKSFNRGEC*; SEQ ID NO. 19);

(iv) said heavy chain variable region comprises HC4

(QVQLVQSGAEVSKPGSSVKVSCKASGYAFTSYWMHWVRQAPGQGL

EWMGQINPTTGRSQYNEKFKTRVTITADKSTSTAYMELSSLRSEDT

-continued

AVYYCARWGLQPFAYWGQGYYNYNSS*ASTKGPSVFPLAPSSKSTSG*
*GTAALGCLVKDYFPEPVTVSWNSGALTSGVHTFPAVLQSSGLYSLS*
*SWTVPSSSLGTQTYICNVNHKPSNTKVDKRV*EPKSCDKYHACPPCP
APELLGGKSVFLFPPKPKDTLMISRTPEVTCVVVDVSHEDPEVKFN
WYVDGVEVHNAKTKPREEQYNSTYRVVSVLTVLHQDWLNGKEYKCK
VSNKALPAPIEKTISKAKGQPREPQVYTLPPSRDELTKNQVSLTCL
VKGFYPSDIAVEWESNGQPENNYKTTPPVLDSDGSFFLYSKLTVDK
SRWQQGNVFSCSVMHEALHNHYTQKSLSLSPG;
HC4-P238K; no C-term lysine; SEQ ID NO. 88);
and said light chain variable region comprises LC1
(DIQMTQSPSFLSASVGDRVTITCKASQDVSTAVAWYQQKPGKAPK
LLIYSASYRYTGVPSRFSGSGSGTDFTLTISSLQPEDFATYYCQQH
YSTPWTFGGGTKVEIK*RTVAAPSVFIFPPSDEQLKSGTASVNCLLN*
*NFYPREAKVQWKVDNALQSGNSQESVTEQDSKDSTYSLSSYETLSK*
*ADYEKHKVYACEVTHQGLSSPVTKSFNRGEC*; SEQ ID NO. 17);

(v) said heavy chain variable region comprises HC4

(QVQLVQSGAEVEKPGSSVKVSCKASGYAFTSYWMHWVRQAPGQGL
EWMGQINPTTGRSQYNEKFKTRVTITADKSTSTAYMELSSLRSEDT
AVYYCARWGLQPFAYWGQGYENYNSS*ASTKGPSVFPLAPSSKSTSG*
*GTAALGCLVKDYFPEPVTVSWNSGALTSGVHTFPAVLQSSGLYSLS*
*SWTVPSSSLGTQTYICNVNHKPSNTKVDKRV*EPKSCDKYHACPPCP
APELLGGKSVFLFPPKPKDTLMISRTPEVTCVVVDVSHEDPEVKFN
WYVDGVEVHNAKTKPREEQYNSTYRVVSVLTVLHQDWLNGKEYKCK
VSNKALPAPIEKTISKAKGQPREPQVYTLPPSRDELTKNQVSLTCL
VKGFYPSDIAVEWESNGQPENNYKTTPPVLDSDGSFFLYSKLTVDK
SRWQQGNVFSCSVMHEALHNHYTQKSLSLSPG;
HC4-P238K; no C-term lysine; SEQ ID NO. 88);
and said light chain variable region comprises LC3
(DIQMTQSPSFLSASVGDRVTITCKASQDVSTAVAWYQQKPGKAPE
LLIYSASYRYTGVPSRFSGSGSGTDFTLTISSLQPEDFATYYCQQH
YSTPWTFGGGTKVEIK*RTVAAPSVFIFPPSDEQLKSGTASWCLLNN*
*FYPREAKVQWKVDNALQSGNSQESVTEQDSKDSTYSLSSTLTLSKA*
*DYEKHKVYACEVTHQGLSSYNTKSFNRGEC;* SEQ ID NO. 19);

or (vi) said heavy chain variable region comprises HC5

(QVQLVQSGAEVEQPGSSVKVSCEASGYAFTSYWMHWVRQAPGQGL
EWMGQINPTTGRSQYNEKFKTRVTITADKSTSTAYMELSSLRSEDT
AVYYCARWGLQPFAYWGQGYYNYNSS*ASTKGPSVFPLAPSSKSTSG*
*GTAALGCLVKDYFPEPVTVSWNSGALTSGVHTFPAVLQSSGLYSLS*
*SWTVPSSSLGTQTYICNVNHKPSNTKVDKRV*EPKSCDKYHACPPCP
APELLGGKSVFLFPPKPKDTLMISRTPEVTCVVVDVSHEDPEVKFN

-continued

WYVDGVEVHNAKTKPREEQYNSTYRVVSVLTVLHQDWLNGKEYKCK
VSNKALPAPIEKTISKAKGQPREPQVYTLPPSRDELTKNQVSLTCL
VKGFYPSDIAVEWESNGQPENNYKTTPPVLDSDGSFFLYSKLTVDK
SRWQQGNVFSCSVMHEALHNHYTQKSLSLSPG;
HC5-P238K; No C-term lysine; SEQ ID NO. 89);
and said light chain variable region comprises LC4
(DIQMTQSPSFLSASVGDRVTITCKASQDVSTAVAWYQQKPGKAPQ
LLIYSASYQYTGVPSQFSGSGSGTDFTLTISSLQPEDFATYYCQQH
YSTPWTFGGGTKVEIK*RTVAAPSVFIFPPSDEQLKSGTASWCLLNN*
*FYPREAKVQWKVDNALQSGNSQESVTEQDSKDSTYSLSSTLTLSKA*
*DYEKHKVYACEVTHQGLSSPVTKSFNRGEC*; SEQ ID NO. 20).

Embodiment 6. The isolated antibody, or antigen binding portion thereof, of embodiment 2, wherein said heavy chain variable region comprises HC1 (QVQLVQSGAEVKKPGSSVKVSCKASGYAFTSYWMHWVRQAPGQGLEWMGQINPT TGRSQYNEKFKTRVTITADKSTSTAYMELSSLRSEDTAVYYCARWGLQPFAYWGQG TLVTVSS; SEQ ID NO. 40); and said light chain variable region comprises LC4 (DIQMTQSPSFLSASVGDRVTITCKASQDVSTAVAWYQQKPGKAPQLLIYSASYQYT GVPSQFSGSGSGTDFTLTISSLQPEDFATYYCQQHYSTPWTFGGGTKVEIK; SEQ ID NO. 41).

Embodiment 7. The isolated antibody, or antigen binding portion thereof, of embodiment 2, wherein said heavy chain variable region comprises HC1 (QVQLVQSGAEVKKPGSSVKVSCKASGYAFTSYWMHWVRQAPGQGLEWMGQINPT TGRSQYNEKFKTRVTITADKSTSTAYMELSSLRSEDTAVYYCARWGLQPFAYWGQG TLVTVSS; SEQ ID NO. 40); and said light chain variable region comprises LC3 (DIQMTQSPSFLSASVGDRVTITCKASQDVSTAVAWYQQKPGKAPELLIYSASYRYTG VPSRFSGSGSGTDFTLTISSLQPEDFATYYCQQHYSTPWTFGGGTKVEIK; SEQ ID NO. 42).

Embodiment 8. The isolated antibody, or antigen binding portion thereof, of embodiment 2, wherein said heavy chain variable region comprises HC15 (QVQLVQSGAEVKKPGSSVKVSCKASGYAFTSYWMHWVRQAPGQGLEWMGQINPT TGRSQYNEKFKTQVTITADKSTSTAYMELSSLRSEDTAVYYCARWGLQPFAYWGQG TLVTVSS; SEQ ID NO. 43); and said light chain variable region comprises LC3 (DIQMTQSPSFLSASVGDRVTITCKASQDVSTAVAWYQQKPGKAPELLIYSASYRYTG VPSRFSGSGSGTDFTLTISSLQPEDFATYYCQQHYSTPWTFGGGTKVEIK; SEQ ID NO. 42).

Embodiment 9. The isolated antibody, or antigen binding portion thereof, of embodiment 2, wherein said heavy chain variable region comprises HC4 (QVQLVQSGAEVEKPGSSVKVSCKASGYAFTSYWMHWVRQAPGQGLEWMGQINPT TGRSQYNEKFKTRVTITADKSTSTAYMELSSLRSEDTAVYYCARWGLQPFAYWGQG TLVTVSS; SEQ ID NO. 44); and said light chain variable region comprises LC1 (DIQMTQSPSFLSASVGDRVTITCKASQDVSTAVAWYQQKPGKAPKLLIYSASYRYT GVPSRFSGSGSGTDFTLTISSLQPEDFATYYCQQHYSTPWTFGGGTKVEIK; SEQ ID NO. 45).

Embodiment 10. The isolated antibody, or antigen binding portion thereof, of embodiment 2, wherein said heavy chain variable region comprises HC4 (QVQLVQSGAEVEKPGSSVKVSCKASGYAFTSYWMHWVRQAPGQGLEWMGQINPT TGRSQYNEKFKTRVTITADKSTSTAYMELSSLRSEDTAVYYCARWGLQPFAYWGQG TLVTVSS; SEQ ID NO. 44); and said light chain variable region comprises LC3 (DIQMTQSPSFLSASVGDRVTITCKASQDVSTAVAWYQQKPGKAPELLIYSASYRYTG VPSRFSGSGSGTDFTLTISSLQPEDFATYYCQQHYSTPWTFGGGTKVEIK; SEQ ID NO. 42).

Embodiment 11. The isolated antibody, or antigen binding portion thereof, of embodiment 2, wherein said heavy chain variable region comprises HC5 (QVQLVQSGAEVEQPGSSVKVSCEASGYAFTSYWMHWVRQAPGQGLEWMGQINPT TGRSQYNEKFKTRVTITADKSTSTAYMELSSLRSEDTAVYYCARWGLQPFAYWGQG TLVTVSS; SEQ ID NO. 46); and said light chain variable region comprises LC4 (DIQMTQSPSFLSASVGDRVTITCKASQDVSTAVAWYQQKPGKAPQLLIYSASYQYT GVPSQFSGSGSGTDFTLTISSLQPEDFATYYCQQHYSTPWTFGGGTKVEIK; SEQ ID NO. 41).

Embodiment 12. The antibody or antigen binding portion thereof of any of embodiments 2-11, wherein the antigen binding portion is an scFv-Fc.

Embodiment 13. The antibody or antigen binding portion thereof of any one of embodiments 2-12, wherein the antibody or antigen-binding portion thereof is linked to a therapeutic agent.

Embodiment 14. The antibody or antigen binding portion thereof of any one of embodiments 2-13, wherein the antibody or antigen-binding portion thereof is linked to a second functional moiety having a different binding specificity than said antibody or antigen binding portion thereof.

Embodiment 15. The antibody or antigen binding portion thereof of any one of embodiments 2-14, further comprising an additional moiety.

Embodiment 16. A method of treating or preventing an immune response in a subject comprising administering to the subject the antibody, or the antigen binding portion thereof, of any one of embodiments 2-15.

Embodiment 17. A method of treating or preventing an autoimmune or inflammatory disease in a subject, comprising administering to the subject the antibody, or the antigen binding portion thereof, of any one of embodiments 2-15.

Embodiment 18. The method of embodiment 16 or 17, wherein the antibody, or the antigen binding portion thereof is administered with an immunosuppressive/immunomodulatory and/or anti-inflammatory agent.

Embodiment 19. The method of embodiment 18, wherein said immunosuppressive/immunomodulatory and/or anti-inflammatory agent is a CTLA4 mutant molecule.

Embodiment 20. The method of embodiment 19, wherein said a CTLA4 mutant molecule L104EA29Y-Ig (belatacept).

Embodiment 21. The method of embodiment 16 or 17, wherein the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, an immune response to recombinant drug products (e.g., Factor VII in hemophiliacs), lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Embodiment 22. An isolated antibody, or antigen binding portion thereof, wherein said antibody comprises a first polypeptide portion comprising a heavy chain variable region, and a second polypeptide portion comprising a light chain variable region, wherein (i) said heavy chain variable region comprises the HC1 framework (QVQLVQSGAEVKKPGSSVKVSCKASGYAFTXXXXXWVRQAPGQGL
EWMGXXXXXXXXXXXXXXXXXRVTITADKSTSTAYMELSSLRSEDT
AVYYCARXXXXXXXXWGQGTLVTVSS; SEQ ID NO. 73)
or a mutation thereof; and said light chain variable region comprises the LC1 framework (DIQMTQSPSFLSASVGDRVTITCXXXXXXXXXXXWYQQKPGKAPK
LLIYXXXXXXXGVPSRFSGSGSGTDFTLTISSLQPEDFATYYCXXX
XXXXXXFGGGTKVEIK; SEQ ID NO. 74)
or a mutation thereof;

and wherein at least one of the heavy chain variable region and the light chain variable region comprises a mutation at a basic residue, wherein a heavy chain variable region mutation is selected from the group consisting of positions 12, 13, 19, 23, 38, 57, 63, 67, and 74, and combinations thereof, of SEQ ID NO: 73 and/or a light chain variable region mutation is selected from the group consisting of positions of 45, 54, 61, and 107, and combinations thereof, of SEQ ID NO: 74; and wherein the at least one mutation at a basic residue is a mutation to a neutral amino acid or to an acidic amino acid.

Embodiment 23. The isolated antibody or antigen binding portion thereof of embodiment 22, wherein the neutral amino acid is selected from glutamine, asparagine, valine, serine, alanine, and threonine.

Embodiment 24. The isolated antibody or antigen binding portion thereof of embodiment 22, wherein the acidic amino acid is selected from glutamate or aspartate.

Embodiment 25. The isolated antibody or antigen binding portion thereof of embodiment 22, wherein at least two mutations are present in the light chain variable region at basic residues selected from the group consisting of 45, 54, 61, and 107, and combinations thereof, of SEQ ID NO: 74.

Embodiment 26. The isolated antibody or antigen binding portion thereof of embodiment 22, wherein at least two mutations are present in the heavy chain variable region at basic residues selected from the group consisting of 12, 13, 19, 23, 38, 57, 63, 67, and 74 of SEQ ID NO: 73.

Embodiment 27. The isolated antibody or antigen binding portion thereof of embodiment 22, wherein said light chain variable region comprises the LC1 framework (DIQMTQSPSFLSASVGDRVTITCXXXXXXXXXXXWYQQKPGKAPKLLIY
XXXXXXXGVPSRFSGSGSGTDFTLTISSLQPEDFATYYCXXXXXXXXXFG
GGTKVEIKR; SEQ ID NO. 75)

or mutation thereof and wherein positions of 45, 54, 61, 107, and 108, and combinations thereof, can be mutated.

Embodiment 28. The isolated antibody or antigen binding portion thereof of embodiment 22, for specifically binding to human CD40.

Embodiment 29. A method for improving at least one pharmacokinetic property of a first antibody, the method comprising mutating a residue at at least one position selected from 12, 13, 19, 23, 38, 57, 63, 67, and 74, or combinations thereof, of SEQ ID NO: 73 and/or at at least one position selected from 45, 54, 61, and 107, or combinations thereof, of SEQ ID NO: 74 to produce a variant of the first antibody having at least one mutated residue and at least one improved pharmacokinetic property, relative to the non-modified first antibody.

Embodiment 30. The method of embodiment 29, wherein the first antibody specifically binds to human CD40.

Embodiment 31. An isolated antibody, or antigen binding portion thereof, wherein said antibody comprises a first polypeptide portion comprising a heavy chain variable region, and a second polypeptide portion comprising a light chain variable region, wherein:

(i) said heavy chain variable region comprises the HC1 framework (QVQLVQSGAEVKKPGSSVKVSCKASGYAFTXXXXXWVRQAPGQGL
EWMGXXXXXXXXXXXXXXXXXRVTITADKSTSTAYMELSSLRSEDT
AVYYCARXXXXXXXXXWGQGTLVTVSS; SEQ ID NO. 73);
and said light chain variable region comprises the LC4 framework (DIQMTQSPSFLSASVGDRVTITCXXXXXXXXXXXWYQQKPGKAPQ
LLIYXXXXQXXGVPSQFSGSGSGTDFTLTISSLQPEDFATYYCXXX
XXXXXXFGGGTKVEIK; SEQ ID NO. 80);

(ii) said heavy chain variable region comprises the HC1 framework (QVQLVQSGAEVKKPGSSVKVSCKASGYAFTXXXXXWVRQAPGQGL
EWMGXXXXXXXXXXXXXXXXXRVTITADKSTSTAYMELSSLRSEDT
AVYYCARXXXXXXXXXWGQGTLVTVSS; SEQ ID NO. 73);
and said light chain variable region comprises the LC3 framework (DIQMTQSPSFLSASVGDRVTITCXXXXXXXXXXXWYQQKPGKAPE
LLIYXXXXXXXGVPSRFSGSGSGTDFTLTISSLQPEDFATYYCXXX
XXXXXXFGGGTKVEIK; SEQ ID NO. 81);

(iii) said heavy chain variable region comprises the HC15 framework (QVQLVQSGAEVKKPGSSVKVSCKASGYAFTXXXXXWVRQAPGQGL
EWMGXXXXXXXXXXXXXXXXXQVTITADKSTSTAYMELSSLRSEDT
AVYYCARXXXXXXXXXWGQGTLVTVSS; SEQ ID NO. 76);
and said light chain variable region comprises the LC3 framework (DIQMTQSPSFLSASVGDRVTITCXXXXXXXXXXXWYQQKPGKAPE
LLIYXXXXXXXGVPSRFSGSGSGTDFTLTISSLQPEDFATYYCXXX
XXXXXXFGGGTKVEIK; SEQ ID NO. 81);

(iv) said heavy chain variable region comprises the HC4 framework (QVQLVQSGAEVEKPGSSVKVSCKASGYAFTXXXXXWVRQAPGQGL
EWMGXXXXXXXXXXXXXXXXXRVTITADKSTSTAYMELSSLRSEDT
AVYYCARXXXXXXXXXWGQGTLVTVSS; SEQ ID NO. 78);
and said light chain variable region comprises the LC1 framework (DIQMTQSPSFLSASVGDRVTITCXXXXXXXXXXXWYQQKPGKAPK
LLIYXXXXXXXGVPSRFSGSGSGTDFTLTISSLQPEDFATYYCXXX
XXXXXXFGGGTKVEIK; SEQ ID NO. 74);

(v) said heavy chain variable region comprises the HC4 framework (QVQLVQSGAEVEKPGSSVKVSCKASGYAFTXXXXXWVRQAPGQGL
EWMGXXXXXXXXXXXXXXXXXRVTITADKSTSTAYMELSSLRSEDT
AVYYCARXXXXXXXXXWGQGTLVTVSS; SEQ ID NO. 78);
and said light chain variable region comprises the LC3 framework (DIQMTQSPSFLSASVGDRVTITCXXXXXXXXXXXWYQQKPGKAPE
LLIYXXXXXXXGVPSRFSGSGSGTDFTLTISSLQPEDFATYYCXXX
XXXXXXFGGGTKVEIK; SEQ ID NO. 81);

or (vi) said heavy chain variable region comprises the HC5 framework (QVQLVQSGAEVEQPGSSVKVSCEASGYAFTXXXXXWVRQAPGQGLEW
MGXXXXXXXXXXXXXXXXXRVTITADKSTSTAYMELSSLRSEDTAVYYC
ARXXXXXXXXXWGQGTLVTVSS; SEQ ID NO. 79);
and said light chain variable region comprises the LC4 framework (DIQMTQSPSFLSASVGDRVTITCXXXXXXXXXXXWYQQKPGKAPQLL
IYXXXXQXXGVPSQFSGSGSGTDFTLTISSLQPEDFATYYCXXXXXXX
XXFGGGTKVEIK; SEQ ID NO. 80).

Embodiment 32. The isolated antibody or antigen binding portion thereof of embodiment 31, wherein said first polypeptide portion comprises a human heavy chain constant region; and said second polypeptide portion comprises a human light chain constant region.

Embodiment 33. A nucleic acid molecule encoding an isolated antibody or antigen binding portion thereof of any one of embodiments 1 to 15, 22 to 28, 31, and 32.

Embodiment 34. An expression vector comprising the nucleic acid molecule of embodiment 33.

Embodiment 35. A cell transformed with the expression vector of embodiment 34 or the nucleic acid of embodiment 33.

Embodiment 36. A method of preparing an anti-human CD40 antibody, or antigen binding portion thereof, comprising:

a) expressing the antibody, or antigen binding portion thereof, in the cell of embodiment 35; and b) isolating the antibody, or antigen binding portion thereof, from the cell.

Embodiment 37. A pharmaceutical composition comprising: a) the antibody, or antigen binding portion thereof, of any one of embodiments 1 to 15, 22 to 28, 31, and 32; and b) a pharmaceutically acceptable carrier.

Embodiment 38. An antibody, or antigen binding portion thereof, of any one of embodiments 1 to 15, 22 to 28, 31, and 32 for use as a medicament.

Embodiment 39. An antibody, or antigen binding portion thereof, of any one of embodiments 1 to 15, 22 to 28, 31, and 32 for use in the treatment of a subject in need thereof.

EXAMPLES

Example 1: Engineering BMS-986325 Variants for Improved Pharmacokinetic Properties Anti-CD40 monoclonal antibody BMS-986325 (PCT/US19/62011) was chosen for developing a protein engineering strategy to optimize pharmacokinetic (PK) properties. The amino acid sequence of the heavy chain variable region and the light chain variable region of BMS-986325 are shown in Table 15. The CDRs for each variable region are underlined and in bold font.

TABLE 15

| SEQ ID NO | ID | BMS-986325 variable regions |
|---|---|---|
| 40 | VH | QVQLVQSGAEVKKPGSSVKVSCKASGYAFT**SYWMH**WVRQAPGQGLEWMG**QINPTTGRSQYNEKFKT**RVTITADKSTSTAYMELSSLRSEDTAVYYCAR**WGLQPFAY**WGQGTLVTVSS |
| 45 | VL | DIQMTQSPSFLSASVGDRVTITC**KASQDVSTAVA**WYQQKPGKAPKLLIY**SASYRYT**GVPSRFSGSGSGTDFTLTISSLQPEDFATYYC**QQHYSTPWT**FGGGTKVEIK |

The protein engineering strategy was to disrupt positively charged (basic) patches on the antibody surface that might be involved in undesirable binding to negatively charged (acidic) intracellular surfaces, such as cell membranes or extracellular matrix (ECM). As part of this strategy, it was also critical to maintain the high affinity interactions with CD40 and functional potency, as well as the favorable biophysical properties of the antibody.

To limit potential immunogenicity risk, the initial optimization focused on the variable region of the heavy and light chains, which are naturally more prone to sequence variability. These variable heavy (Vh) and variable light (Vl) chain regions were analyzed at both the primary amino acid sequence level, as well as by generating a structural model of the BMS-986325 Fab domains. The homology model was created based on the available X-ray structures using the Antibody Modeler in Molecular Operating Environment (MOE) (Chemical Computing Group). The amino acid sequence was loaded into the modeling GUI. The tool then searches for framework and CDR loop templates. The antibody backbone is built from the most similar framework templates followed by CDR loop generation. The final step of model building is refinement performed by all atom minimization with Amber10EHT force field in MOE.

Sequence analysis first involved identifying all the lysine (Lys) and arginine (Arg) residues in the heavy chain variable region (Vh) and light chain variable region (Vl), which would be the primary source of positive charge at physiological pH and temperature. The location of these amino acid residues in BMS-986325 were evaluated with respect to the native human germline repertoire to identify residues that might have undergone mutation to improve CD40 binding, as well as evaluated with respect to a set of antibodies from the same sequence family that were identified from the same CD40 immunization that identified BMS-986325. See Table 16. (The light chain variable region for BMS-986325 is a kappa light chain "Vk").

TABLE 16

| Seq ID NO: | ID | VH or Vk Sequence |
|---|---|---|
| 33 | ADX_Y1256.ZZ0-1-Vh | QVQLQQSGAELAKPGSSVKMSCKASGYAFTSYWMHWVKQRPGQGLEWIGYINPTTGYSAYNQKFKDKATLTADKSSSTAYLQLTSLTSEDSAVYFCSRWGLPPFAYWGQGTLVTVSA |
| 34 | ADX_Y1257.ZZ0-1-Vh | QVQLQQSGAELAKPGSSVKMSCKASGYAFTSYWMHWVKQRPGQGLEWIGYINPTTGYSAYNQKFKAKTTLTADKSSSTAYMQLTSLTFEDSAVYFCSRWGLPPFAYWGQGTLVTVSA |
| 126 | ADX_Y1258.ZZ0-1-Vh | QVQLQQSGAELAKPGSSVKMSCKASGYAFTSYWMHWIKQRPGQGLEWIGFINPTTGYSEYNQKFKDKATLTADKSSSTAYMQLNSLTSEDSAVYFCARWGLPPFAYWGQGTLVTVSA |
| 127 | ADX_Y1259.ZZ0-1-Vh | QVQLQQSGAELAKPGASVKMSCKTSGYSFTSYWMHWIKQRPGQGLEWIGFINPTTGYTEYNQKFKDKATLTADKSSSTAYMQLSSLSSEDSAVYYCSRWGLPPFAYWGQGTLVTVSA |
| 128 | ADX_Y1260.ZZ0-1-Vh | QVQLQQSGAELTKPGASVKMSCKASGYSFTSYWMHWVKQRPGQGLEWIGSINPSTGYTEDNQKFKDKATLTADKSSTTAYMQLSSLTSEDSAVYYCARWGLPPFAYWGQGTLVTVSA |
| 129 | ADX_Y1261.ZZ0-1-Vh | QVQLQQSGAERAKPGASVKMSCKASGYSFTSYWMHWIKQRPGQGLEWIGFINPNTGHTDYNQKFKDKATLTADKSSSTAYMQLSSLTSEDSAVYFCSRWGLPPFAYWGQGTLVTVSA |
| 130 | ADX_Y1262.ZZ0-1-Vh | QVQLQQSGAELAKPGSSVKMSCKASGYAFTSYWMHWVKQRPGQGLEWIGYINPTTGYSAYNQKFKDKATLTADKSSSTAYMQLNSLTSEDSAVYYCARWDPRPFAYWGQGTLVTVSA |

TABLE 16-continued

| Seq ID NO: | ID | VH or Vk Sequence |
|---|---|---|
| 131 | ADX_Y1263.ZZ0-1-Vh | QVQLQQSGAELAKPGTSVKMSCKASGYSFTSYWVHWVKERPGQGLEWIGHTNPNTGYTEYNQKFKDKATLTVDRSSSTAYMQLNSLTSEDSAVYYCARWDPRPFAYWGQGTLVTVSA |
| 132 | ADX_Y1264.ZZ0-1-Vh | EVQLQQSGTVLARPGASVKMSCRASGYSFSSYWMHWVKQRPGQGLEWIGSINPGNSDAFYNQQFKGKAKLTAVTSASTAYMELSSLTNEDSAVYYCTRWGLPPFAYWGQGTLVTVSA |
| 133 | ADX_Y1265.ZZ0-1-Vh | EVQLQQSGTVLAGPGASVKMSCKASGYSFTSYWMHWVKQRPGQDLEWIGTINPGKGDSNYNQKFKGKAKLTAVTSASTAYMELSSLTNEDSAVYYCTRWGLPPFAYWGQGTLVTVSA |
| 134 | ADX_Y1266.ZZ0-1-Vh | QVQLQQPGAELVKPGASVRLSCKASGYSFTSYWMHWVKQRPGQGLEWIGQINPSNGRTQYNEKFKSMATLTVDKSSSTAYIQLSSLTSEDSAVYYCARWGLQPFAYWGQGTLVTVSA |
| 135 | ADX_Y1267.ZZ0-1-Vh | QVQLQQPGAELVKPGASVRLSCEASGYSFTSYWMHWVKQRPGQGLEWIGQINPSNGRTQYNEKFKSMATLTVDKSSSTAYIQLNSLTSEDSAVYYCARWGLQPFAYWGQGTLVTVSA |
| 136 | ADX_Y1268.ZZ0-1-Vh | QVQLQQPGAELVKPGASVRLSCKASGYAFTSYWMHWVKQRPGQGLEWIGQINPSNGRSQYNEKFKTMATLTVDKSSSTAYIQLSSLTSEDSAVYYCARWGLQPFAYWGQGTLVTVSA |
| 137 | ADX_Y1256.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1257.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1258.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1259.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1260.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1261.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 138 | ADX_Y1262.ZZ0-1-Vk | DIVMTQSHKFMSTSVGDRVSITCKASQDVSTAVAWYQQKPGQSPKLLIYSASYRYTGVPDRFTGSGYGTDFTFTISSVQAEDLAVYYCQQHYSTPWTFGGGTKLEIK |
| 137 | ADX_Y1263.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 139 | ADX_Y1264.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCHQHYSTPWTFGGGTKLEIK |
| 137 | ADX_Y1265.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 137 | ADX_Y1266.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |
| 140 | ADX_Y1267.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCLQHYTTPWTFGGGTKLEIK |
| 137 | ADX_Y1268.ZZ0-1-Vk | DIVMTQSHKFMSTSVGDRVSITCKASQDVSTAVAWYQQKPGQSPKLLIYSASYRYTGVPDRFTGSGSGTDFTFTISSVQAEDLAVYYCQQHYSTPWTFGGGTKLEIK |

The sequence analysis was used to help bias the protein engineering efforts away from residues that could potentially be involved in CD40 binding. Analysis of the structural model included: (1) evaluating the location of each of the Lys and Arg residues with respect to charged and hydrophobic patches on the antibody surface, and (2) evaluating the impact that mutation to non-basic residues would likely have on these surface properties. A charged patch refers to more than 1 charged residue in spatial proximity to each other on the surface of the folder protein structure. A hydrophobic patch refers to more than 1 non-charged residue in spatial proximity to each other on the surface of the folder protein structure In total, 7 Lys and 5 Arg residues were identified in the Vh sequence, and 6 Lys and 3 Arg in the Vl sequence of BMS-986325. In addition, since the last residue of the Vl (K107) and the first residue of the light chain constant region (R108) are basic residues, the R108 residue was considered as part of the substrate for mutation. Based on the above sequence and structural model analysis, each of the Lys and Arg residues were annotated with respect to: (1) their clustering into charge patches, (2) likelihood that mutation would impact binding based on (i) CDR proximity and (ii) binding data for sequence family variants, (3) germline analysis, and (4) other predicted properties based on structural modelling. See Table 17.

TABLE 17

Annotation of Lys and Arg residues selected in BMS-986325

| Chain | Residue | Charge patch/cluster | Priority | To test | Comments |
|---|---|---|---|---|---|
| HC | K12 | 3 | 1 | Y | Distinct positively charged patch. Very solvent exposed. Produce alone and in combo with other mutations. |
| HC | K13 | 3 | 1 | Y | Distinct positively charged patch. |
| HC | K19 | 3 | 1 | Y | Distinct positively charged patch. |
| HC | K23 | 3 | 1 | Y | Distinct positively charged patch. |
| HC | R38 | 2 | 2 | Y | Charge patch. Conserved Arg in human germlines. |
| HC | R57 | 1 | 2 | Y | Residue near CDR face. |
| HC | K63 | 2 | 3 | Y | Charge patch but in hCDR2. Conserved Lys in related antibodies from same immunization. |
| HC | K65 | 2 | 4 | N | In hCDR2 and not in distinct positively charged patch. |
| HC | R67 | 2 | 1 | Y | Charge patch. Edge of hCDR2. Related antibodies from same immunization have SPR data showing R67M can maintain target binding. This gives increased confidence in mutating R67 so will be central to combo mutant strategy for this patch. |
| HC | K74 | 1 | 2 | Y | Near CDRs and not in distinct positively charged patch. |
| HC | R87 | 2 | 4 | N | Not in distinct positively charge patch. |
| HC | R98 | none | 4 | N | Highly conserved Arg in "CAR" motif immediately before hCDR3 which is commonly critical for antibodies binding to targets. |
| LC | R18 | none | 4 | N | Not in distinct positively charged patch. |
| LC | K24 | none | 4 | N | In LCDR1 and not in distinct positively charged patch. |
| LC | K39 | 4 | 3 | N | Edge of positively charged patch #4, but closer to constant region. Deprioritized in favor of other patch 4 mutations. |
| LC | K42 | 4 | 3 | N | Edge of positively charged patch #4, but closer to constant region. Deprioritized in favor of other patch 4 mutations. |
| LC | K45 | 4 | 1 | Y | Positively charged patch. |
| LC | R54 | 4 | 3 | Y | Positively charged patch but in LCDR2. Make only as a combo mutant with other patch 4 mutations. |
| LC | R61 | 4 | 2 | Y | Positively charged patch. |
| LC | K103 | none | 4 | N | Poor solvent exposure and not in positively charged patch. |
| LC | K107 | 5 | 3 | Y | Connects V1 to C1 (together with R108). Lower priority but evaluate in combo with R108 mutation. |
| LC | R108 | 5 | 3 | Y | Connects V1 to C1 (together with K107). Lower priority but evaluate in combo with K107 mutation. |

The basic residues were mutated to either: (1) an uncharged amino acid or (2) an acidic residue. To select the amino acid residues to mutate the basic residues to, Gln was prioritized as an amino acid that would replace the basic side chain of Lys or Arg with an uncharged side chain of similar length. Glu was prioritized as an acidic residue that would result in a more dramatic disruption of a positively charged patch by reversing the positive charge of Lys or Arg with a negatively charged side chain of similar length. Gln and Glu were also prioritized over Asn and Asp residues respectively to avoid potential deamidation (Asn) or isomerization (Asp) issues that are common for the shorter Asn and Asp side chains. Glu and Gln were also prioritized since they have relatively low immunogenic potential. In addition, the Lys and Arg positions were compared across the human germline repertoire to identify alternative native germline residues that could replace the basic Lys or Arg side chain with neutral or acidic residues that are known to be structurally tolerated in other human IgG, and also likely to carry low immunogenicity risk.

Based on the above analysis each of Lys and Arg residues in the Vh and Vl regions were assigned a relative priority for mutagenesis, and then further consolidated into a short list of 14 mutant HC and 5 mutant LC consisting of single mutations or combinations of mutations that could represent a subset of the highest priority mutations. See Table 18 and Table 19.

TABLE 18

Antibody heavy chain and light chain sequences.

| SEQ ID NO: | HC# or LC# | HC or LC | Amino acid sequence |
|---|---|---|---|
| 1 | HC1 | HC-wt | QVQLVQSGAEVKKPGSSVKVSCKASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 2 | HC2 | HC-K12Q,K13Q | QVQLVQSGAEVQQPGSSVKVSCKASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 3 | HC3 | HC-K12Q,K13Q,K23Q | QVQLVQSGAEVQQPGSSVKVSCQASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 4 | HC4 | HC-K12E | QVQLVQSGAEVEKPGSSVKVSCKASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 5 | HC5 | HC-K12E,K13Q,K23E | QVQLVQSGAEVEQPGSSVKVSCEASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP |

TABLE 18-continued

Antibody heavy chain and light chain sequences.

| SEQ ID NO: | HC# or LC# | HC or LC | Amino acid sequence |
|---|---|---|---|
| | | | PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 6 | HC6 | HC-K12V,K19S,K23A | QVQLVQSGAEVVKPGSSVSVSCAASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 7 | HC7 | HC-K23E | QVQLVQSGAEVKKPGSSVKVSCEASGYAFTSYWMHWVRQAPGQG<br>LEWMGQINPTTGRSQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 8 | HC8 | HC-R38Q,K63Q,R67Q | QVQLVQSGAEVKKPGSSVKVSCKASGYAFTSYWMHWVQQAPGQG<br>LEWMGQINPTTGRSQYNEQFKTQVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 9 | HC9 | HC-K63Q,R67E | QVQLVQSGAEVKKPGSSVKVSCKASGYAFTSYWMHWVRQAPGQG<br>LEWMGQINPTTGRSQYNEQFKTEVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 10 | HC10 | HC-R67E | QVQLVQSGAEVKKPGSSVKVSCKASGYAFTSYWMHWVRQAPGQG<br>LEWMGQINPTTGRSQYNEKFKTEVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 11 | HC11 | HC-R57E | QVQLVQSGAEVKKPGSSVKVSCKASGYAFTSYWMHWVRQAPGQG<br>LEWMGQINPTTGESQYNEKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV |

TABLE 18-continued

Antibody heavy chain and light chain sequences.

| SEQ ID NO: | HC# or LC# | HC or LC | Amino acid sequence |
|---|---|---|---|
| | | | LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 12 | HC12 | HC-R57E,K74Q | QVQLVQSGAEVKKPGSSVKVSCKASGYAFTSYWMHWVRQAPGQG<br>LEWMGQINPTTGESQYNEKFKTRVTITADQSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 13 | HC13 | HC-E46K,E62K | QVQLVQSGAEVKKPGSSVKVSCKASGYAFTSYWMHWVRQAPGQG<br>LKWMGQINPTTGRSQYNKKFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 14 | HC14 | HC-K74T | QVQLVQSGAEVKKPGSSVKVSCKASGYAFTSYWMHWVRQAPGQG<br>LEWMGQINPTTGRSQYNEKFKTRVTITADTSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 15 | HC15 | HC-R67Q | QVQLVQSGAEVKKPGSSVKVSCKASGYAFTSYWMHWVRQAPGQG<br>LEWMGQINPTTGRSQYNEKFKTQVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 16 | HC16 | HC-K63Q | QVQLVQSGAEVKKPGSSVKVSCKASGYAFTSYWMHWVRQAPGQG<br>LEWMGQINPTTGRSQYNEQFKTRVTITADKSTSTAYMELSSLRS<br>EDTAVYYCARWGLQPFAYWGQGTLVTVSS*ASTKGPSVFPLAPSS*<br>*KSTSGGTAALGCLVKDYFPEPVTVSWNSGALTSGVHTFPAVLQS*<br>*SGLYSLSSVVTVPSSSLGTQTYICNVNHKPSNTKVDKRV*EPKSC<br>DKTHTCPPCPAPELLGGKSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| 17 | LC1 | LC-wt | DIQMTQSPSFLSASVGDRVTITCKASQDVSTAVAWYQQKPGKAP<br>KLLIYSASYRYTGVPSRFSGSGSGTDFTLTISSLQPEDFATYYC<br>QQHYSTPWTFGGGTKVEIK*RTVAAPSVFIFPPSDEQLKSGTASV*<br>*FCLLNNFYPREAKVQWKVDNALQSGNSQESVTEQDSKDSTYSLS*<br>*STLTLSKADYEKHKVYACEVTHQGLSSPVTKSFNRGEC* |
| 18 | LC2 | LC-K45Q | DIQMTQSPSFLSASVGDRVTITCKASQDVSTAVAWYQQKPGKAP<br>QLLIYSASYRYTGVPSRFSGSGSGTDFTLTISSLQPEDFATYYC<br>QQHYSTPWTFGGGTKVEIK*RTVAAPSVFIFPPSDEQLKSGTASV* |

TABLE 18-continued

Antibody heavy chain and light chain sequences.

| SEQ ID NO: | HC# or LC# | HC or LC | Amino acid sequence |
|---|---|---|---|
| | | | *VCLLNNFYPREAKVQWKVDNALQSGNSQESVTEQDSKDSTYSLS*<br>*STLTLSKADYEKHKVYACEVTHQGLSSPVTKSFNRGEC* |
| 19 | LC3 | LC-K45E | DIQMTQSPSFLSASVGDRVTITCKASQDVSTAVAWYQQKPGKAP<br>ELLIYSASYRYTGVPSRFSGSGSGTDFTLTISSLQPEDFATYYC<br>QQHYSTPWTFGGGTKVEIK*RTVAAPSVFIFPPSDEQLKSGTASV*<br>*VCLLNNFYPREAKVQWKVDNALQSGNSQESVTEQDSKDSTYSLS*<br>*STLTLSKADYEKHKVYACEVTHQGLSSPVTKSFNRGEC* |
| 20 | LC4 | LC-K45Q,R54Q, R61Q | DIQMTQSPSFLSASVGDRVTITCKASQDVSTAVAWYQQKPGKAP<br>QLLIYSASYQYTGVPSQFSGSGSGTDFTLTISSLQPEDFATYYC<br>QQHYSTPWTFGGGTKVEIK*RTVAAPSVFIFPPSDEQLKSGTASV*<br>*VCLLNNFYPREAKVQWKVDNALQSGNSQESVTEQDSKDSTYSLS*<br>*STLTLSKADYEKHKVYACEVTHQGLSSPVTKSFNRGEC* |
| 21 | LC5 | LC-R61Q | DIQMTQSPSFLSASVGDRVTITCKASQDVSTAVAWYQQKPGKAP<br>KLLIYSASYRYTGVPSQFSGSGSGTDFTLTISSLQPEDFATYYC<br>QQHYSTPWTFGGGTKVEIK*RTVAAPSVFIFPPSDEQLKSGTASV*<br>*VCLLNNFYPREAKVQWKVDNALQSGNSQESVTEQDSKDSTYSLS*<br>*STLTLSKADYEKHKVYACEVTHQGLSSPVTKSFNRGEC* |
| 30 | LC6 | LC-K107Q, R108Q | DIQMTQSPSFLSASVGDRVTITCKASQDVSTAVAWYQQKPGKAP<br>KLLIYSASYRYTGVPSRFSGSGSGTDFTLTISSLQPEDFATYYC<br>QQHYSTPWTFGGGTKVET*QQTVAAPSVFIFPPSDEQLKSGTASV*<br>*VCLLNNFYPREAKVQWKVDNALQSGNSQESVTEQDSKDSTYSLS*<br>*STLTLSKADYEKHKVYACEVTHQGLSSPVTKSFNRGEC* |

TABLE 19

Change in variable region net charge for different combinations of heavy chain and light chain.

| HC# | | | LC# LC1 | LC2 | LC3 | LC4 | LC5 | LC6 |
|---|---|---|---|---|---|---|---|---|
| | Construct | | LC-wt | LC-K45Q | LC-K45E | LC-K45Q, R54Q, R61Q | LC-R61Q | LC-K107Q, R108Q |
| | | Patch | | 4 | 4 | 4 | 4 | 5 |
| HC1 | HC-wt | | 0 | −1 | −2 | −3 | −1 | −2 |
| HC2 | HC-K12Q, K13Q | 3 | −2 | −3 | −4 | −5 | −3 | −4 |
| HC3 | HC-K12Q, K13Q, K23Q | 3 | −3 | −4 | −5 | −6 | −4 | −5 |
| HC4 | HC-K12E | 3 | −2 | −3 | −4 | −5 | −3 | −4 |
| HC5 | HC-K12E, K13Q, K23E | 3 | −5 | −6 | −7 | −8 | −6 | −7 |
| HC6 | HC-K12V, K19S, K23A | 3 | −3 | −4 | −5 | −6 | −4 | −5 |
| HC7 | HC-K23E | 3 | −2 | −3 | −4 | −5 | −3 | −4 |
| HC8 | HC-R38Q, K63Q, R67Q | 2 | −3 | −4 | −5 | −6 | −4 | −5 |
| HC9 | HC-K63Q, R67E | 2 | −3 | −4 | −5 | −6 | −4 | −5 |
| HC16 | HC-K63Q | 2 | −1 | −2 | −3 | −4 | −2 | −3 |
| HC10 | HC-R67E | 2 | −2 | −3 | −4 | −5 | −3 | −4 |
| HC15 | HC-R67Q | 2 | −1 | −2 | −3 | −4 | −2 | −3 |
| HC11 | HC-R57E | 1 | −2 | −3 | −4 | −5 | −3 | −4 |
| HC12 | HC-R57E, K74Q | 1 | −3 | −4 | −5 | −6 | −4 | −5 |
| HC14 | HC-K74T | 1 | −1 | −2 | −3 | −4 | −2 | −3 |
| HC13 | HC-E46K, E62K | 6 | 4 | 3 | 2 | 1 | 3 | 2 |

Moreover, one additional mutant HC (HC13) was designed as a proof of concept control, to replace two acidic residues with two basic residues (E46K, E62K) and introduce a more positively charged surface patch that would be predicted to potentially demonstrate increased off-target binding and reduced PK, i.e., the opposite properties to the other engineered variants.

Collectively these 15 mutant HC and 5 mutant LC together with the wild type HC and wild type LC resulted in a total of 16 HC and 6 LC constructs (TABLE 18) that could be combined in all possible HC×LC combinations to yield 96 unique antibodies. The overall change in net charge for these different combinations of HC and LC range from minus 8 (−8) for the combination of HC5 (HC-K12E, K13Q, K23E) with LC4 (LC-K45Q, R54Q, R61Q), to plus 4 (+4) for the proof of concept antibody combination of HC13 (HC-E46K, E62K) with the wild type LC1 (LC-wt). See Table 19.

Example 2: Titer Analysis of BMS-986325 Variant Supernatants

The 96 antibodies of the 16 HC×6 LC combinations were assigned antibody mutant identification numbers (M #) from M1-M96 (Table 20).

TABLE 20

Mutant identification numbers (M#) assigned to different combinations of heavy chain (HC) with light chain (LC).

| HC# | | | LC1 | LC2 | LC3 | LC4 | LC5 | LC6 |
|---|---|---|---|---|---|---|---|---|
| | Construct | | LC-wt | LC-K45Q | LC-K45E | LC-K45Q, R54Q, R61Q | LC-R61Q | LC-K107Q, R108Q |
| | | Patch | | 4 | 4 | 4 | 4 | 5 |
| HC1 | HC-wt | | M1 (wt) | M17 | M33 | M49 | M65 | M81 |
| HC2 | HC-K12Q, K13Q | 3 | M2 | M18 | M34 | M50 | M66 | M82 |
| HC3 | HC-K12Q, K13Q, K23Q | 3 | M3 | M19 | M35 | M51 | M67 | M83 |
| HC4 | HC-K12E | 3 | M4 | M20 | M36 | M52 | M68 | M84 |
| HC5 | HC-K12E, K13Q, K23E | 3 | M5 | M21 | M37 | M53 | M69 | M85 |
| HC6 | HC-K12V, K19S, K23A | 3 | M6 | M22 | M38 | M54 | M70 | M86 |
| HC7 | HC-K23E | 3 | M7 | M23 | M39 | M55 | M71 | M87 |
| HC8 | HC-R38Q, K63Q, R67Q | 2 | M8 | M24 | M40 | M56 | M72 | M88 |
| HC9 | HC-K63Q, R67E | 2 | M9 | M25 | M41 | M57 | M73 | M89 |
| HC16 | HC-K63Q | 2 | M16 | M32 | M48 | M64 | M80 | M96 |
| HC10 | HC-R67E | 2 | M10 | M26 | M42 | M58 | M74 | M90 |
| HC15 | HC-R67Q | 2 | M15 | M31 | M47 | M63 | M79 | M95 |
| HC11 | HC-R57E | 1 | M11 | M27 | M43 | M59 | M75 | M91 |
| HC12 | HC-R57E, K74Q | 1 | M12 | M28 | M44 | M60 | M76 | M92 |
| HC14 | HC-K74T | 1 | M14 | M30 | M46 | M62 | M78 | M94 |
| HC13 | HC-E46K, E62K | 6 | M13 | M29 | M45 | M61 | M77 | M93 |

The 96 antibodies generated from the 16 HC×6 LC combinations were produced by transient transfection and 3 mL scale, and analyzed for titer using ForteBio Octet RED96 instrument.

Antibody expression (titer) was detected for each HC×LC combination. The titer varied across a broad range from as low as 5 μg/ml (M56) to as high as 322 μg/ml (M80), with the wild type antibody (M1/wt) having a titer of 134 μg/ml. See Table 21.

TABLE 21

Antibody titer data in μg/ml as determined by Octet BLI analysis, for different combinations of heavy chain (HC) with light chain (LC).

| HC# | | | LC1 | LC2 | LC3 | LC4 | LC5 | LC6 |
|---|---|---|---|---|---|---|---|---|
| | Construct | | LC-wt | LC-K45Q | LC-K45E | LC-K45Q, R54Q, R61Q | LC-R61Q | LC-K107Q, R108Q |
| | | Patch | | 4 | 4 | 4 | 4 | 5 |
| HC1 | HC-wt | | 134 | 191 | 172 | 177 | 221 | 223 |
| HC2 | HC-K12Q, K13Q | 3 | 109 | 199 | 231 | 132 | 219 | 205 |
| HC3 | HC-K12Q, K13Q, K23Q | 3 | 81 | 170 | 179 | 128 | 220 | 200 |
| HC4 | HC-K12E | 3 | 86 | 188 | 251 | 151 | 241 | 220 |

TABLE 21-continued

Antibody titer data in μg/ml as determined by Octet BLI analysis, for different combinations of heavy chain (HC) with light chain (LC).

| HC# | | | LC# | | | | | |
|---|---|---|---|---|---|---|---|---|
| | | | LC1 | LC2 | LC3 | LC4 | LC5 | LC6 |
| HC5 | HC-K12E, K13Q, K23E | 3 | 58 | 112 | 146 | 87 | 161 | 125 |
| HC6 | HC-K12V, K19S, K23A | 3 | 80 | 134 | 295 | 108 | 314 | 163 |
| HC7 | HC-K23E | 3 | 116 | 172 | 232 | 143 | 190 | 224 |
| HC8 | HC-R38Q, K63Q, R67Q | 2 | 6 | 6 | 6 | 5 | 7 | 6 |
| HC9 | HC-K63Q, R67E | 2 | 46 | 38 | 71 | 36 | 99 | 57 |
| HC16 | HC-K63Q | 2 | 114 | 171 | 141 | 166 | 322 | 251 |
| HC10 | HC-R67E | 2 | 97 | 114 | 149 | 117 | 204 | 171 |
| HC15 | HC-R67Q | 2 | 116 | 197 | 198 | 174 | 245 | 210 |
| HC11 | HC-R57E | 1 | 135 | 167 | 39 | 124 | 152 | 171 |
| HC12 | HC-R57E, K74Q | 1 | 106 | 149 | 170 | 145 | 187 | 177 |
| HC14 | HC-K74T | 1 | 110 | 170 | 187 | 176 | 167 | 234 |
| HC13 | HC-E46K, E62K | 6 | 95 | 111 | 120 | 96 | 170 | 124 |

Several trends were observed in the titer data associated with specific HC or LC mutations. For example, the double or triple mutations to HC patch #2 (HC8=HC-R38Q, K63Q, R67Q, and HC9=HC-K63Q, R67E) significantly reduced the antibody titer in combination with any of the six LCs, with the triple mutant (HC8) demonstrating especially low titer (5-7 μg/ml) when paired with any of the six different LCs. Interestingly, the LC mutations generally improved the antibody titer, with 73/80 (91%) of antibodies that contained a mutated LC having higher titer than the respective HC paired with wild type LC. See Table 21.

Example 3: CD40 Binding SPR Analysis of BMS-986325 and Variant Supernatants

The 96 mutant BMS-986325 antibodies were tested for CD40 binding by surface plasmon resonance (SPR). The titer data (Table 21) were used to normalize the antibody concentration in each supernatant to 3 μg/ml, and these antibodies were captured out of the supernatants on a protein A CMS Series S sensor chip (GE Healthcare), and tested for binding to two concentrations (5 nM and 50 nM) of soluble hCD40 extracellular domain. The purified wild-type BMS-986325 was included as a control at the beginning, middle and end of the experiment for a total of n=3 on each of three flow cells, and showed excellent reproducibility over the course of the experiment on each flow cell (Table 22).

TABLE 22

Kinetic and affinity values for hCD40 binding to purified BMS-986325 as determined by SPR. The triplicate data (n = 3) on each flow cell (Fc) were globally fit to obtain ka, kd, and KD values for the binding interaction on each Fc.

| Ligand | Fc | N | ka (1/Ms) | kd (1/s) | KD (nM) |
|---|---|---|---|---|---|
| BMS-986325 | Fc2-1 | n = 3 | 2.0E+05 | 8.7E−04 | 4.4 |
| BMS-986325 | Fc3-1 | n = 3 | 2.0E+05 | 9.1E−04 | 4.5 |
| BMS-986325 | Fc4-1 | n = 3 | 2.1E+05 | 9.1E−04 | 4.4 |

The KD values for CD40 binding to the 96 supernatant samples are summarized in Table 23, and a plot of the kinetic on-rate (ka) and off-rate (kd) values (iso affinity plot) is provided in FIG. 1. It can be seen in FIG. 1 that the majority of variants (72/95=76%) retained equivalent or even improved affinity for CD40 compared to wild type antibody M1. Some of the mutations that consistently improved the binding affinity across multiple HC×LC combinations include the HC mutations to patch 2 (HC8, HC9, HC10, HC15, HC16) as well as the triple LC mutant LC4 (LC-K45Q, R54Q, R61Q). Variants with reduced affinity included all antibodies containing HC11, HC12 and HC13. See FIG. 1. Of these, HC11 and HC12 both contain mutations to basic patch 1, which is the patch closest to the CDR region. HC13 is the proof of concept control sample that was engineered to increase the net positive charge (HC-E46K, E62K).

TABLE 23

KD values for hCD40 binding to BMS-986325 and BMS-986325 variant antibodies captured out of supernatants, as determined by SPR.

| HC# | | | LC# | | | | | |
|---|---|---|---|---|---|---|---|---|
| | | | LC1 | LC2 | LC3 | LC4 | LC5 | LC6 |
| | Construct | | LC-wt | LC-K45Q | LC-K45E | LC-K45Q, R54Q, R61Q | LC-R61Q | LC-K107Q, R108Q |
| | | Patch | | 4 | 4 | 4 | 4 | 5 |
| HC1 | HC-wt | | 4.2 | 4.1 | 4.0 | 3.0 | 4.3 | 4.1 |
| HC2 | HC-K12Q, K13Q | 3 | 3.7 | 3.4 | 3.3 | 2.5 | 3.6 | 3.2 |
| HC3 | HC-K12Q, K13Q, K23Q | 3 | 3.7 | 3.8 | 3.7 | 2.9 | 3.6 | 3.6 |
| HC4 | HC-K12E | 3 | 3.6 | 3.3 | 3.4 | 2.6 | 3.6 | 3.3 |

TABLE 23-continued

KD values for hCD40 binding to BMS-986325 and BMS-986325 variant antibodies captured out of supernatants, as determined by SPR.

| | | | LC# | | | | | |
|---|---|---|---|---|---|---|---|---|
| HC# | | | LC1 | LC2 | LC3 | LC4 | LC5 | LC6 |
| HC5 | HC-K12E, K13Q, K23E | 3 | 3.8 | 3.7 | 4.1 | 3.2 | 3.8 | 3.3 |
| HC6 | HC-K12V, K19S, K23A | 3 | 3.8 | 3.5 | 3.9 | 3.0 | 3.5 | 3.7 |
| HC7 | HC-K23E | 3 | 4.5 | 4.1 | 4.6 | 3.5 | 4.4 | 4.3 |
| HC8 | HC-R38Q, K63Q, R67Q | 2 | 3.4 | 2.9 | 3.1 | 2.5 | 2.9 | 3.2 |
| HC9 | HC-K63Q, R67E | 2 | 3.2 | 3.1 | 3.3 | 2.5 | 3.0 | 3.3 |
| HC16 | HC-K63Q | 2 | 4.1 | 3.9 | 3.8 | 3.3 | 4.1 | 3.9 |
| HC10 | HC-R67E | 2 | 3.0 | 3.0 | 3.0 | 2.1 | 2.9 | 3.0 |
| HC15 | HC-R67Q | 2 | 3.4 | 3.1 | 3.2 | 2.4 | 3.5 | 3.4 |
| HC11 | HC-R57E | 1 | 10.2 | 10.4 | 11.7 | 9.5 | 10.5 | 9.6 |
| HC12 | HC-R57E, K74Q | 1 | 14.0 | 15.7 | 17.2 | 14.7 | 14.8 | 13.4 |
| HC14 | HC-K74T | 1 | 4.0 | 4.0 | 3.9 | 3.1 | 4.0 | 3.6 |
| HC13 | HC-E46K, E62K | 6 | 8.0 | 8.8 | 8.8 | 7.5 | 7.9 | 8.1 |

Example 4: Selection of BMS-986325 Variants for Further Purification and Additional Characterization The titer data, hCD40 binding SPR data, and in silico analysis of the antibody sequences and structural models were collectively considered to identify a subset of antibodies to express at larger scale and purify for additional characterization. For this analysis, properties such as low titer or reduced affinity compared to the wild type antibody were considered undesirable and more likely to be deprioritized. However, rather than bias toward production of only those specific HC×LC combinants with the highest affinity and titer, the aim was to have the purified set of antibodies represent a diverse range of different properties, including at least one mutation to each of the 5 basic patches. For example, all patch 3 mutants were well tolerated with favorable titer and CD40 binding properties, and appeared to be favorably combined with any of the patch 4 or patch 5 LC mutants, but antibodies containing HC4, HC5, and HC6 were prioritized over those with HC2 or HC3 because HC4, HC5 and HC6 variants had larger changes in net charge without any undesirable reduction in titer or loss of binding. Both M13 and M53 were included to ensure that the purified set represented the full range of change in net charge from M13 (+4) to M53 (−8). For further diversity in the purified set, the set included not only variants with Lys and Arg mutated to Glu or Gln, but also variants where Lys or Arg were mutated to human germline residues, including M62 containing HC14 (HC-K74T) and M38 and M54 which contain HC6 (HC-K12V, K19S, K23A). Moreover, several variants with only a single mutation to HC or LC were included to keep the total mutation burden low and reduce the risk of instability or immunogenicity. When all these factors were considered a final set of wild type and 15 mutant antibodies were identified for larger scale expression, purification and characterization. The final set are shown in TABLE 24.

TABLE 24

16 antibodies selected for larger scale expression, purification and characterization.

| M# | Patch | HC# | LC# | HC | LC | # mut | Chrg | Titer (ug/ml) | KD (nM) |
|---|---|---|---|---|---|---|---|---|---|
| M1 (wt) | — | HC1 | LC1 | WT | WT | 0 | 0 | 134 | 4.2 |
| M49 | 4 | HC1 | LC4 | WT | LC-K45Q, R54Q, R61Q | 3 | −3 | 177 | 3.0 |
| M33 | 4 | HC1 | LC3 | WT | LC-K45E | 1 | −2 | 172 | 4.0 |
| M62 | 1/4 | HC14 | LC4 | HC-K74T | LC-K45Q, R54Q, R61Q | 4 | −4 | 176 | 3.1 |
| M80 | 2/4 | HC16 | LC5 | HC-K63Q | LC-R61Q | 2 | −2 | 322 | 4.1 |
| M10 | 2 | HC10 | LC1 | HC-R67E | WT | 1 | −2 | 97 | 3.0 |
| M47 | 2/4 | HC15 | LC3 | HC-R67Q | LC-K45E | 2 | −3 | 198 | 3.2 |
| M63 | 2/4 | HC15 | LC4 | HC-R67Q | LC-K45Q, R54Q, R61Q | 4 | −4 | 174 | 2.4 |
| M4 | 3 | HC4 | LC1 | HC-K12E | WT | 1 | −2 | 86 | 3.6 |
| M36 | 3/4 | HC4 | LC3 | HC-K12E | LC-K45E | 2 | −4 | 251 | 3.4 |
| M37 | 3/4 | HC5 | LC3 | HC-K12E, K13Q, K23E | LC-K45E | 4 | −7 | 146 | 4.1 |
| M53 | 3/4 | HC5 | LC4 | HC-K12E, K13Q, K23E | LC-K45Q, R54Q, R61Q | 6 | −8 | 87 | 3.2 |

TABLE 24-continued 16 antibodies selected for larger scale expression, purification and characterization.

| M# | Patch | HC# | LC# | HC | LC | # mut | Chrg | Titer (ug/ml) | KD (nM) |
|---|---|---|---|---|---|---|---|---|---|
| M38 | 3/4 | HC6 | LC3 | HC-K12V, K19S, K23A | LC-K45E | 4 | −5 | 295 | 3.9 |
| M54 | 3/4 | HC6 | LC4 | HC-K12V, K19S, K23A | LC-K45Q, R54Q, R61Q | 6 | −6 | 108 | 3.0 |
| M81 | 5 | HC1 | LC6 | WT | LC-K107Q, R108Q | 2 | −2 | 223 | 4.1 |
| M13 | 6 | HC13 | LC1 | HC-E46K, E62K | WT | 2 | 4 | 95 | 8.0 |

Example 5: Expression and Purification of BMS-986325 and Variants

The 16 antibodies from Table 24 were expressed in transient Expi293 cells (purchased from ThermoFisher Scientific) under conditions indicated for these cells. The antibodies were purified for additional analytical and biophysical characterization. The additional characterization included production of two batches of M4, identified as M4 and M4-b, to compare material generated from two separate production runs; the two separate production runs were found to have similar analytical and biophysical properties.

Example 6: aSEC Analysis of BMS-986325 and Variants

The purity and oligomeric state of BMS-986325 and the 15 variants were characterized by analytical size exclusion chromatography (aSEC). The data are show in Table 25.

TABLE 25 aSEC data for purified BMS-986325 and variants

| Sample Name | RT of main | % HMW | % Main | % LMW |
|---|---|---|---|---|
| M1 (wt) | 8.3 | 1.1 | 98.9 | 0.0 |
| M49 | 8.3 | 0.1 | 99.9 | 0.0 |
| M33 | 8.3 | 1.9 | 98.1 | 0.0 |
| M62 | 8.3 | 0.6 | 99.4 | 0.0 |
| M80 | 8.3 | 0.3 | 99.7 | 0.0 |
| M10 | 8.3 | 0.2 | 99.8 | 0.0 |
| M47 | 8.3 | 3.5 | 96.5 | 0.0 |
| M63 | 8.3 | 0.4 | 99.6 | 0.0 |
| M4 | 8.3 | 0.4 | 99.6 | 0.0 |
| M4-b | 8.3 | 0.4 | 99.6 | 0.0 |
| M36 | 8.3 | 5.5 | 94.5 | 0.0 |
| M37 | 8.3 | 1.3 | 98.7 | 0.0 |
| M53 | 8.3 | 0.5 | 99.6 | 0.0 |
| M38 | 8.3 | 6.6 | 93.4 | 0.0 |
| M54 | 8.3 | 0.1 | 99.9 | 0.0 |
| M13 | 8.3 | 0.0 | 100.0 | 0.0 |
| M81 | 8.3 | 1.3 | 98.7 | 0.0 |

All samples were found to be of suitable quality for additional studies, with a percent monomer of greater than 93%, and less than 7% high molecular weight (HMW) species and no detectable low molecular weight (LMW) species.

Example 7: icIEF Analysis of BMS-986325 and Variants

The impact of the various mutations on the charge properties of BMS-986325 were evaluated using imaged capillary isoelectric focusing (icIEF). These data are shown in Table 26.

TABLE 26 icIEF data for purified BMS-986325 and variants

| Sample | pI main | % Acidic | % Main | % Basic |
|---|---|---|---|---|
| M1 (wt) | 9.21 | 22.2 | 76.1 | 1.7 |
| M49 | 8.83 | 20.3 | 77.6 | 2.1 |
| M33 | 9.02 | 21.0 | 79.0 | 0.0 |
| M62 | 8.67 | 20.7 | 79.3 | 0.0 |
| M80 | 8.94 | 20.0 | 78.2 | 1.8 |
| M10 | 8.92 | 16.6 | 81.0 | 2.4 |
| M47 | 8.88 | 20.0 | 80.0 | 0.0 |
| M63 | 8.66 | 17.0 | 82.0 | 1.0 |
| M4 | 8.96 | 26.1 | 71.7 | 2.2 |
| M4-b | 8.97 | 22.0 | 76.5 | 1.5 |
| M36 | 8.74 | 22.4 | 77.6 | 0.0 |
| M37 | 8.02 | 13.3 | 86.7 | 0.0 |
| M53 | 7.53 | 12.1 | 87.9 | 0.0 |
| M38 | 8.55 | 21.1 | 78.9 | 0.0 |
| M54 | 8.24 | 12.0 | 88.0 | 0.0 |
| M13 | 9.42 | 5.8 | 94.2 | 0.0 |
| M81 | 8.20 | 12.0 | 87.0 | 1.0 |

Wild-type BMS-986325 had a main peak isoelectric point (pI) of 9.21, with 76.1% main peak, 22.2% acidic variants and 1.7% basic variants. See M1 in Table 26. The icIEF profiles for all the other antibodies also consistent of predominantly main peak (71.7-94.2%) with some acidic variants (5.8-26.1%) and either a small amount or no basic variants (0-2.4%).

As anticipated, M13, the only mutant designed to increase positive charge, was found to have a higher main peak pI (9.42) than wild type BMS-986325, whereas all of the other mutants which were designed to replace positively charged residues with neutral or acidic residues were found to have lower pI than wild type BMS-986325.

Example 8: aHIC Analysis of BMS-986325 and Variants

The hydrophobicity of wild type and mutant BMS-986325 molecules were evaluated by analytical hydrophobic interaction chromatography (aHIC). The data are provided in Table 27.

TABLE 27

| aHIC data for purified BMS-986325 and variants | | | | |
|---|---|---|---|---|
| Sample | RT of main | Pre-peak | % Main | Post-peak |
| M1 (wt) | 10.1 | 0.0 | 100.0 | 0.0 |
| M49 | 10.5 | 0.0 | 76.1 | 23.9 |
| M33 | 10.1 | 0.0 | 85.1 | 14.9 |
| M62 | 10.8 | 0.0 | 79.7 | 20.3 |
| M80 | 10.2 | 0.0 | 100.0 | 0.0 |
| M10 | 10.1 | 0.0 | 100.0 | 0.0 |
| M47 | 10.1 | 0.0 | 88.4 | 11.6 |
| M63 | 10.5 | 0.0 | 79.2 | 20.8 |
| M4 | 10.2 | 0.0 | 100.0 | 0.0 |
| M4-b | 10.1 | 0.0 | 100.0 | 0.0 |
| M36 | 10.2 | 0.0 | 81.5 | 18.5 |
| M37 | 10.2 | 0.0 | 70.1 | 29.9 |
| M53 | 10.7 | 0.0 | 53.4 | 46.6 |
| M38 | 10.3 | 0.0 | 59.8 | 40.2 |
| M54 | 10.8 | 0.0 | 55.2 | 44.8 |
| M13 | 10.1 | 0.0 | 100.0 | 0.0 |
| M81 | 10.2 | 0.0 | 100.0 | 0.0 |

In this analysis, wild type BMS-986325 eluted as a single symmetrical peak with main peak retention time (RT) of 10.1 min See M1 in Table 27. Several of the mutations, which were designed to disrupt positively charged patches, did so while maintaining low hydrophobicity (RT=10.1-10.3 min), including M4, M10, M13, M33, M36, M47, M80, M81. This subset of antibodies includes variants having one or two charged residues mutated to uncharged residues, such as M47, M80, and M81. In contrast, all variants utilizing LC4 (LC-K45Q, R54Q, R61Q) which was the most highly mutated light chain tested and replaced three charged residues with three uncharged residues, had increased hydrophobicity compared to wild type (RT=10.5-10.8 min).

The heterogeneity of the BMS-986325 variants also generally increased with more mutation. For example, all antibodies utilizing a HC or a LC containing three mutations (HC5, HC6, LC4) eluted as <80% main peak with a corresponding increased levels of post-peak (later eluting) more hydrophobic species. The two variants which had three mutations to each of the HC and LC for a total of six mutations (M53 and M54) had particularly high heterogeneity, with main peak of 53.4-55.2% and post peak of 46.6-44.8%.

Example 9: UNcle Thermal Stability Analysis of BMS-986325 and Variants

The structural and colloidal stability of the BMS-986325 variants were investigated by fluorescence spectroscopy and static light scattering (SLS) respectively, using an UNcle instrument (Unchained Labs, Pleasanton, CA). The thermal denaturation of each antibody was accompanied by a distinct change in fluorescence, which could be monitored using the barycentric mean (BCM) method and fit to determine a melting temperature 1 ($T_{m1}$) value. This was followed at higher temperatures by a large increase in SLS that is indicative of aggregation of the denatured protein molecules, from which the aggregation onset temperature ($T_{agg}$) can be determined by monitoring at either 266 nm ($T_{agg}$266) or 473 nm ($T_{agg}$473).

The data are shown in Table 28.

TABLE 28

| $T_m$ and $T_{agg}$ thermal stability data for purified BMS-986325 and variants | | | |
|---|---|---|---|
| Sample | $T_{m1}$ (° C.) | $T_{agg}$ 266 (° C.) | $T_{agg}$ 473 (° C.) |
| M1 (wt)* | 65.8 ± 0.3 | 79.7 ± 0.1 | 79.8 ± 0.4 |
| M49 | 66.5 | 78.1 | 78.4 |
| M33 | 66.5 | 79.9 | 80.2 |
| M62 | 66.1 | 78.2 | 78.2 |
| M80 | 66.0 | 76.7 | 76.6 |
| M10 | 65.5 | 72.6 | 72.2 |
| M47 | 66.0 | 74.7 | 74.7 |
| M63 | 65.5 | 72.6 | 72.7 |
| M4 | 65.7 | 76.1 | 76.1 |
| M4-b | 65.5 | 76.2 | 76.3 |
| M36 | 66.0 | 75.7 | 75.6 |
| M37 | 65.1 | 73.1 | 73.7 |
| M53 | 65.5 | 70.6 | 70.6 |
| M38 | 66.5 | 76.1 | 75.8 |
| M54 | 66.7 | 73.7 | 73.8 |
| M13 | 67.1 | 75.0 | 74.9 |
| M81 | 67.6 | 75.9 | 75.8 |

*Values for M1 (wt) are average ± standard deviation of three independent measurements.

The $T_m$ and $T_{agg}$ values (average±standard deviation for triplicate measurement) for wild type BMS-986325 were $T_{m1}$=65.8±0.3° C., $T_{agg}$266=79.7±0.1° C., and $T_{agg}$473=79.8±0.4° C. $T_{m1}$ values for all of the antibody variants were between 65.1 and 67.6° C., with all variants except for M37 having comparable (within standard deviation) or slightly higher $T_{m1}$ compared to wild type BMS-986325. In contrast, the $T_{agg}$ varied over a larger range for both $T_{agg}$266 (70.6-79.9° C.) and $T_{agg}$473 (70.6-80.3° C.), with all variants except M33 having lower $T_{agg}$ values than wild type.

A direct correlation between the number of mutations and the $T_{agg}$ values for this set of antibodies was not observed, suggesting that the location of the mutation and identity of the amino acid change are scientifically important for maintaining the thermal stability of the antibody. For example, the $T_{agg}$ for M62 (4 total mutations) was higher than that for several mutants that had only 1, 2 or 3 mutations (M4, M10, M13, M36, M47, M49, M80, M81), whereas a single mutation in M10 resulted in a significant destabilization, with $T_{agg}$266=72.6° C. and $T_{agg}$473=72.2° C.

Example 10: ECM ELISA Analysis of BMS-986325 and Variants

To evaluate the potential for nonspecific binding of the positively charged BMS-986325 surface patches to acidic surfaces, and the impact of mutation on those interactions, an extracellular matrix (ECM) binding ELISA assay was utilized. The data are shown in Table 29.

TABLE 29

| ECM score for purified BMS-986325 and variants. | | | |
|---|---|---|---|
| Sample | ECM @ 1 μM | ECM @ 0.33 μM | ECM @ 0.11 μM |
| M1 (wt) | 23 | 14 | 8 |
| M49 | 2 | 2 | 1 |
| M33 | 3 | 2 | 2 |
| M62 | 1 | 1 | 1 |
| M80 | 9 | 5 | 3 |

TABLE 29-continued

ECM score for purified BMS-986325 and variants.

| Sample | ECM @ 1 μM | ECM @ 0.33 μM | ECM @ 0.11 μM |
|---|---|---|---|
| M10 | 22 | 12 | 6 |
| M47 | 2 | 2 | 3 |
| M63 | 1 | 2 | 1 |
| M4 | 8 | 5 | 2 |
| M36 | 2 | 2 | 2 |
| M37 | 2 | 2 | 1 |
| M53 | 2 | 1 | 1 |
| M38 | 2 | 4 | 1 |
| M54 | 2 | 2 | 1 |
| M13 | 72 | 67 | 58 |
| M81 | 14 | 8 | 3 |

Wild type BMS-986325 (M1) generated a strong ECM binding response with ECM score of 23.5 at the 1 μM concentration. As would be predicted, the proof of concept control molecule, M13 into which an additional positively charge patch was introduced by the E46K-E62K double mutation, was found to demonstrate a much stronger ECM binding response than wild type BMS-986325 with ECM score of 72.0 at the 1 μM concentration. The single HC-R67E mutation (M10) had the smallest impact on ECM score compared to wild type antibody, with ECM score of 21.7 at 1 μM concentration. M4, M80 and M81 demonstrated some reduction in ECM binding but maintained measureable ECM binding (ECM score=8.1.-14.0 at 1 μM). All of the other variants (M33, M36, M37, M38, M47, M49, M53, M54, M62, M63) demonstrated significantly reduced ECM binding responses with ECM scores of 1.4-3.1 at 1 μM.

Example 11: CD40 Binding SPR Analysis of BMS-986325 and Variants

The CD40 target binding kinetics and affinity of BMS-986325 and the 15 purified variants were evaluated using a SPR method similar to SPR method previously used to screen the 96 small scale expression supernatants, except that rather than just two analyte concentrations in the supernatant screening experiment, a full set of 6 CD40 analyte concentrations were tested for the purified antibodies. Additionally, to more accurately define the dissociation rate (kd), a longer dissociation time of 360 seconds (s) was used as opposed to the shorter 180 s dissociation that had been used in the supernatant screening experiment.

The data are shown in Table 30.

TABLE 30

Kinetic and affinity values for hCD40 binding to purified BMS-986325 and BMS-986325 variants as determined by SPR.

| Ligand | ka (1/Ms) | kd (1/s) | KD (nM) |
|---|---|---|---|
| M1 (wt)* | 2.2 ± 0.0E+05 | 6.6 ± 0.3E−04 | 3.1 ± 0.1 |
| M49 | 3.2E+05 | 7.0E−04 | 2.2 |
| M33 | 2.6E+05 | 7.3E−04 | 2.9 |
| M62 | 3.0E+05 | 6.6E−04 | 2.2 |
| M80 | 2.4E+05 | 7.0E−04 | 2.9 |
| M10 | 2.9E+05 | 6.7E−04 | 2.3 |
| M47 | 3.3E+05 | 7.4E−04 | 2.2 |
| M63 | 4.0E+05 | 7.3E−04 | 1.8 |
| M4 | 2.5E+05 | 6.9E−04 | 2.8 |
| M36 | 3.0E+05 | 7.8E−04 | 2.6 |
| M37 | 2.5E+05 | 8.4E−04 | 3.3 |
| M53 | 3.2E+05 | 8.0E−04 | 2.5 |
| M38 | 2.8E+05 | 7.7E−04 | 2.8 |
| M54 | 3.3E+05 | 7.5E−04 | 2.3 |
| M13 | 8.1E+04 | 6.8E−04 | 8.4 |
| M81 | 2.4E+05 | 7.0E−04 | 3.0 |

*Values for M1 (wt) are average ± standard deviation of three independent measurements.

The observed impact of the mutations on CD40 binding to the purified antibodies was similar to that observed with the supernatants, with M13 having significantly lower affinity than wild type BMS-986325, and the other variants have similar or modestly higher affinity.

Example 12: Functional Potency Analysis of BMS-986325 Variants

The impact of the mutations on the functional potency of BMS-986325 to inhibit CD40L stimulated activity on primary human tonsillar B cells was tested. The data are provided in Table 31.

TABLE 31

Activity of BMS-986325 on human tonsillar B cells. Inhibition of tonsillar human B cell proliferation stimulated by IZ-hCD40L trimer or human CD40L expressing CHO cells. Assays performed in triplicate. B cells from n-donors were tested.

| | Stimulation | | | |
|---|---|---|---|---|
| | IZ-hCD40L trimer | | hCD40L expressing CHO cells | |
| | IC50 (ng/ml ± SD) | n = donors | IC50 (ng/ml ± SD) | n = donors |
| BMS-986325 P1-073346-1 | 1.4 ± 0.2 | 2 | 47.0 ± 8.6 | 2 |
| BMS-986325-WT P1-071223-1 lot 1 | 1.2 ± 0.1 | 2 | 42.0 ± 14.2 | 4 |
| BMS-986325-WT P1-071223-3 lot 3 | 5.6 | 1 | 31.4 ± 9.9 | 2 |
| M49 | 0.7 ± 0.1 | 2 | 67.2 ± 1.9 | 2 |
| M33 | 0.9 ± 0.1 | 2 | 57.5 ± 46.6 | 2 |
| M62 | 6.2 ± 1.3 | 2 | 356.2 ± 265.9 | 2 |
| M80 | 16.4 ± 2.9 | 2 | 368.8 ± 271.5 | 2 |
| M10 | 27.7 ± 7.6 | 2 | 352.7 ± 217.2 | 2 |
| M47 | 0.4 | 1 | 54.7 ± 39.6 | 2 |
| M63 | 5.7 | 1 | 207.7 ± 123.0 | 2 |
| M4 lot 2 | 0.8 ± 0 | 2 | 39.6 ± 17.4 | 2 |
| M36 | 2.6 ± 0.6 | 2 | 47.7 ± 24.7 | 2 |
| M37 | 0.9 ± 0.1 | 2 | 128.7 ± 105.9 | 2 |
| M53 | 3.4 ± 0.8 | 2 | 367.3 ± 361.2 | 2 |
| M38 | 7.2 ± 0.2 | 2 | 181.2 ± 71.2 | 2 |
| M54 | 3.3 ± 0.4 | 2 | 201.2 ± 152.5 | 2 |
| M13 | 3.3 ± 2.0 | 2 | 20.8 ± 5.7 | 2 |
| M81 | 0.7 ± 0.1 | 2 | 25.7 ± 14.3 | 2 |
| M4 lot 1 | 2.9 ± 0.5 | 2 | 23.7 ± 6.5 | 2 |

All mutants exhibited potent inhibition of soluble CD40L trimer (IZ-hCD40L) stimulated B cell proliferation, with most mutants exhibiting similar potency to BMS-986325, with IC50 values within 2-3 fold (typically the range of donor variability in these assays as illustrated by the two lots of mutant M4). Exceptions include several mutant, M62, M809, M10, and M38, which showed modestly lower potency.

Similarly, all mutants inhibited the B cell proliferation stimulated by cell surface CD40L (CHO-CD40L), which is typically more difficult to inhibit. In these experiments, several mutants were modestly less potent but with high variability between the two donors tested (M62, M80, M10, M63, M37, M38, M54); the remaining mutants exhibited potencies within 3 fold that observed for BMS-986325. Collectively this data suggests that most mutations had minimal impact on CD40 potency with a select number of mutations exhibiting only a modest a shift in potency.

Figure 5:
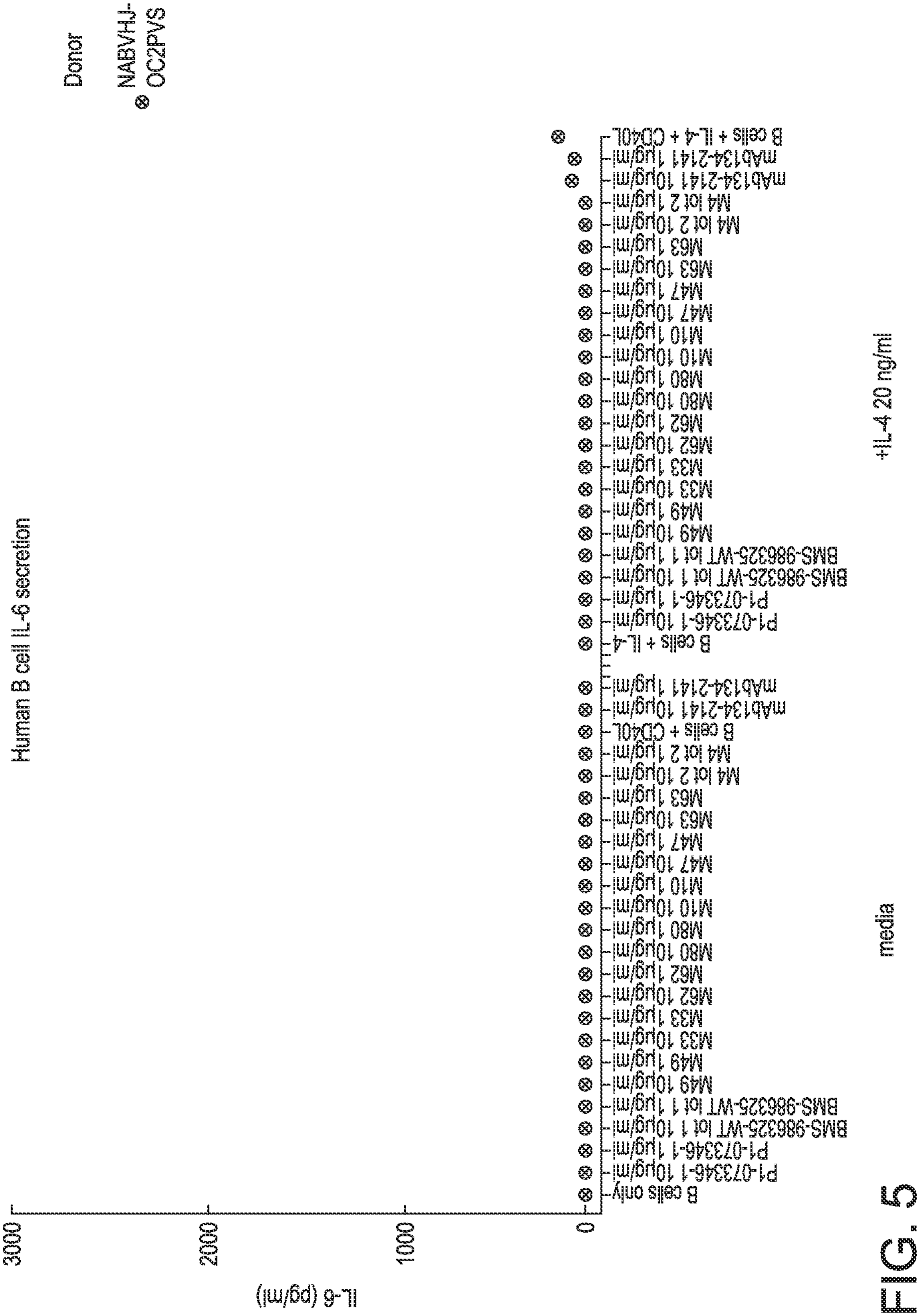
FIG. 5 depicts data for human B cell IL-6 secretion for BMS-986325 and its variants in media or +IL-4 (+IL-4 20 ng/ml) using human B cells from donor NABVHJ-OC2PVS.
Figure 6:
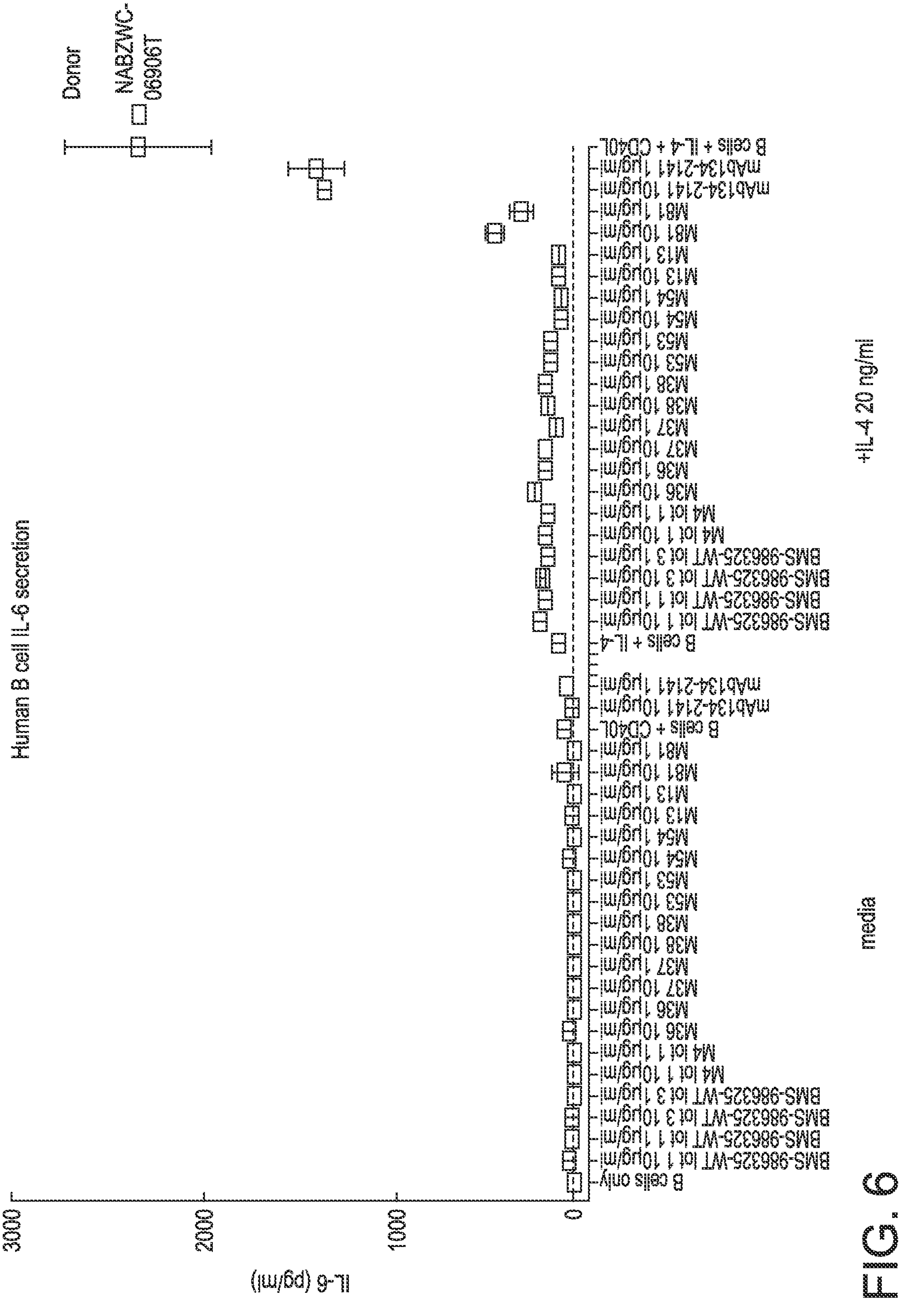
FIG. 6 depicts data for human B cell IL-6 secretion for BMS-986325 and its variants in media or +IL-4 (+IL-4 20 ng/ml) using human B cells from donor NABZWC-06906T.
Figure 7:
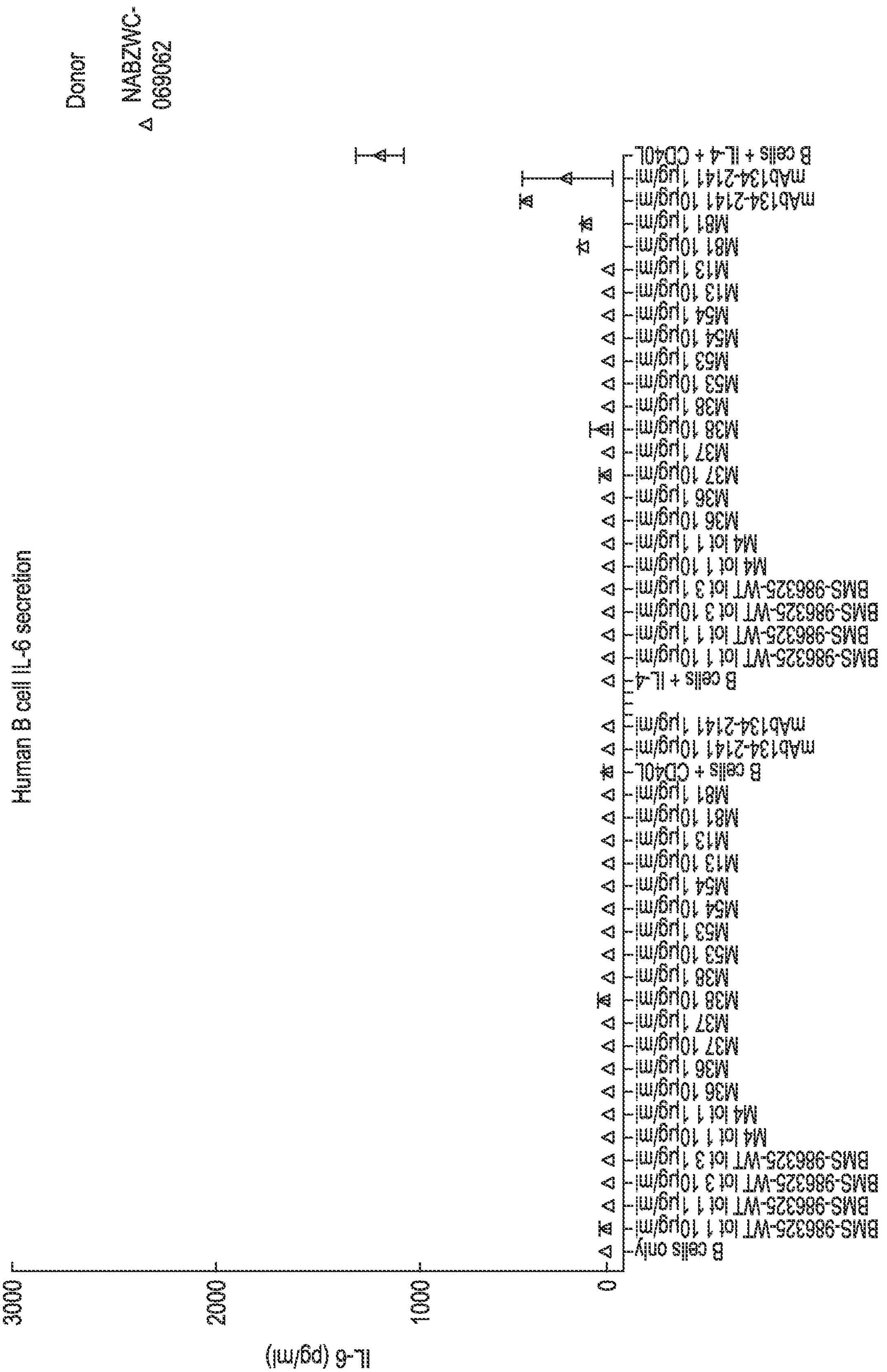
FIG. 7 depicts data for human B cell IL-6 secretion for BMS-986325 and its variants in media or +IL-4 (+IL-4 20 ng/ml) using human B cells from donor NABZWC-069062.

There are prior art CD40 antibodies described as having the potential to have agonist activity. In contrast, BMS-986325 is a pure antagonist showing no agonism on B cells either alone or in combination with IL-4, which sensitizes B cells to proliferation and activation signals. The potential of the mutations to influence potential agonism was also tested by monitoring for B cell stimulation by assaying proliferation and cytokine production. FIGS. 2-7 depict data of the assessment of potential for agonistic activity of BMS-986325 with IL-4-stimulated human B cells measuring proliferation (FIGS. 2-4) and cytokine secretions (FIGS. 5-7). None of the mutants, except for one (M81), lead to agonism when tested in B cells, with each molecule tested in a total of two donors. The M81 mutation showed a weak increase in proliferation only in the presence of IL-4 in one of the two donors tested, and IL-6 production only in the presence of IL-4 with both donors tested. These data suggest that this mutation may change the conformation of the resultant antibody to enable some degree of agonism.

Example 13: Intrinsic Pharmacokinetics of BMS-986325 and Variants

Figure 8:
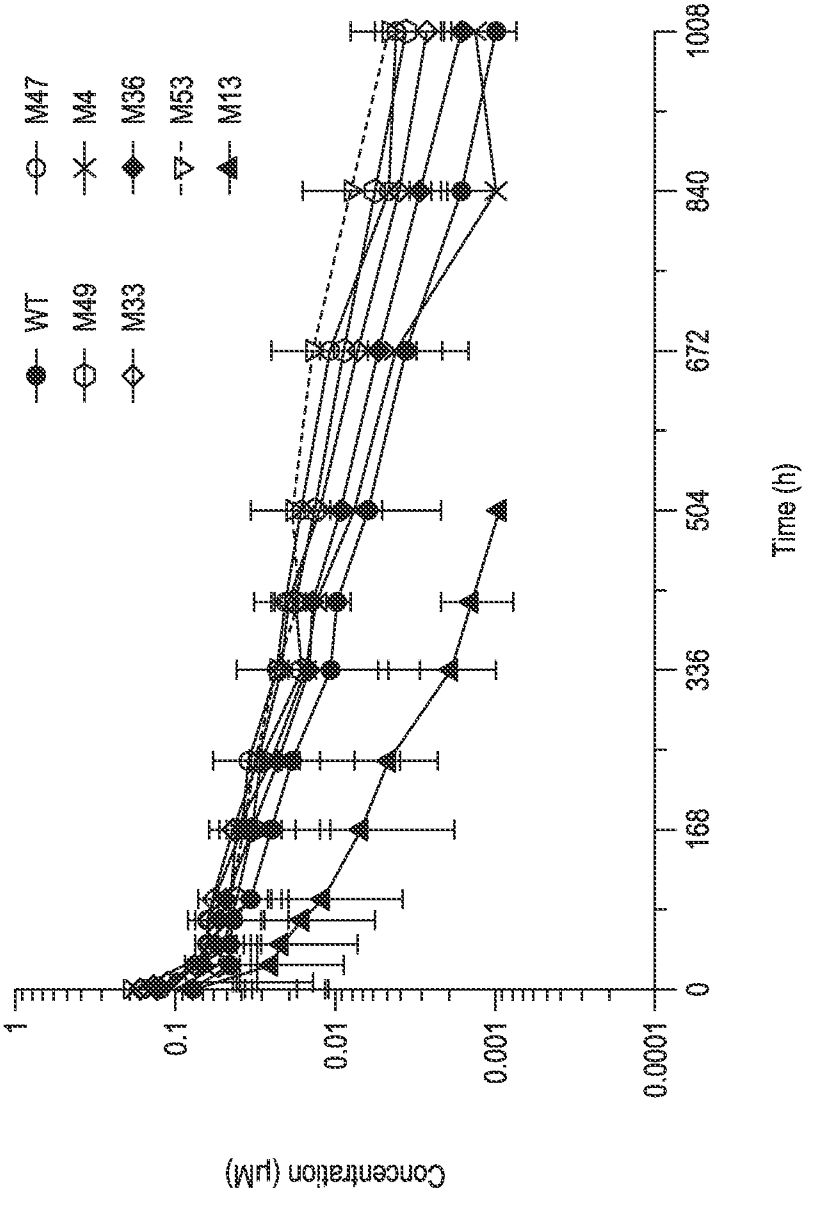
FIG. 8 depicts data for single dose pharmacokinetics (PK) of BMS-986325 and its variants at 1 mg/kg intravenous dosing in C57/BL6 mice.

The "intrinsic" PK of BMS-986325 and its variants is presented in FIG. 8 and the calculated "intrinsic" PK parameters are provided in Table 32.

variability, M13 has worse PK (lower AUC and higher clearance) than wild type BMS-986325, whereas the PK of all other variants are similar or improved with respect to wild type BMS-986325.

Materials and Methods for Examples 1 to 13

Cloning of BMS-986325 variants: The coding sequences for CD40 mAb heavy chains BMS-986325-IgG1a-P238K-K12Q-K13Q and BMS-986325-IgG1a-P238K-R63Q were codon optimized for Chinese hamster ovary cell (CHO) expression and the synthetic DNA fragments were cloned into a modified pTT5 mammalian expression vector. The rest of the CD40 mAb heavy chains were generated by mutagenesis using one of the above two constructs as template.

The coding sequence for CD40 mAb light chain BMS-986325-Vk-K45Q-hLC was also codon optimized for CHO expression, and the synthetic DNA fragment was cloned into the same pTT5 vector. The rest of the CD40 mAb light chains were generated by mutagenesis using the above light chain construct as template.

Expression of BMS-986325 and BMS-986325 variants: For initial screening experiments, antibodies were expressed at 3 ml scale using Thermo Fisher Scientific Expi293™ expression system (ThermoFisher Scientific, Waltham, MA). The DNA/Expifectamine™ ratio was 1:2.7; DNA amount was 0.5 mg/L. Cell seeding density was $2.7\times10^{6}$ (after transfection the cell density was $2.5\times10^{6}$). Cells were fed 24 hours post-transfection with 0.5M valproic acid to final 2 mM concentration and CHO CD EfficientFeed™ B to final volume at 5% from Gibco® (ThermoFisher Scientific, Waltham, MA; cat #A10240-02). Culture growth condition was 37° C., 8% CO2 with humidity. Supernatants were harvested on day 5 by centrifugation. Larger scale expression was done at 0.5 L scale.

TABLE 32

Single dose PK parameters of BMS-986325 and its variants at 1 mg/kg IV in C57/BL6 mice calculated by non-compartmental analysis (NCA).

| PK Parameters | WT | M49 | M33 | M47 | M4 | M36 | M53 | M13 |
|---|---|---|---|---|---|---|---|---|
| AUC 0-inf (μM · h) | 13 ± 4 | 20 ± 8 | 23 ± 3 | 25 ± 3 | 17 ± 1 | 17 ± 4 | 21 ± 18 | 4 ± 3 |
| T-Half (h) | 168 ± 3 | 279 ± 57 | 206 ± 21 | 231 ± 7 | 155 ± 10 | 194 ± 14 | 201 ± 81 | 97 ± 21 |
| MRT (h) | 241 ± 12 | 377 ± 45 | 282 ± 14 | 335 ± 13 | 224 ± 17 | 264 ± 13 | 288 ± 115 | 131 ± 41 |
| CL (mL/h/kg) | 0.56 ± 0.17 | 0.37 ± 0.13 | 0.3 ± 0.05 | 0.28 ± 0.03 | 0.39 ± 0.02 | 0.42 ± 0.13 | 0.5 ± 0.32 | 2.97 ± 3.16 |
| Vss (L/kg) | 0.14 ± 0.05 | 0.14 ± 0.05 | 0.09 ± 0.01 | 0.09 ± 0.01 | 0.09 ± 0.01 | 0.11 ± 0.03 | 0.12 ± 0.05 | 0.47 ± 0.6 |

After intravenous (IV) administration of BMS-986325 (single 1-mg/kg doses) to mice, BMS-986325 exhibited a mean low total serum clearance "CL" of 0.56 mL/h/kg, limited volume of distribution at steady state "Vss" of 0.14 L/kg, and an apparent elimination half-life "T-Half" of 168 hours (~7 days). Within variability, all variants (M49, M33, M47, M4, M36 and M53) except M13, have comparable or better PK than WT (area under the concentration-time curve "AUC" and CL within 2 fold). In contrast, at this dose, and within variability, the PK of M13 variant is worse than that of WT (lower AUC by 3.2 fold and higher CL by 5.3 fold). Each of M39, M33, M47, M4, M36 and M53 had improved values for at least one of these PK parameters, and for most of variants, had improved values for at least two of these PK parameters.

Thus, at this dose, within variability, the overall PK of all variants except for M13 is similar or slightly better than that of wild type BMS-986325. That is, at this dose, within Purification of BMS-986325 and BMS-986325 variants: Clarified antibody-rich supernatants were bound to a 5 mL MabSelect SuRe™ (Cytiva, Marlborough, MA) column, washed with five column volumes of 1× phosphate-buffered saline (PBS) pH 7.2 until baseline was reached. Antibody was eluted with 50 mM acetic acid pH 3.0 and run over a Superdex 26/10 desalting column to exchange the buffer to PBS pH7.2. All samples had greater than 5% impurities and were run over a Superdex® 200 26/600 prep grade (pg) preparative SEC (pSEC) column (GE Healthcare, Chicago, IL) to remove these impurities. Samples were then concentrated to at least 1 mg/mL, and filtered through a 0.2 μm filter prior to freezing.

Octet BLI Titer analysis: Antibody titer was determined using Octet RED384 and Protein A sensor tips by ForteBio. An 8-point standard curve was made using a human IgG1f isotype standard antibody in PBS-T buffer, with a concentration range of 150-1.17 μg/mL. The standard curve was done in triplicate. Sample supernatants were diluted 1:2 in PBS-T buffer (10 mM $NaPO_4$, 130 mM NaCl, 0.05% tween 30 (PBS-T) pH 7.2). Standard curve and samples were placed in a black flat bottom 96-well plate (Corning), final volume in wells was 100 μL. Protein A sensor tips were hydrated in PBS-T buffer for −10 mins before run began. Association was 180 s at 30 μL/min and Protein A sensor tips were regenerated using 10 mM glycine pH 1.5. Data was obtained using the Octet Software Data Acquisition and Data Analysis.

CD40 binding SPR of antibody supernatants: Surface plasmon resonance (SPR) studies were conducted on a BIAcore™ T200 instrument (GE Healthcare, Chicago IL). A Series S Protein A sensor chip (GE Healthcare, Chicago IL) was equilibrated with SPR running buffer of 10 mM $NaPO_4$, 130 mM NaCl, 0.05% tween 20, (PBS-T) pH 7.2 at 25° C. The 96 antibody supernatants were normalized to a concentration of 3 μg/ml by diluting with PBS-T using a PerkinElmer JANUS® G3 system (PerkinElmer, Akron, OH). After priming the system, the 3 μg/ml antibody samples were captured on the protein A surface for 30 s at 10 μl/min Binding of 50 nM and 500 nM human CD40 extracellular domain (produced in house) was evaluated using association time of 180 s at 30 μl/min, followed by a dissociation time of 180 s at 30 μl/min Regeneration between cycles was accomplished using two 15 s injections of 10 mM glycine pH 1.5. The wild type BMS-986325 was tested three separate times on each of the three independent flow cells for a total of 9 measurements. Data were analyzed using BIAcore™ T200 evaluation software by fitting to a 1:1 Langmuir model.

CD40 binding SPR: SPR studies of the purified antibodies were conducted on BIAcore™ T200 instrument (GE Healthcare, Chicago IL). A Series S Protein A sensor chip (GE Healthcare, Chicago IL) was equilibrated with SPR running buffer of 10 mM $NaPO_4$, 130 mM NaCl, 0.05% tween 20, (PBS-T) pH 7.2 at 25° C. The purified antibody samples were diluted to 3 μg/ml in PBS-T and captured on the protein A surface for 30 s at 10 μl/min Binding of 3.91, 7.81, 15.6, 31.3, 62.5, and 125 nM human CD40 extracellular domain (produced in house) was evaluated using association time of 180 s at 30 μl/min, followed by a dissociation time of 360 s at 30 μl/min Regeneration between cycles was accomplished using two 15 s injections of 10 mM glycine pH 1.5. The wild type BMS-986325 was tested once on each of the three independent flow cells. Data were analyzed using BIAcore™ T200 evaluation software by fitting to a 1:1 Langmuir model.

aSEC analysis: Isocratic separations were performed on a Shodex™ K403-4F column (Showa Denko America, Inc., New York, NY) connected to an Agilent™ 1260 series HPLC system in buffer containing 100 mM Sodium Phosphate, 150 mM Sodium Chloride pH 7.3 (0.1 μm filtered) running at 0.3 mL/min. Injections of 20 μg of antibody were performed using an Agilent™ autosampler, and data were obtained using an Agilent™ diode array detector reading at 280 nm, 260 nm, 214 nm, 254 nm, with reference subtraction at 360 nm. Data were analyzed using ChemStation™ (Agilent™) software.

icIEF analysis: Imaged capillary isoelectric focusing (icIEF) experiments were performed on a Maurice instrument (ProteinSimple, San Jose, CA). Instrument settings include pre-focus for 1 mM at 1500V and focus for 10 mM at 3000V. Antibody samples were first diluted to a final concentration of 2 mg/mL in double distilled water ($ddH_2O$). In the final plate, 20 μL of sample were mixed with 180 μL of Master Mix (MM) for final concentrations of 0.35% methyl cellulose (MC), 2.0 M Urea, 1% v/v % Pharmalyte® 5-8, and 3% v/v % Pharmalyte® 8-10.5. MM contains per sample: 1.0% MC solution (70 μL), Pharmalyte® 5-8 (2 μL), Pharmalyte® 8-10.5 (6 μL), 8 M Urea (50 μL), Arginine (100×), dd Water (50 μL), pI marker 5.85 (1 μL), and pI market 10.10 (1 μL) (Pharmalyte®, Cytiva, Marlborough, MA). Data was obtained and analyzed using Compass for iCE by ProteinSimple.

aHIC analysis: The high-performance analytical hydrophobic interaction chromatography (aHIC) method was performed on a Agilent 1260 series HPLC. The data were collected at 280 nm, with reference subtraction at 360 nm. A Tosoh TSKgel Butyl NPR column with the dimensions 4.6 mm*3.5 cm, 2.5 μm particle size and flow rate of 1 mL/min was utilized for separation. A 20-minute linear gradient ranging from 1.8 M to 0.0 M Ammonium Sulfate in 0.1 M Sodium Phosphate buffer (pH 7.0). The column and auto sampler temperatures were set at 25° C. and 4° C., respectively. The column loading was 10 μg. Data were analyzed using Chemstation (Agilent) software.

Thermal stability analysis: Determination of the temperature of melting on-set and the temperature of aggregation on-set were performed utilizing an UNcle instrument (Unchained Labs). In brief, 9 μL of sample at 1 mg/mL were loaded into sample Uni cuvette, sealed, and placed into the instrument. A temperature gradient from 25° C. to 90° C. at 0.5° C./min was applied to the sample. Full-spectrum UV absorbance (250 nm-725 nm) as well as static light scattering emission at 266 nm and 473 nm specifically was obtained at each time-point. Fitting of resulting Tm/$T_{agg}$ was performed by UNCLE analysis software (Unchained Labs).

ECM binding ELISA analysis: Extracellular matrix (ECM) binding ELISA assays were performed using 96 well Corning® Thin-Layer Matrigel® Matrix pre-coated ECM plates (Corning Incorporations Life Sciences, Tewksbury, MA). Plates were incubated for one hour at room temperature with 300 μl of blocking buffer (10% fetal calf serum (FCS) in TBS). After incubation 100 μl of fresh blocking buffer was added with 1 μM, 0.33 μM and 0.11 μM of antibody samples. Six wells had no sample addition for background and ECM score calculations. After one hour of sample incubation, samples were removed and plates washed with PBS-T wash buffer 3×. 10 ng/ml of goat anti-human IgG—HRP (horseradish peroxidase) conjugated detection antibody was added at 100 μl to all wells. After another one hour incubation at room temperature, the wells were washed 3× with PBS-T wash buffer. After washing, 100 μl of TMB (3,3',5,5'-metramethylbenzidine) substrate was added to each well and allowed to react for 15 minutes, followed by addition of 100 μl of 1 M phosphoric acid stop solution. Absorbance was then read on a microplate reader at 450 nm referenced at 620 nm.

In vitro activity assessment of BMS-986325 and its variants in human B cell assays: Briefly, human tonsillar B cells were obtained from pediatric patients during routine tonsillectomy. After gently mashing the tissue, mononuclear cells were separated by density gradient separation using Lympholyte®-H separation media (Cedarlane Labs, Burlington, ON, Canada), washed, and rosetted with sheep red blood cells (SRBC, Colorado Serum Company; Denver, CO), followed by density gradient separation to remove T cells. Cells were washed and re-suspended in complete media consisting of RPMI-1640 with 2 mM L-Glutamine (Cat. #11875) supplemented with 10% fetal bovine serum (cat. #26140), 50 μg/ml gentamicin (cat. #15750) and 1% antibiotic-antimycotic (cat. #15240) (all purchased from Gibco™; Carlsbad, CA).

Inhibition of soluble or membrane-bound CD40L stimulated Human B cell proliferation: Isoleucine zipper human CD40L trimer (IZ-hCD40L) or Chinese hamster ovary cells stably transfected with human CD40L (CHO-hCD40L) were used as a stimulus for CD40 activation and a positive control. CD40 agonist mAb2141-hHCD-IgG2-puCOEgate-SP5 was used as positive control for CD40 pathway activation by an agonist antibody. BMS-986325 antibodies were titrated in complete media and pipetted in triplicate to 96 well round bottom plates. $1\times10^5$ tonsillar B cells were added, and stimulated with either soluble IZ-hCD40L (3 ug/ml), or with CHO-hCD40L irradiated with 10,000 rads, and plated at $2\times10^3$ cells/well, in a final volume of 200 µl per well. Plates were incubated at 37° C. in a humidified incubator with 5% $CO_2$ for 72 hours. During the last 7 hours of incubation, cells were labeled with 0.5 µCi of [methyl-$^3$H]-thymidine per well, harvested on glass fiber filter plates, and counted by liquid scintillation on a Packard Topcount® NXT™ counter (PerkinElmer Life and Analytical Sciences, Shelton, CT). B cell proliferation was quantitated based on thymidine incorporation. For analysis, a 4-parameter curve was generated from triplicate values and fit using GraphPad Prism™ software (ver. 7, GraphPad Software, San Diego, CA).

Evaluation of potential agonism on human B cells with BMS-986325 and BMS-986325 variants: BMS-986325 and variant antibodies were titrated in complete media and pipetted in duplicate to 96 well round bottom plates. $2\times10^5$ tonsillar B cells were added, and stimulated with soluble hIL-4 (20 ng/ml, PeproTech, Inc.), antibody alone, or antibody plus IL-4 and soluble IZ-hCD40L (3 µg/ml). Plates were incubated at 37° C. in a humidified incubator with 5% CO2 for 72 hours.

Media was sampled at 48 hours for IL-6 measurement by AlphaLisa® (cat. #AL3025C, Perkin Elmer; Waltham, MA) according to the manufacturer's instructions and read on the EnVision® 2105 multimode plate reader (Perkin Elmer; Waltham, MA). For IL-6 production, greater than 2-fold induction over control was considered to be a positive indication of agonism.

During the last 7 hours of incubation, cells were labeled with 0.5 µCi of [methyl-$^3$H]-thymidine (Perkin Elmer, Waltham, MA) per well, harvested on glass fiber filter plates, and counted by liquid scintillation on a Packard Topcount® NXT™ counter (Perkin Elmer, Waltham, MA). B cell proliferation was quantitated based on thymidine incorporation. For analysis, duplicate values were averaged and quantitated using GraphPad Prism software (ver. 7, GraphPad Software, San Diego, CA). Greater than 2-fold induction over control, unstimulated, or IL-4 alone, was considered to be positive for agonism.

Single-dose pharmacokinetic study in C57BL/6 mice after 1 mg/kg intravenous administration of BMS-986325 and its variants: As neither BMS-986325 nor its variants crossreact to murine CD40, the PK thus collected was "intrinsic PK" of the antibody without any impact of target mediated drug disposition (TMDD), typical in anti-CD40 antibodies. Briefly, 1 mg/kg antibody in phosphate buffer saline (PBS) was administered intravenously (IV) in C57/BL6 mice and 10 µL whole-blood was collected in tubes containing 90 µL of Rexxip® A Buffer (Gyros Protein Technologies, Tucson, AZ) over time for 6 weeks. The tubes, after being thoroughly mixed, were frozen until bioanalysis.

Analysis of BMS-986325 and its variants in mice microsamples by Gyros immunoassay: After thawing, the blood samples were centrifuged and supernatants were analyzed for antibody using a qualified automated, microfluidic fluorescence immunoassay on the Gyrolab® xP Workstation (Gyros Protein Technologies, Tucson, AZ). Briefly, biotinylated huCD40-mouse IgG2b at 100 µg/ml was used as a capture molecule for the "active/free" antibody. Samples were analyzed at 10% minimum required dilution in 1% BSA/PBS/0.05% Tween®20 (PTB; Croda International, Edison, NJ). Standard, QC, and study samples were brought up to a final matrix concentration of 10% mouse blood in Rexxip® A Buffer and loaded onto Gyrolab. The three-step Wizard method with Gyrolab® Bioaffy 200 CD was used. After final wash steps, the captured "active/free" antibody was detected using Alexa 64-labeled monkey anti-human IgG Fc mAb clone 1628.3379.1007.D12. The concentrations of antibody ("active/free") in blood samples were calculated based on the corresponding fluorescence intensity as measured by Gyrolab using a 4PL (parameter logistic) regression standard calibration curve. Assay performance was within the acceptable range with % CV of the standards and QCs being below 20%, and QC recovery within ±20% of the nominal values.

These data are consistent with the hypothesis that the specific site or location of a mutation to modify a surface charge patch rather than just modifying the total antibody charge, is critical to improving antibody PK. For example, variants with 1 or 2 strategically placed mutations and less change in overall charge of −2 (M33) or −3 (M47) have equivalent or better PK compared to a mutant with 6 mutations and larger change in charge of −8 (M53).

Although the present embodiments have been described in detail with reference to examples above, it is understood that various modifications can be made without departing from the spirit of these embodiments, and would readily be known to the skilled artisan.

These and other aspects disclosed herein, including the exemplary specific treatment methods, medicaments, and uses listed herein, will be apparent from the teachings contained herein.

The invention claimed is:

1. An isolated antibody, or antigen binding portion thereof, that specifically binds to human CD40, wherein said antibody comprises a first polypeptide portion comprising a heavy chain variable region, and a second polypeptide portion comprising a light chain variable region, wherein:

(i) said heavy chain variable region comprises SEQ ID NO. 40; and said light chain variable region comprises SEQ ID NO. 41;

(ii) said heavy chain variable region comprises SEQ ID NO. 40; and said light chain variable region comprises SEQ ID NO. 42;

(iii) said heavy chain variable region comprises SEQ ID NO. 43; and said light chain variable region comprises SEQ ID NO. 42;

(iv) said heavy chain variable region comprises SEQ ID NO. 44; and said light chain variable region comprises SEQ ID NO. 45;

(v) said heavy chain variable region comprises SEQ ID NO. 44; and said light chain variable region comprises SEQ ID NO. 42;

or (vi) said heavy chain variable region comprises SEQ ID NO. 46; and said light chain variable region comprises SEQ ID NO. 41.

2. The isolated antibody, or antigen binding portion thereof, of claim 1, wherein said first polypeptide portion comprises or consists of an amino acid sequence selected from the group consisting of:

(i) SEQ ID NO: 91;

(ii) SEQ ID NO. 84;

(iii) SEQ ID NO: 85.

3. The antibody or antigen binding portion thereof of claim 1, wherein the antigen binding portion is an scFv-Fc.

4. The antibody or antigen binding portion thereof of claim 1, wherein the antibody or antigen-binding portion thereof is linked to a therapeutic agent, is linked to a second functional moiety having a different binding specificity than said antibody or antigen binding portion thereof, or further comprises an additional moiety.

5. A pharmaceutical composition comprising: a) the antibody, or antigen binding portion thereof, of claim 1; and b) a pharmaceutically acceptable carrier.

6. The isolated antibody, or antigen binding portion thereof, of claim 1, wherein:

(i) said first polypeptide portion comprises SEQ ID NO. 47; and said second polypeptide portion comprises SEQ ID NO. 20;

(ii) said first polypeptide portion comprises SEQ ID NO. 47; and said second polypeptide portion comprises SEQ ID NO. 19;

(iii) said first polypeptide portion comprises SEQ ID NO. 86; and said second polypeptide portion comprises SEQ ID NO. 19;

(iv) said first polypeptide portion comprises SEQ ID NO. 49; and said second polypeptide portion comprises SEQ ID NO. 17;

(v) said first polypeptide portion comprises SEQ ID NO. 49; and said second polypeptide portion comprises SEQ ID NO. 19;

or (vi) said first polypeptide portion comprises SEQ ID NO. 50; and said second polypeptide portion comprises SEQ ID NO. 20.

7. The isolated antibody, or antigen binding portion thereof, of claim 1, wherein:

(i) said first polypeptide portion comprises SEQ ID NO. 56; and said second polypeptide portion comprises SEQ ID NO. 20;

(ii) said first polypeptide portion comprises SEQ ID NO. 56; and said second polypeptide portion comprises SEQ ID NO. 19;

(iii) said first polypeptide portion comprises SEQ ID NO. 35; and said second polypeptide portion comprises SEQ ID NO. 19;

(iv) said first polypeptide portion comprises SEQ ID NO. 84; and said second polypeptide portion comprises SEQ ID NO. 17;

(v) said first polypeptide portion comprises SEQ ID NO. 84; and said second polypeptide portion comprises SEQ ID NO. 19;

or (vi) said first polypeptide portion comprises SEQ ID NO. 85; and said second polypeptide portion comprises SEQ ID NO. 20.

8. The isolated antibody, or antigen binding portion thereof, of claim 1, wherein said heavy chain variable region comprises SEQ ID NO. 40; and said light chain variable region comprises SEQ ID NO. 41.

9. The isolated antibody, or antigen binding portion thereof, of claim 1, wherein said heavy chain variable region comprises SEQ ID NO. 40; and said light chain variable region comprises SEQ ID NO. 42.

10. The isolated antibody, or antigen binding portion thereof, of claim 1, wherein said heavy chain variable region comprises SEQ ID NO. 43; and said light chain variable region comprises SEQ ID NO. 42.

11. The isolated antibody, or antigen binding portion thereof, of claim 1, wherein said heavy chain variable region comprises SEQ ID NO. 44; and said light chain variable region comprises SEQ ID NO. 45.

12. The isolated antibody, or antigen binding portion thereof, of claim 1, wherein said heavy chain variable region comprises SEQ ID NO. 44; and said light chain variable region comprises SEQ ID NO. 42.

13. The isolated antibody, or antigen binding portion thereof, of claim 1, wherein said heavy chain variable region comprises SEQ ID NO. 46; and said light chain variable region comprises SEQ ID NO. 41.

* * * * *